(12) United States Patent
Ashley et al.

(10) Patent No.: US 6,939,861 B2
(45) Date of Patent: Sep. 6, 2005

(54) AMIDO MACROLIDES

(75) Inventors: Gary Ashley, Alameda, CA (US);
Simon James Shaw, San Francisco, CA (US); Yandong Li, San Leandro, CA (US); David C. Myles, Kensington, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 194 days.

(21) Appl. No.: 10/347,512

(22) Filed: Jan. 17, 2003

(65) Prior Publication Data

US 2003/0199458 A1 Oct. 23, 2003

Related U.S. Application Data

(63) Continuation-in-part of application No. 10/124,988, filed on Apr. 17, 2002, which is a continuation of application No. 09/551,162, filed on Apr. 14, 2000, now Pat. No. 6,451,768, which is a continuation-in-part of application No. 09/550,045, filed on Apr. 14, 2000, now Pat. No. 6,395,710, said application No. 10/347,512, is a continuation-in-part of application No. 10/075,466, filed on Feb. 13, 2002, now Pat. No. 6,593,302, which is a continuation of application No. 09/550,045.

(60) Provisional application No. 60/350,153, filed on Jan. 17, 2002, provisional application No. 60/129,729, filed on Apr. 16, 1999, provisional application No. 60/140,175, filed on Jun. 18, 1999, provisional application No. 60/172,154, filed on Dec. 17, 1999, provisional application No. 60/172,159, filed on Dec. 17, 1999, provisional application No. 60/173,804, filed on Dec. 30, 1999, provisional application No. 60/173,805, filed on Dec. 30, 1999, provisional application No. 60/140,175, provisional application No. 60/172,154, provisional application No. 60/172,159, provisional application No. 60/173,804, and provisional application No. 60/173,805.

(51) Int. Cl.[7] .................... A61K 31/70; C07H 17/08
(52) U.S. Cl. .................................. 514/29; 536/7.4
(58) Field of Search ............................ 514/29; 536/7.4

(56) References Cited

U.S. PATENT DOCUMENTS

| 4,474,768 A | * 10/1984 | Bright ........................ 514/29 |
| 5,527,780 A | 6/1996 | Agouridas et al. |

(Continued)

FOREIGN PATENT DOCUMENTS

| WO | WO 97/02358 | 1/1997 |
| WO | WO 98/01546 | 1/1998 |
| WO | WO 98/01571 | 1/1998 |
| WO | WO 98/09978 | 3/1998 |
| WO | WO 99/03986 | 1/1999 |
| WO | WO 99/21871 | 5/1999 |
| WO | WO 99/35157 | 7/1999 |
| WO | WO 00/26224 | 5/2000 |
| WO | WO 00/26349 | 5/2000 |
| WO | WO 00/34297 | 6/2000 |
| WO | WO 00/44761 | 8/2000 |
| WO | WO 00/71557 | 11/2000 |

*Primary Examiner*—Elli Peselev
(74) *Attorney, Agent, or Firm*—Foley & Lardner LLP

(57) ABSTRACT

Various macrolide compounds such as those having the following formulas are provided where the variables have the values provided herein.

29 Claims, 3 Drawing Sheets

U.S. PATENT DOCUMENTS

| | | |
|---|---|---|
| 5,635,485 A | 6/1997 | Agouridas et al. |
| 5,672,491 A | 9/1997 | Khosla et al. |
| 5,747,467 A | 5/1998 | Agouridas et al. |
| 5,750,510 A | 5/1998 | Elliott et al. |
| 5,770,579 A | 6/1998 | Agouridas et al. |
| 5,866,549 A | 2/1999 | Or et al. |
| 6,022,965 A | 2/2000 | Benedetti et al. |
| 6,043,226 A | 3/2000 | Lundy et al. |
| 6,066,721 A | 5/2000 | Khosla et al. |
| 6,080,555 A | 6/2000 | Khosla et al. |
| 6,100,240 A | 8/2000 | Cheng et al. |
| 6,121,432 A | 9/2000 | Bonnet et al. |
| 6,124,269 A * | 9/2000 | Phan et al. ............ 514/29 |
| 6,271,255 B1 | 8/2001 | Leadlay et al. |
| 6,274,560 B1 | 8/2001 | Khosla et al. |
| 6,274,715 B1 | 8/2001 | Or et al. |
| 6,451,768 B1 * | 9/2002 | Chu ...................... 514/29 |
| 6,562,795 B2 * | 5/2003 | Ashley et al. .......... 514/29 |

* cited by examiner

AMIDO MACROLIDES

CROSS-REFERENCES TO RELATED APPLICATIONS

This application claims priority to U.S. Provisional Application No. 60/350,153 filed on Jan. 17, 2002, the entire disclosure of which is herein incorporated by reference and for all purposes, and this application also claims priority as a continuation-in-part of U.S. Ser. No. 10/124,988, filed on Apr. 17, 2002, pending, which is a continuation of U.S. Ser. No. 09/551,162, filed on Apr. 14, 2000, now U.S. Pat. No. 6,451,768, which is a continuation-in-part of U.S. Ser. No. 09/550,045, filed on Apr. 14, 2000, now U.S. Pat. No. 6,395,710 and which also claims priority to U.S. Provisional Application No. 60/129,729, filed on Apr. 16, 1999, now abandoned; U.S. Provisional Application No. 60/140,175, filed on Jun. 18, 1999, now abandoned; U.S. Provisional Application No. 60/172,154, filed on Dec. 17, 1999, now abandoned; U.S. Provisional Application No. 60/172,159, filed on Dec. 17, 1999, now abandoned; U.S. Provisional Application No. 60/173,804, filed on Dec. 30, 1999, now abandoned; and U.S. Provisional Application No. 60/173,805, filed on Dec. 30, 1999, now abandoned, and this application also claims priority as a continuation-in-part of U.S. Ser. No. 10/075,466, filed on Feb. 13, 2002, now U.S. Pat. No. 6,593,302, which is a continuation of Ser. No. 09/550,045, filed on Apr. 14, 2000, now U.S. Pat. No. 6,395,710, which claims priority to U.S. Provisional Application No. 60/129,729, filed on Apr. 16, 1999, now abandoned; U.S. Provisional Application No. 60/140,175, filed on Jun. 18, 1999, now abandoned; U.S. Provisional Application No. 60/172,154, filed on Dec. 17, 1999, now abandoned; U.S. Provisional Application No. 60/172,159, filed on Dec. 17, 1999, now abandoned; U.S. Provisional Application No. 60/173,804, filed on Dec. 30, 1999, now abandoned; and U.S. Provisional Application No. 60/173,805, filed on Dec. 30, 1999, now abandoned.

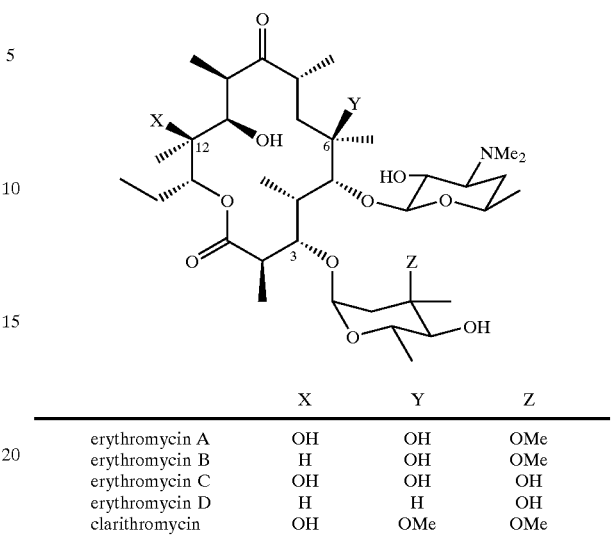

| | X | Y | Z |
|---|---|---|---|
| erythromycin A | OH | OH | OMe |
| erythromycin B | H | OH | OMe |
| erythromycin C | OH | OH | OH |
| erythromycin D | H | H | OH |
| clarithromycin | OH | OMe | OMe |

BACKGROUND OF THE INVENTION

Erythromycins are macrolide antibiotics, glycosylated polyketides originally discovered in 1952 in the metabolic products of a strain of *Streptomyces erythreus*, now classified as *Saccharopolyspora erythraea*. The antibiotic occurs in various forms, designated A, B, C, and D. Since their discovery, many have worked to prepare derivatives of the molecule to improve or modify its properties. The focus of much of this work involved chemical modification of the naturally produced erythromycin molecule. For example, clarithromycin is a semi-synthetic antibiotic that is made by chemically methylating the hydroxyl group at C-6.

Azalides, such as azithromycin, are erythromycin derivatives where the C-9 ketone has been replaced with a N—$CH_2$ unit through a Beckmann rearrangement. See, for example, O'Connell et al., "Azalides and methods of making same," U.S. Pat. No. 6,270,768, incorporated herein by reference.

Ketolides are erythromycin derivatives where the C-3 cladinose sugar is chemically removed and the resulting free hydroxyl group converted into a keto group. For example, Phan et al., "2-Halo-6-O-substituted ketolide derivatives," U.S. Pat. No. 6,124,269 describes ketolides with a cyclic carbamate group at C-11 and C-12 and an O-alkylaryl group at C-6. Agouridas et al., "Erythromycin compounds," U.S. Pat. No. 5,635,485 also describes ketolides with a cyclic carbamate group at C-11 and C-12 but which have a -OMe group at C-6 and an alkylaryl group at the carbamate nitrogen.

The complexity of the macrolide molecule has limited medicinal chemistry efforts to produce derivatives of the naturally occurring erythromycins and their precursors. Recently, the discovery and isolation of modular polyketide synthases ("PKS's") have expanded the scope of macrolide structures that may be made. PKS's are multifunctional enzymes that catalyze the formation of the polyketide chains through repeated reactions between acylthioesters.

The *Sac. erythraea* PKS, known as 6-deoxyerythronolide B synthase (DEBS), is an assembly of three multifunctional proteins encoded by the eryAI, eryAII, and eryAIII genes and is described in Katz et al., "Recombinant DNA method for producing erythromycin analogs," U.S. Pat. No. 5,824,513; Katz et al., "Method of directing biosynthesis of specific polyketides," U.S. Pat. No. 6,004,787; Katz et al., "Polyketide derivatives and recombinant methods for making same," U.S. Pat. Nos. 6,060,234, 6,063,561, and 6,200,813; each of which is incorporated herein by reference. DEBS produces the polyketide macrolactone 6-deoxyerythronolide B, which is processed by additional tailoring enzymes present in *Sac. erythraea* to make erythromycins A-D. The collective assembly of the PKS gene and the genes for the tailoring enzymes are referred to as the biosynthetic gene cluster. The organization of the gene cluster is described in Summers et al., "Polyketide-associated sugar biosynthesis genes," U.S. Pat. No. 5,998, 194, incorporated herein by reference.

Recombinant methods using vectors encoding a variety of PKS's, including the PKS from *Sac. erythraea*, to make novel polyketides are described in Khosla et al., "Recombinant production of novel polyketides," U.S. Pat. Nos. 5,672,491, 5,830,750, 5,962,290, 6,022,731, and 6,077,696; Khosla et al., "Recombinant combinatorial genetic library for the production of novel polyketides," U.S. Pat. No. 5,712,146; Khosla et al., "Method to produce novel polyketides," U.S. Pat. Nos. 6,066,721, 6,221,641, and 6,261,816; Barr et al., "Production of polyketides in bacteria and yeast," U.S. Pat. Nos. 6,033,883 and 6,258,566 and PCT publication WO 98/27203; Khosla et al., "Biosynthesis of polyketide synthase substrates," PCT publication WO 01/27305; and Santi et al., "Heterologous production of polyketides," PCT publication WO 01/31035; each of which is incorporated herein by reference. Leadlay et al., "Erythromycins and process for their preparation, "U.S. Pat. No. 6,271,255, incorporated herein by reference, describes additional methods for modifying the loading domain and thus varying the nature of the starter units that initiate polyketide synthesis. Methods for making polyketides in a cell-free system are described, for example by Khosla et al., "Synthesis of polyketides from diketides," U.S. Pat. No. 6,080, 555; Khosla et al., "Cell-free synthesis of polyketides," U.S. Pat. No. 6,274,560, and PCT Publication No. WO 97/02358, each of which is incorporated herein by reference. Erythromycin analogues where the naturally occurring ethyl group at C-13 is replaced with other groups have been described, for example in Dirlam et al., "Novel macrolides," PCT publication WO 99/35156; Jin, "Novel erythromycin derivatives," PCT publication WO 99/35157; Ashley et al., "Synthesis of oligoketides," U.S. Pat. No. 6,492,562; McMillen & Kaneko, "Ketolide antibiotics," PCT publication WO 00/44761; Grant et al., "Ketolide antibacterials," PCT publication WO 00/62783; and Chu, "Anti-infective compounds," U.S. Pat. Nos. 6,395,710 and 6,451,768 and PCT publication WO 01/49699; and Xue et al., "Multi-plasmid approach to preparing large libraries of polyketides," PCT publication WO 00/63361; each of which is incorporated herein by reference.

Various macrolides are also disclosed in U.S. Pat. Nos. 6,451,768 and 6,395,710 both of which are incorporated herein by reference in their entirety and for all purposes. U.S. Pat. No. 6,492,562, also herein incorporated by reference in its entirety for all purposes, describes methods for preparing various macrolides.

Due to the increase in the incidence of resistant strains to currently used antibiotics, a need exists for novel compounds having antibiotic activity, particularly against resistant strains. The present invention fulfills this need by providing novel erythromycins, ketolides, and azalides.

SUMMARY OF THE INVENTION

The invention provides various compounds and pharmaceutically acceptable salts thereof. Thus, in one embodiment, the invention provides compounds and pharmaceutically acceptable salts thereof of the formula I

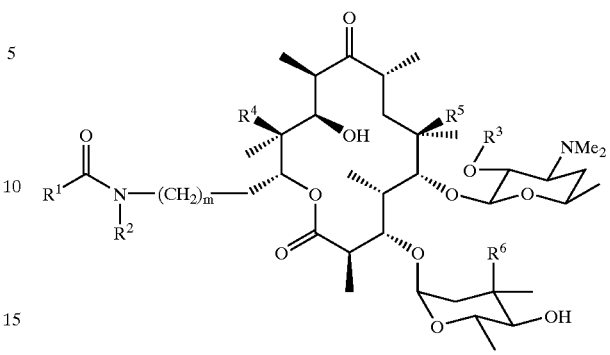

where:

$R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl;

$R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;

$R^3$ is H, $C_1$–$C_4$ alkanoyl, or benzoyl;

$R^4$ is H or OH;

$R^5$ is H, OH, $C_1$–$C_4$ alkoxy, $C_2$–$C_4$ alkenyloxy, or $C_2$–$C_4$ alkynyloxy;

$R^6$ is OH or OMe; and m=0–2.

In some embodiments, the invention provides compounds of formula I where $R^2$ is H and m is 0. In other embodiments, the invention provides compounds of formula I where $R^2$ is H and m is 1. In yet other embodiments, the invention provides compounds of formula I where $R^2$ is H and m is 2.

In still other embodiments, the invention provides compounds of formula I which have any of the following structures:

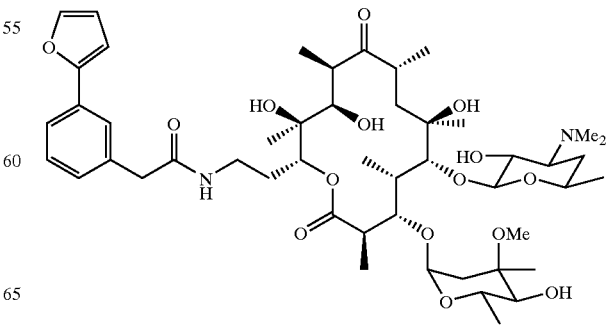

-continued

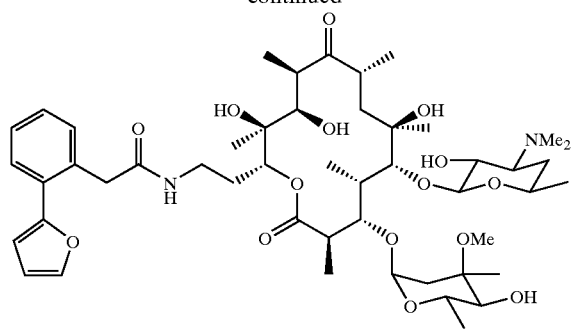

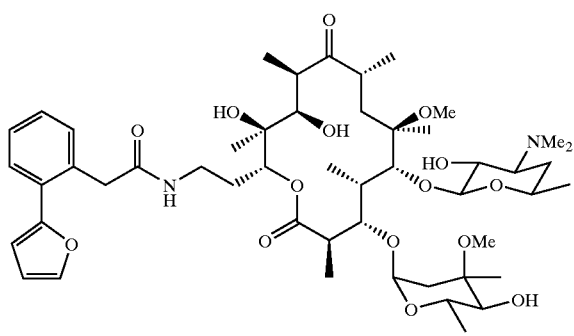

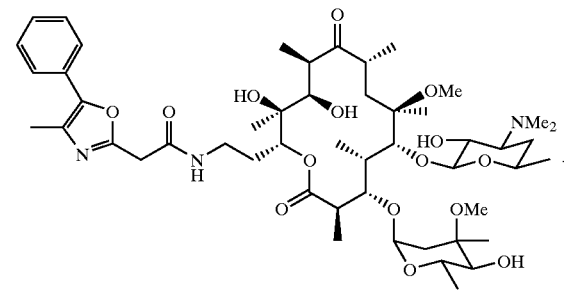

In another aspect, the invention provides compounds of formula II and pharmaceutically acceptable salts thereof

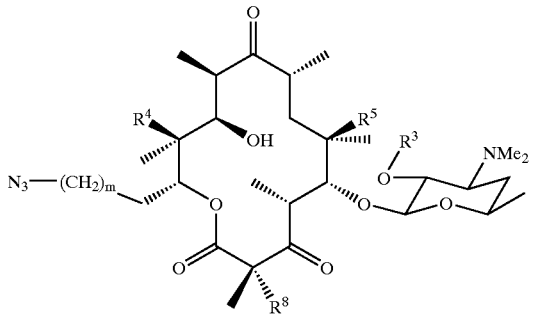

II where:

$R^3$ is H, $C_1$–$C_4$ alkanoyl, or benzoyl;

$R^4$ is H or OH;

$R^5$ is H, $C_1$–$C_4$ alkoxy, $C_2$–$C_4$ alkenyloxy, or $C_2$–$C_4$ alkynyloxy;

$R^8$ is H or F; and m=0–2.

In some embodiments, the invention provides compounds of formula II where m is 0. In other embodiments, the invention provides compounds of formula II where m is 1. In yet other embodiments, the invention provides compounds of formula II where m is 2.

In a further embodiment, the invention provides compounds of formula II which have any of the following structures:

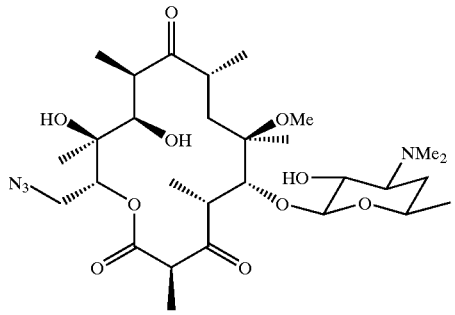

or

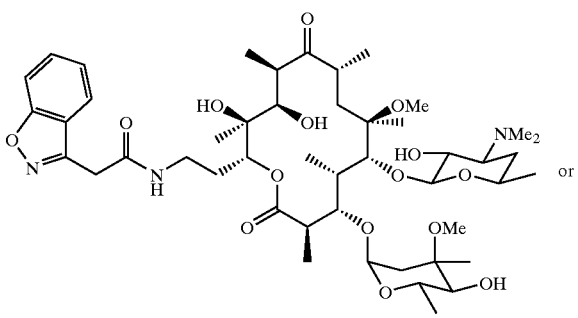

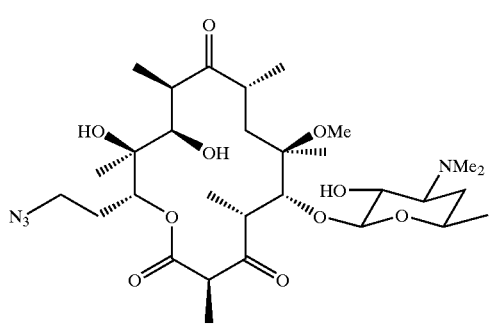

-continued

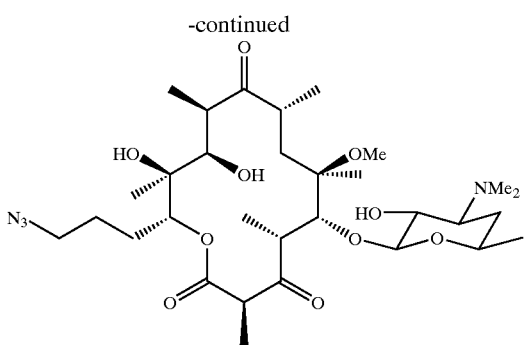

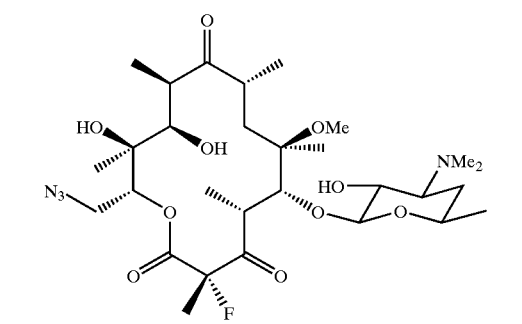

or

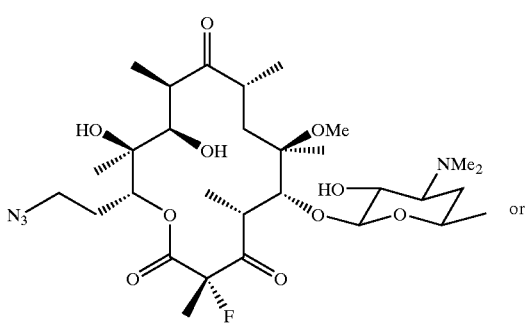

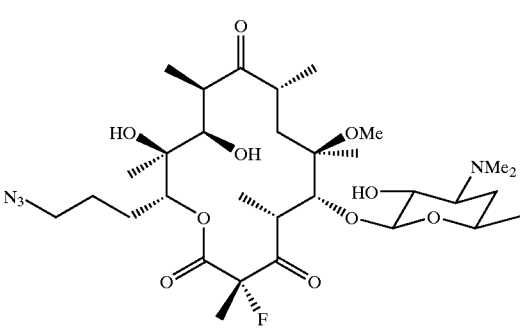

In yet another aspect, the invention provides compounds of formula III and pharmaceutically acceptable salts thereof

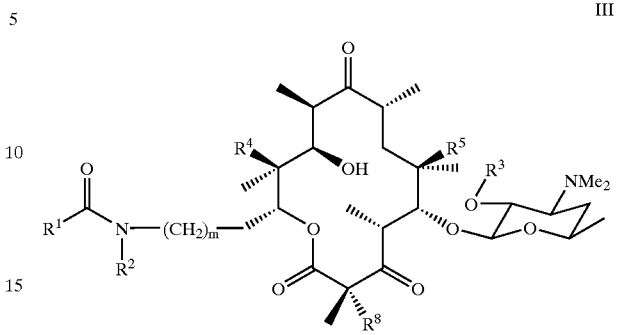

III where:

$R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl;

$R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;

$R^3$ is H, $C_1$–$C_4$ alkanoyl, or benzoyl;

$R^4$ is H or OH;

$R^5$ is H, $C_1$–$C_4$ alkoxy, $C_2$–$C_4$ alkenyloxy, or $C_2$–$C_4$ alkynyloxy;

$R^8$ is H or F; and m=0–2.

In some embodiments, the invention provides compounds of formula III in which m is 0. In other embodiments, the invention provides compounds of formula III in which m is 1. In still other embodiments, the invention provides compounds of formula II in which m is 2. In some such embodiments, the invention provides compounds of formula III where $R^2$ is H and m is 0. In other such embodiments, the invention provides compounds of formula III where $R^2$ is H and m is 1. In yet other such embodiments, the invention provides compounds of formula III where $R^2$ is H and m is 2.

In yet other embodiments, the invention provides compounds of formula III in which $R^1$ is a $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; and $R^2$ is H.

In still another aspect, the invention provides compounds of formula IV and pharmaceutically acceptable salts thereof

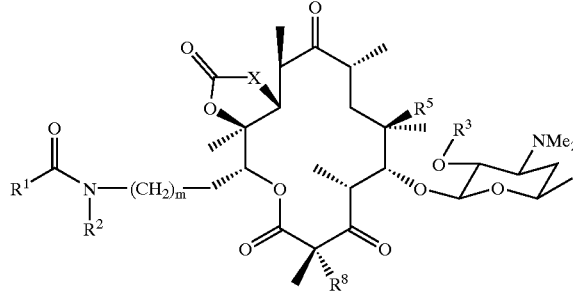

IV where:
- $R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl;
- $R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;
- $R^3$ is H, $C_1$–$C_4$ alkanoyl, or benzoyl;
- $R^5$ is H, $C_1$–$C_4$ alkoxy, $C_2$–$C_4$ alkenyloxy, or $C_2$–$C_4$ alkynyloxy;
- $R^8$ is H or F;
- X is O or $NR^7$, wherein $R^7$ is H, $C_1$–$C_4$ alkyl, or $C_6$–$C_{20}$ arylalkyl; and
- m=0–2.

In some embodiments, the invention provides compounds of formula IV in which $R^2$ is H.

In still other embodiments, the invention provides compounds of formula IV in which $R^1$ is $C_6$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; and $R^2$ is H.

In still other embodiments, the invention provides compounds of formula IV in which $R^1$ is $C_6$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; $R^2$ is H; and X is NH.

In yet other embodiments, the invention provides compounds of formula IV which have any of the following structures:

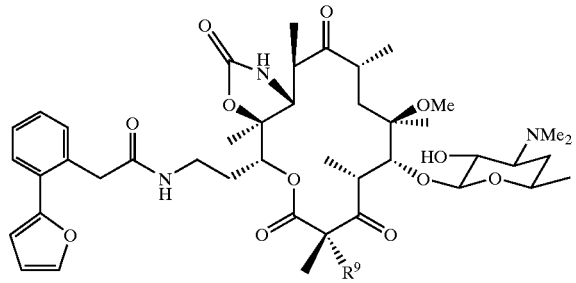

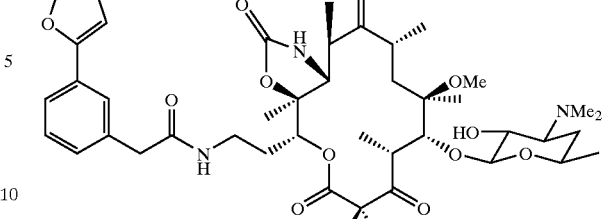

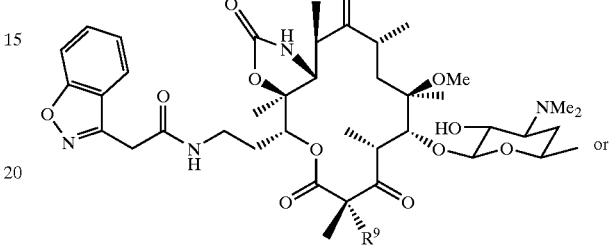

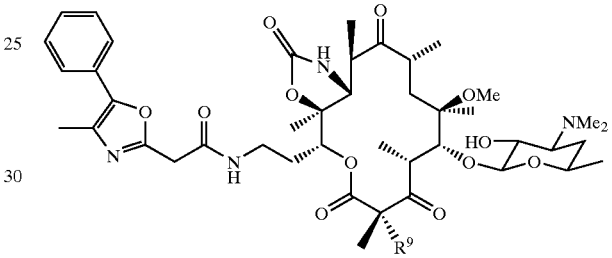

where $R^9$ is H or F.

In yet other embodiments, the invention provides compounds of formulas I, III, or IV in which $R^1$ is a group having any of the following formulas:

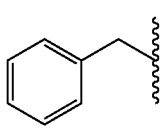
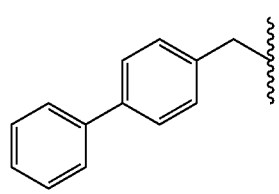
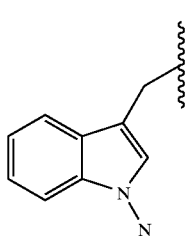
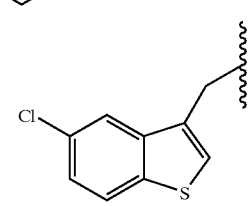
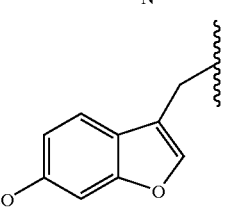
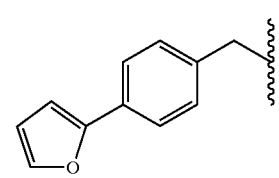

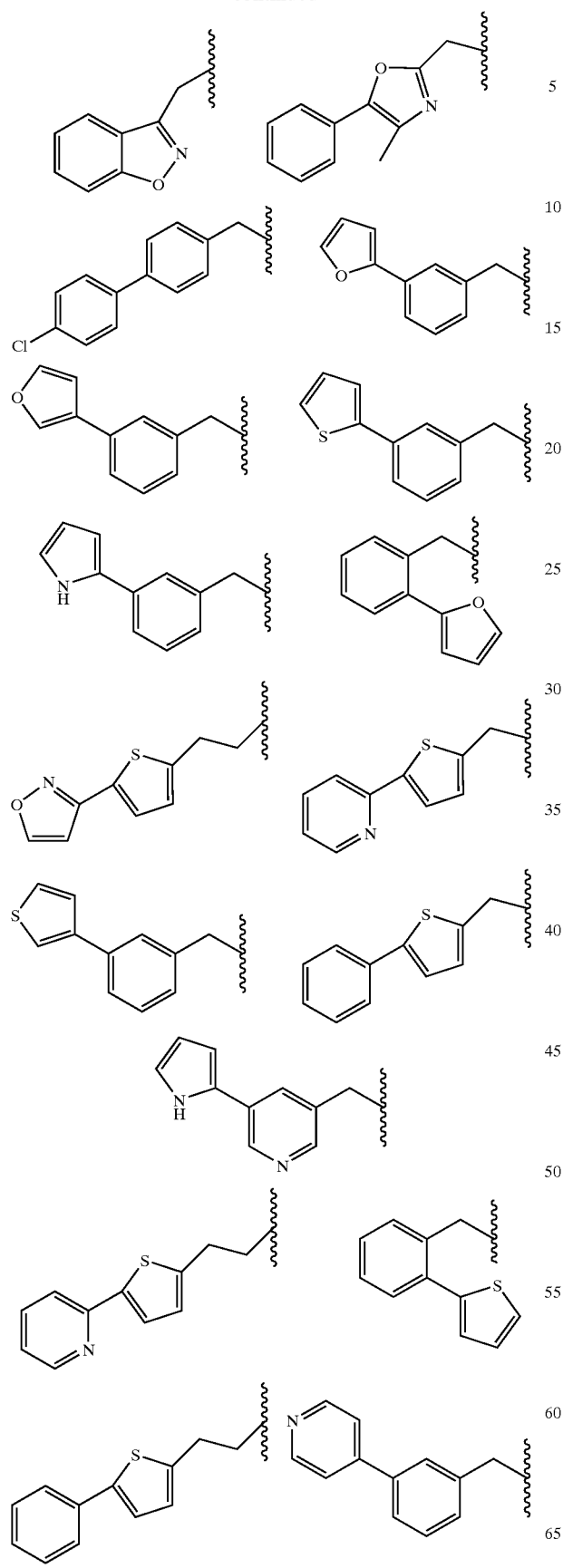

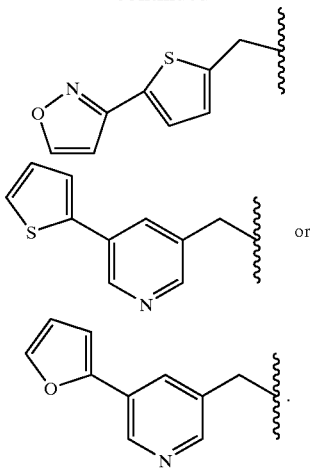

In one embodiment, the invention provides compounds of the formula V and pharmaceutically acceptable salts thereof

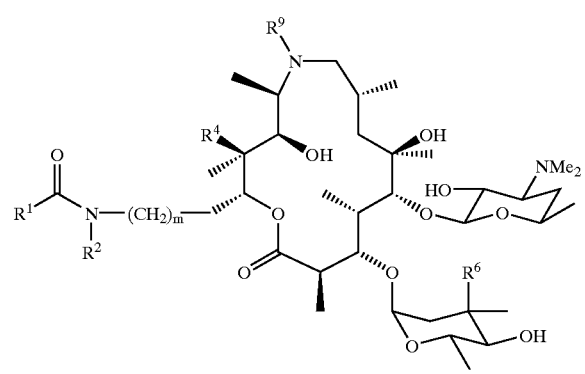

(V)

wherein

R$^1$ is C$_1$–C$_8$ substituted or unsubstituted alkyl, C$_2$–C$_8$ substituted or unsubstituted alkenyl, C$_2$–C$_8$ substituted or unsubstituted alkynyl, C$_4$–C$_{15}$ substituted or unsubstituted aryl, C$_5$–C$_{20}$ substituted or unsubstituted arylalkyl, C$_5$–C$_{20}$ substituted or unsubstituted biarylalkyl, C$_5$–C$_{20}$ substituted or unsubstituted arylalkenyl, or C$_5$–C$_{20}$ substituted or unsubstituted arylalkynyl;

R$^2$ is H, C$_1$–C$_4$ substituted or unsubstituted alkyl, C$_2$–C$_4$ substituted or unsubstituted alkenyl, or C$_2$–C$_4$ substituted or unsubstituted alkynyl;

R$^4$ is H or OH;

R$^6$ is OH or OMe;

R$^9$ is H or C$_1$–C$_4$ alkyl; and m=0–2.

In still other embodiments, the invention provides pharmaceutical formulations and medicaments. Such pharmaceutical formulations and medicaments include any of the compounds of the invention and a pharmaceutically acceptable carrier. In some embodiments, the pharmaceutical formulation or medicament includes any compound of formulae I–V and a pharmaceutically acceptable carrier.

In another embodiment, the invention provides a method of treating a bacterial infection with compounds of the formulae I–V. A method of treating a bacterial infection includes administering a compound of formulae I–V to a patient in need thereof. In one embodiment, the bacterial infection results from Gram positive bacteria, Gram negative bacteria or anaerobic bacteria. In another embodiment, the bacteria are *Staphylococcus aureus, Streptococcus epidermidis, Strep. pneumoniae, Strep. pyogenes*, enterococci, *Moraxella catarrhalis* or *Haemophilus influenzae*. In yet another embodiment, the bacterial infection is community-acquired pneumonia, acute exacerbated chronic bronchitis, acute sinusitis, tonsillitis/pharyngitis, upper respiratory tract infection, lower respiratory tract infection, skin infection, soft tissue infection, meningitis, hospital-acquired infection, bone infection or joint infection.

In another embodiment, the invention provides a method of treating a gastric motility disease. The method includes treating a patient with gastric motility disease with a compound of formula I. In one embodiment, the gastric motility disease is gastro-esophageal reflux disease (GERD), post-operative ileus, diabetes, or gastroparesis.

Other objects, features, and advantages of the present invention will become apparent from the following detailed description. It should be understood, however, that the detailed description and the specific examples, while indicating some preferred embodiments of the invention, are given by way of illustration only, since various changes and modifications whiting the spirit and scope of the invention will become apparent to those skilled in the art from this detailed description.

DETAILED DESCRIPTION OF THE INVENTION

Figure 1:
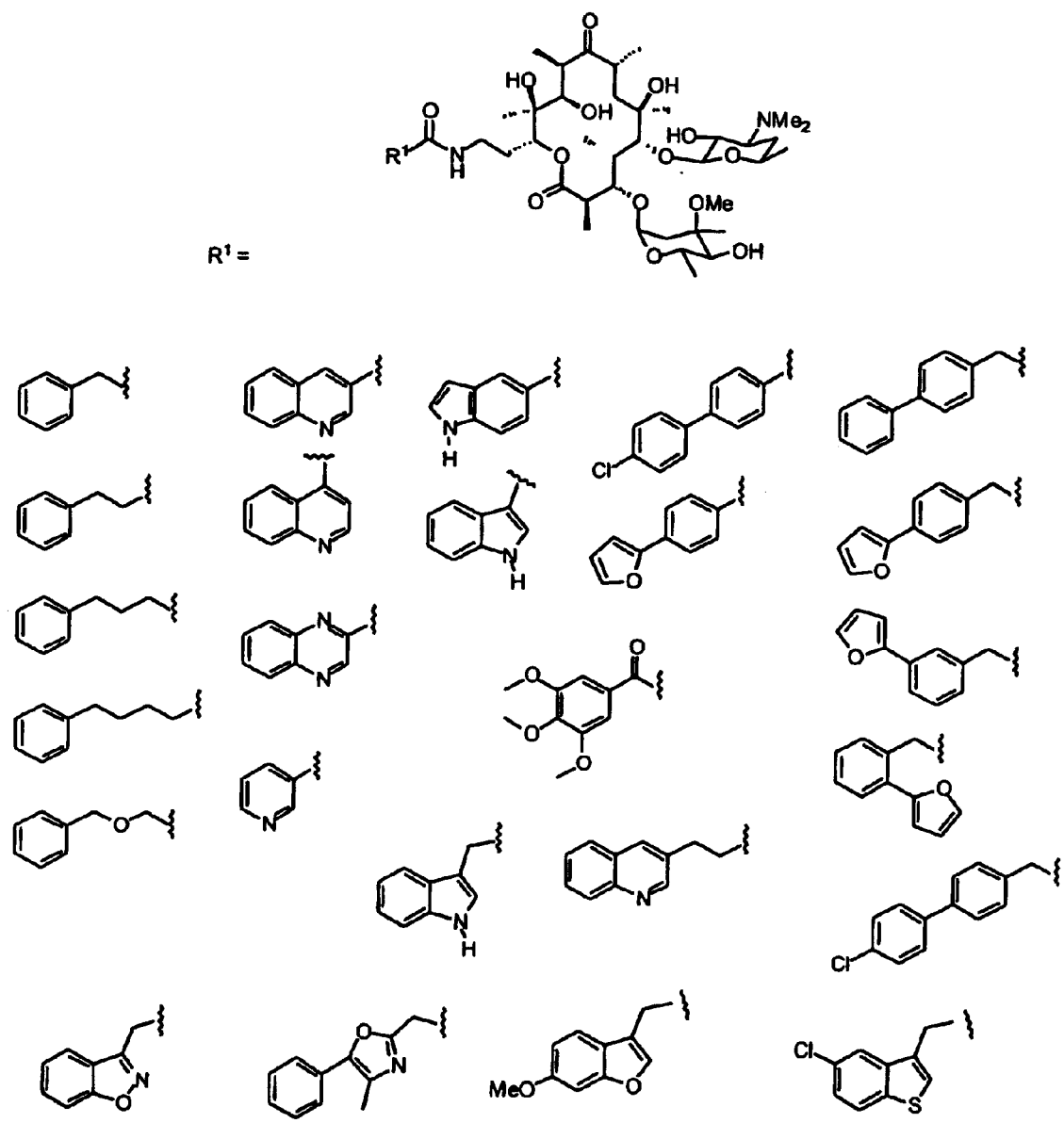
FIG. 1 shows a variety of 15-amidoerythromycins prepared according to the methods of the invention.
Figure 2:
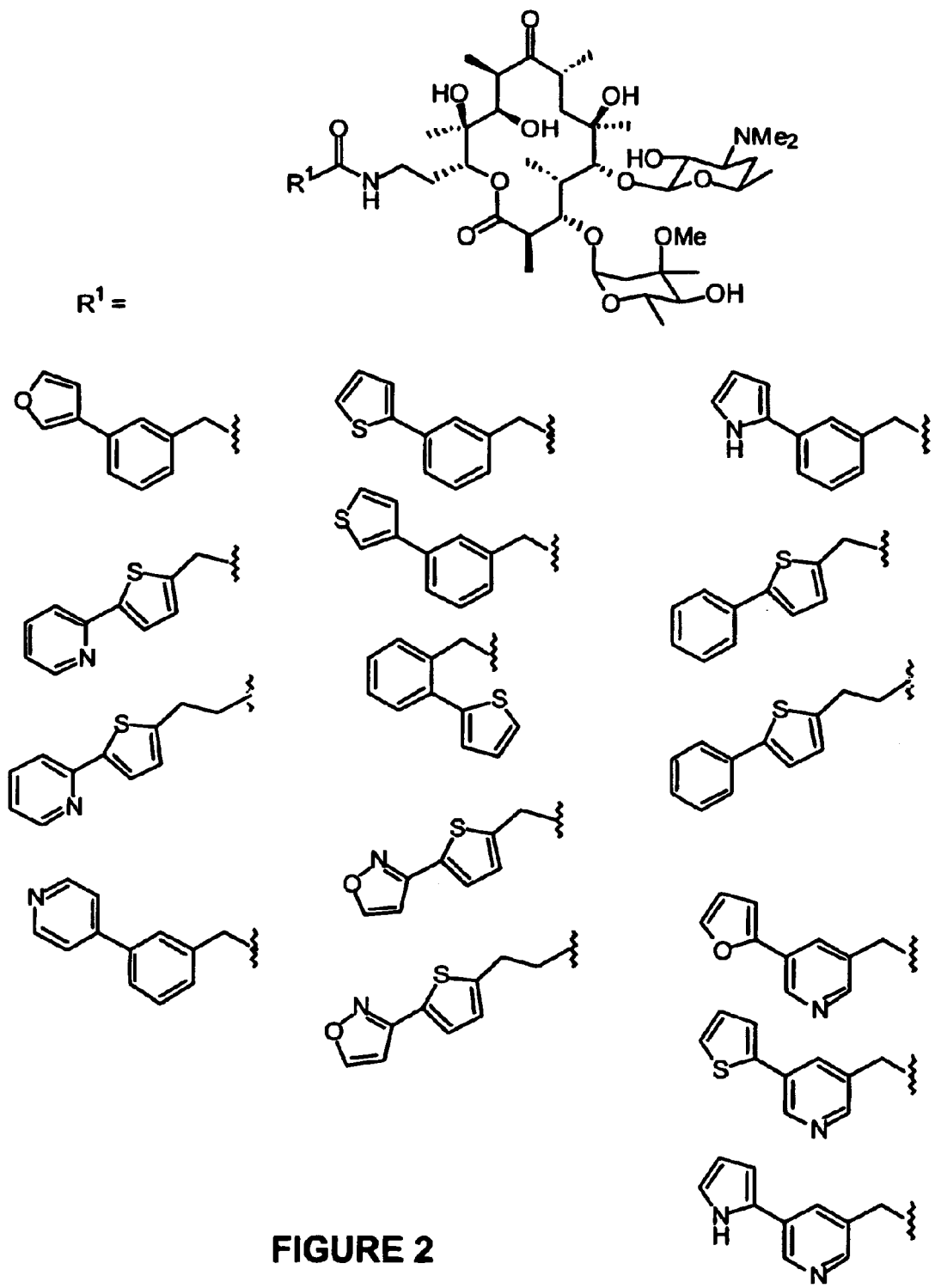
FIG. 2 shows some embodiments of additional 15-amidoerythromycins that can be prepared according to the methods of the invention.

The present invention relates to erythromycin derivatives, intermediates thereto, and methods for their use in the treatment of disease. The inventive compounds possess antibacterial activity against Gram positive, Gram negative, and anaerobic bacteria, and are useful as broad-spectrum antibacterial agents for the treatment of bacterial infections in humans and animals. These compounds are effective against diverse strains including but not limited to *Staphylococcus aureus, Streptococcus epidermidis, Strep. pneumoniae, Strep. pyogenes*, enterococci, *Moraxella catarrhalis* and *Haemophilus influenzae*. Exemplary infections that may be treated include community-acquired pneumonia, acute exacerbated chronic bronchitis, acute sinusitis, tonsillitis/pharyngitis, upper and lower respiratory tract infections, skin and soft tissue infections, meningitis, hospital-acquired infections, and bone and joint infections. Certain of the inventive compounds also possess prokinetic activity and are useful in the treatment of diseases of gastric motility, including but not limited to gastro-esophageal reflux disease (GERD), post-operative ileus, diabetes, and gastroparesis.

Some of the crystalline forms for the compounds may exist as polymorphs and as such are intended to be included in the present invention. In addition, some of the compounds may form solvates with water (i.e., hydrates) or common organic solvents, and such solvates are also encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid, phosphoric acid, glucoheptonic acid, lactobionic acid, and dodecylsulfonic acid.

The present invention includes within its scope prodrugs of the compounds of this invention. In general, such prodrugs will be functional derivatives of the compounds that are readily convertible in vivo into the required compound. Examples of prodrugs of the inventive compounds include but are not limited to 2'-O-esters such as acetates, propionates, hemisuccinates, stearates, and the like. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Listed below are definitions of various terms used to describe this invention. These definitions apply to the terms as they are used throughout this specification, unless otherwise limited in specific instances, either individually or as part of a larger group.

When a particular group is "substituted," that group may have one or more substituents, preferably from one to five substituents, more preferably from one to three substituents, most preferably from one to two substituents, independently selected from the list of substituents. It is understood that substituents and substitution patterns on the compounds of this invention can be selected by one of ordinary skill in the art to provide compounds that are chemically stable and that can be readily synthesized by techniques known in the art as well as those methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thio, alkylthio, cycloalkylthio, heterocyclothio, ureido, nitro, cyano, carboxy, carboxylalkyl, carbamyl, alkoxycarbonyl, alkylthiono, arylthiono, alkylsulfonyl, sulfonamindo, aryloxy, and the like, in addition to those otherwise specified herein. The substituent may be further substituted, for example, by halo, hydroxy, alkyl, alkoxy, aryl, substituted aryl, substituted alkyl, substituted aralkyl, and the like.

Under standard nomenclature used throughout this disclosure, the terminal portion of the designated side chain is described first, followed by the adjacent functionality toward the point of attachment. Thus, for example, a "arylalkylcarboxamido" substituent refers to a group of the formula

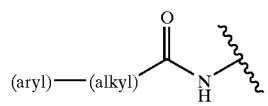

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "alkyl" refers to straight or branched chain hydrocarbons, optionally substituted. "Alkenyl" refers to a straight or branched chain hydrocarbon with at least one carbon-carbon double bond. "Alkynyl" refers to a straight or branched chain hydrocarbon with at least one carbon-carbon triple bound.

The terms "halogen," "halo," or "halide" refer to fluorine, chlorine, bromine and iodine.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclononyl, cyclodecyl, and adamantyl. Exemplary substituents include one or more alkyl groups or one or more groups described above as alkyl substituents.

The term "aryl" refers to aromatic monocyclic, fused bicyclic, or fused polycyclic hydrocarbon or heterocyclic groups having 1 to 20 carbon atoms in the ring portions, such as phenyl, naphthyl, pyrrolyl, indolyl, pyrazolyl, pyrazolinyl, imidazolyl, oxazolyl, isoxazolyl, thiazolyl, thiadazolyl, isothiazolyl, furyl, thienyl, oxadiazolyl, pyridinyl, N-oxo-pyridyl, pyrazinyl, pyrimidinyl, pyridazinyl, tetrazinyl, triazinyl, triazolyl, benzothiazolyl, benzoxazolyl, benzothienyl, quinolinyl, quinolinyl-N-oxide, isoquinolinyl, benzimidazolyl, benzofuryl, chromonyl, coumarinyl, cinnolinyl, quinoxalinyl, indazolyl, benzisothiazolyl, benzisoxazolyl, benzodiazinyl, benzofurazanyl, benzothiopyranyl, benzpyrazolyl, indolinyl, isochromanyl, isoindolinyl, naphthyridinyl, phthalazinyl, purinyl, quinazolinyl, and the like. Aryl groups may be substituted.

The term "biaryl" refers to a combination of two bonded, nonfused aryl groups as defined above. Exemplary biaryl groups include biphenyl, furylphenyl, phenylfuryl, thienylphenyl, phenylthienyl, pyridylphenyl, phenylpyridyl, furylpyridyl, pyridylfuryl, pyrrolylpyridyl, pyridylthienyl, isoxazolylthienyl, isoxazolylphenyl, and the like.

The above defined groups may be substituted by one or more substituents. Illustrative examples of substituents include but are not limited to alkyl, alkenyl, alkynyl, aryl, halo, haloalkyl, hydroxy, alkoxy, haloalkoxy, cycloalkoxy, oxo, aryloxy, alkanoyl, alkanoyloxy, amino, alkylamino, dialkylamino, arylamino, diarylamino, alkylarylamino, sulfonamido, carbonyl, carboxyl, alkoxycarbonyl, amidocarbonyl, oxoalkyl, cyano, nitro, carbamyl, guanidine, amidino, sulfonyl, and the like.

Compounds of the Invention and Their Preparation

In one aspect of the invention, compounds of formula (I) are provided

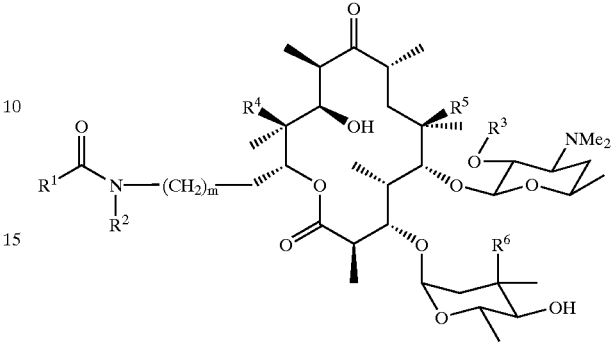

(I)

wherein $R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; $R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl; $R^3$ is H, $C_1$–$C_4$ alkanoyl, or benzoyl; $R^4$ is H or OH; $R^5$ is H, OH, $C_1$–$C_4$ alkoxy, $C_2$–$C_4$ alkenyloxy, or $C_2$–$C_4$ alkynyloxy; $R^6$ is OH or OMe; and m is 0–2.

In one embodiment of the invention, compounds of formula (I) are provided wherein $R^1$ is $C_6$–$C_{15}$ substituted or unsubstituted arylalkyl, $C_6$–$C_{15}$ substituted or unsubstituted biarylalkyl, $C_6$–$C_{15}$ substituted or unsubstituted arylalkenyl, or $C_6$–$C_{15}$ substituted or unsubstituted arylalkynyl.

In one embodiment of the invention, compounds of formula (I) are provided wherein $R^2$=H; $R^3$=H; $R^4$=H or OH; $R^5$=OH or alkoxy; $R^6$=OMe; and m=0.

In another embodiment of the invention, compounds of formula (I) are provided wherein $R^2$=H; $R^3$=H; $R^4$=H or OH; $R^5$=OH or alkoxy; $R^6$=OMe; and m=1.

In another embodiment of the invention, compounds of formula (I) are provided wherein $R^2$=H; $R^3$=H; $R^4$=H or OH; $R^5$=OH or alkoxy; $R^6$=OMe; and m=2.

In another embodiment of the invention, compounds of formula (I) are provided wherein $R^1$ is $C_4$–$C_{15}$ substituted or unsubstituted aryl, $C_5$–$C_{20}$ substituted or unsubstituted arylalkyl, or $C_5$–$C_{20}$ substituted or unsubstituted biarylalkyl; and $R^2$ is H.

In another embodiment of the invention, compounds of formula (I) having the structures

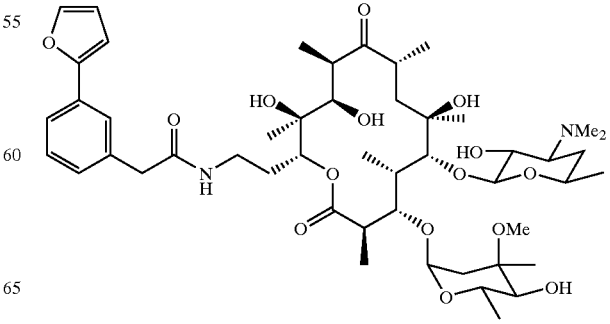

-continued

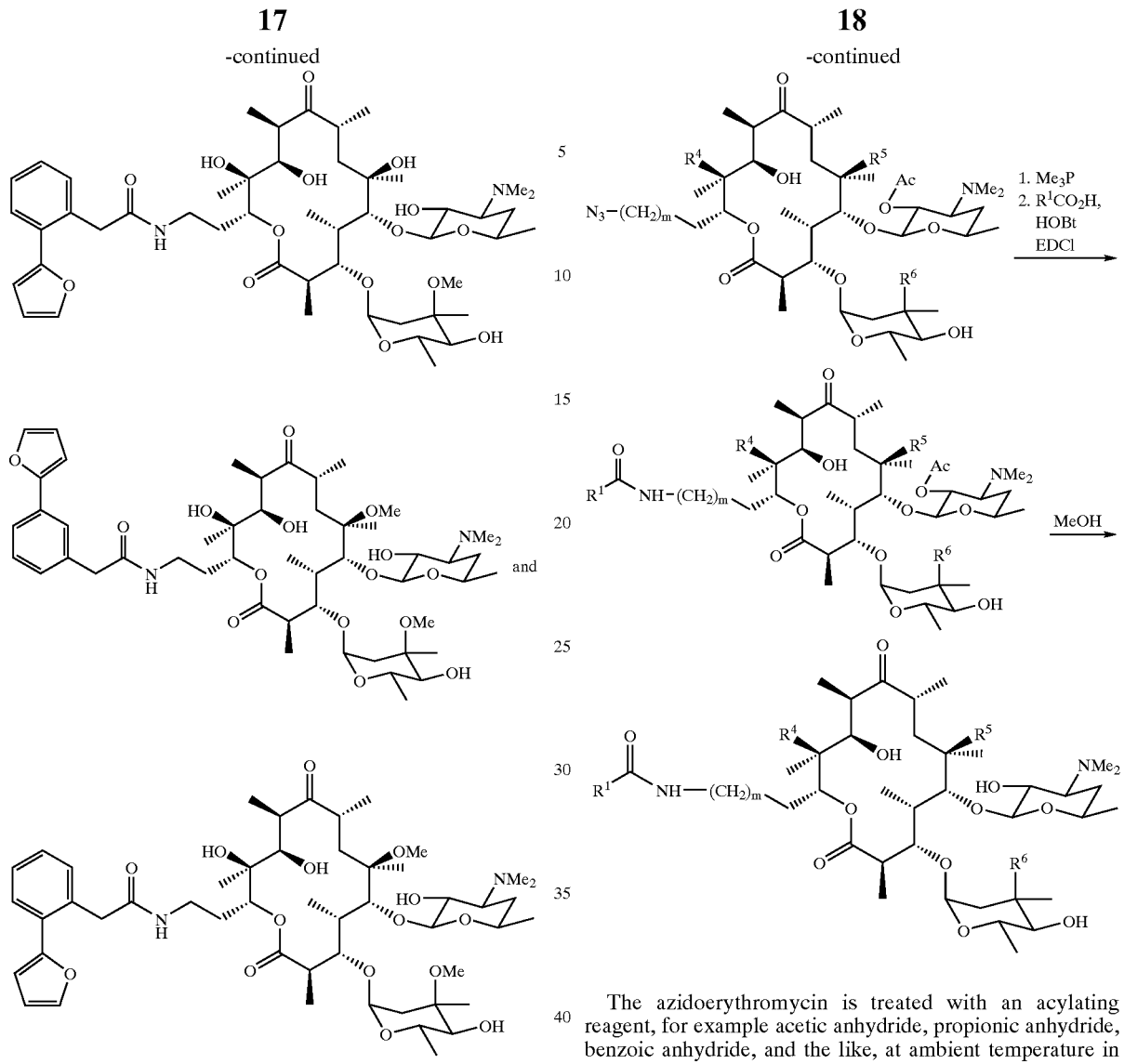

and are provided.

In another aspect of the invention, methods for the preparation of compounds of formula (I) are provided. In one embodiment of the invention, certain embodiments of the compounds of formula (I) wherein $R^2$=H are prepared from azidoerythromycins as illustrated in Scheme 1.

SCHEME 1

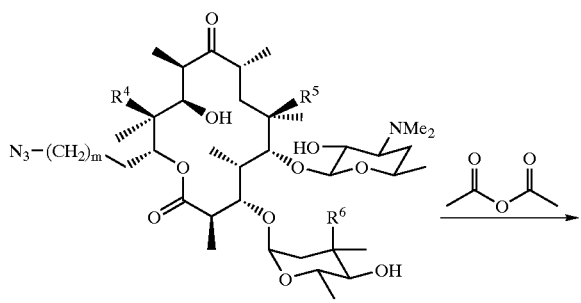

The azidoerythromycin is treated with an acylating reagent, for example acetic anhydride, propionic anhydride, benzoic anhydride, and the like, at ambient temperature in an inert solvent such as ethyl acetate, dichloromethane, or acetonitrile, to produce the 2'-O-acyl azidoerythromycin. This is detailed below in Example 5. The azide is then reduced using a phosphine such as trimethylphosphine or triphenylphosphine in a solvent such as tetrahydrofuran (THF) or a mixture of THF and dichloromethane, and the intermediate phosphinimine is reacted with a carboxylic acid, a carbodiimide such as 1-[3-(dimethylamino)propyl]-2-ethylcarbodiimide hydrochloride (EDCI) or dicyclohexyl-carbodiimide, and a coupling adjuvant such as 1-hydroxybenzotriazole (HOBt), N-hydroxysuccinimide (HOSu), or 1-hydroxy-7-azabenzotriazole (HABt), to produce the 2'-O-acyl-amidoerythromycin. A general procedure for this conversion is given below in Example 6. The 2'-O-acyl group is cleaved by heating in methanol, optionally in the presence of added triethylamine. Examples 7–45 below provide details of the preparation of compounds of formula (I) according to this method.

In another embodiment of the invention, the azidoerythromycin is treated with trimethylphosphine, and the resulting phosphinimine is reacted with a carboxylic acid and a coupling agent such as O-benzotriazol-1-yl-N,N,N',N'-tetramethyluronium hexafluorophosphate (HBTU), O-(7-azabenzotriazol-1-yl)-N,N,N',N'-tetramethyluronium hexafluorophosphate (HATU), or a similar coupling agent which incorporates the coupling agent and adjuvant into one molecule.

The carboxylic acids used in the preparation of the inventive compounds include alkanoic acids, alkenoic acids, alkynoic acids, N-protected amino acids and/or peptides such as N-BOC, N-Cbz, and N-FMOC amino acids and/or peptides, benzoic acids, heterocyclic carboxylic acids, biaryl carboxylic acids, arylacetic acids, biarylacetic acids, and the like, each of which may be substituted by a variety of groups.

In one embodiment of the invention, the carboxylic acids used in the preparation of the inventive compounds are biarylacetic acids. One means of preparing these biarylacetic acids is via a Suzuki coupling as illustrated in Scheme 2.

SCHEME 2

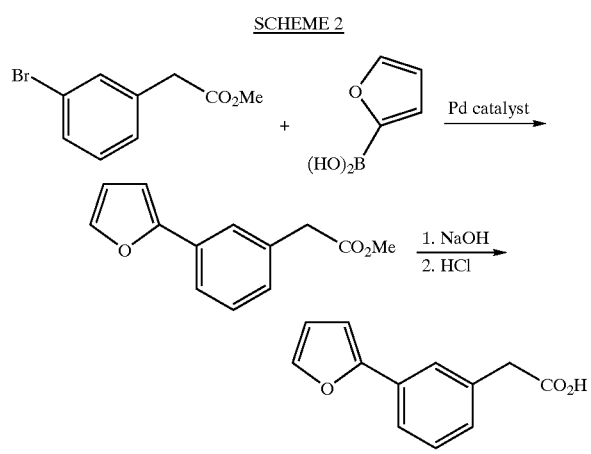

A haloarylacetic ester is coupled with an arylboronic acid in the presence of a palladium catalyst and base to provide the biarylacetic ester. The ester is subsequently saponified to provide the biarylacetic acid. Example 47 below provides a detailed procedure for this method as applied to the synthesis of 3-(2-furyl)phenylacetic acid. Suitable palladium catalysts include tetrakis(triphenylphosphine)palladium, palladium on carbon with triphenylphosphine, and similar sources of palladium(0). An alternate means of preparing these biarylacetic acids is through hydrolysis of the corresponding nitriles, prepared via Suzuki coupling of an arylboronic acid with a haloarylacetonitrile. The nitrile is hydrolyzed to the acid using a mixture of sodium hydroxide and hydrogen peroxide.

In another embodiment of the invention, certain embodiments of the compounds of formula (I) wherein $R^2$=alkyl, alkenyl, or alkynyl are prepared from azidoerythromycins as illustrated in Scheme 3.

SCHEME 3

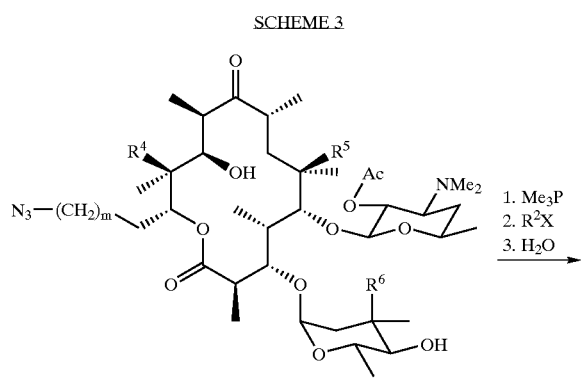

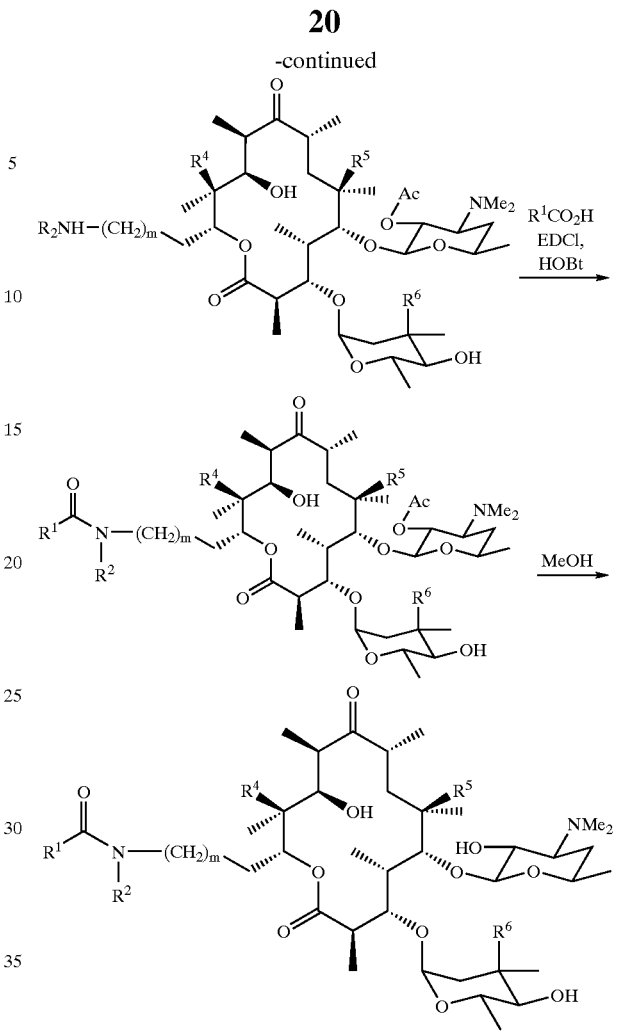

The 2'-O-acyl azidoerythromycin is reacted with trimethylphosphine to generate the phosphinimine, which is then alkylated by reaction with an alkyl halide or alkyl sulfonate, $R^2X$. Suitable alkylating agents include but are not limited to methyl iodide, methyl bromide, methyl triflate, ethyl tosylate, ethyl triflate, ethyl iodide, allyl bromide, and propargyl bromide. The resulting phosphonium salt is hydrolyzed, and the product amine is acylated with the carboxylic acid, $R^1COOH$, and a coupling reagent such as EDCI and HOBt, HATU, or the like, to provide a compound of formula (I) wherein $R^2$=alkyl, alkenyl, or alkynyl and $R^3$=alkanoyl or benzoyl. Removal of the 2'-O-acyl group by methanolysis provides the compound of formula (I) wherein $R^2$=alkyl alkenyl, or alkynyl and $R^3$=H.

In one aspect of the invention, methods for preparing azidoerythromycins are provided. In one embodiment of the invention, the method comprises the steps of (1) chemically synthesizing a racemic chlorinated diketide thioester; (2) growing a culture of a first organism in the presence of the racemic chlorinated diketide thioester so as to produce a chlorinated erythronolide; (3) partially purifying the chlorinated erythronolide; (4) chemically converting the chlorinated erythronolide into the azido erythronolide; (5) growing a culture of a second organism in the presence of the azido erythronolide, so as to produce an azidoerythromycin; and (6) purifying the azidoerythromycin.

In one embodiment of the invention, a method for preparing 15-azidoerythromycin is provided. This method comprises the steps of (1) chemically synthesizing racemic (2S*,3R*)-5-chloro-3-hydroxy-2-methylpentanoyl N-propionylcysteamine thioester; (2) growing a culture of a first organism in the presence of racemic (2S*,3R*)-5-chloro-3-hydroxy-2-methylpentanoyl N-propionylcysteamine thioester so as to produce 15-chloro-6-deoxyerythronolide B; (3) partially purifying the 15-chloro-6-deoxyerythronolide B so produced; (4) chemically converting the 15-chloro-6-deoxyerythronolide B into 15-azido-6-deoxyerythronolide B; (5) growing a culture of a second organism in the presence of the 15-azido-6-deoxyerythronolide B, so as to produce 15-azidoerythromycin; and (6) purifying the 15-azidoerythromycin.

In another embodiment of the invention, a method for preparing 14-azido-14-desmethylerythromycin is provided. This method comprises the steps of (1) chemically synthesizing racemic (2S*,3R*)-4-chloro-3-hydroxy-2-methylbutanoyl N-propionylcysteamine thioester; (2) growing a culture of a first organism in the presence of racemic (2S*,3R*)-4-chloro-3-hydroxy-2-methylbutanoyl N-propionylcysteamine thioester so as to produce 15-chloro-6-deoxyerythronolide B; (3) partially purifying the 14-chloro-14-desmethyl-6-deoxyerythronolide B so produced; (4) chemically converting the 14-chloro-14-desmethyl-6-deoxyerythronolide B into 14-azido-14-desmethyl-6-deoxyerythronolide B; (5) growing a culture of a second organism in the presence of the 14-azido-14-desmethyl-6-deoxyerythronolide B, so as to produce 14-azido-14-desmethylerythromycin A; and (6) purifying the 14-azido-14-desmethylerythromycin A.

In another embodiment of the invention, a method for preparing 15-(azidomethyl)-erythromycin is provided. This method comprises the steps of (1) chemically synthesizing racemic (2S*,3R*)-4-chloro-3-hydroxy-2-methylhexanoyl N-propionylcysteamine thioester; (2) growing a culture of a first organism in the presence of racemic (2S*,3R*)-4-chloro-3-hydroxy-2-methylhexanoyl N-propionylcysteamine thioester so as to produce 15-(chloromethyl)-6-deoxyerythronolide B; (3) partially purifying the 15-(chloromethyl)-6-deoxyerythronolide B so produced; (4) chemically converting the 15-(chloromethyl)-6-deoxyerythronolide B into 15-(azidomethyl)-6-deoxyerythronolide B; (5) growing a culture of a second organism in the presence of the 15-(azidomethyl)-6-deoxyerythronolide B, so as to produce 15-(azidomethyl)-erythromycin; and (6) purifying the 15-(azidomethyl)-erythromycin.

The synthesis of racemic thioesters is described in Ashley et al., "Synthesis of oligoketides," U.S. Pat. No. 6,492,562, incorporated herein by reference. In brief, the trichlorotitanium enolate of 3-propionyl-2-benzoxazolone is reacted with an aldehyde so as to produce the aldol adduct. The aldol adduct is converted into the thioester by reaction with the sodium salt of N-propionylcysteamine. This process is exemplified in detail in Example 1 below. When the aldehyde used is 3-chloropropanal, the thioester so produced is (2S*,3R*)-5-chloro-3-hydroxy-2-methylpentanoate N-propionylcysteamine thioester. When the aldehyde used is chloroacetaldehyde, the thioester so produced is (2S*,3R*)-4-chloro-3-hydroxy-2-methylbutanoate N-propionylcysteamine thioester. When the aldehyde used is 4-chlorobutyraldehyde, the thioester so produced is (2S*, 3R*)-6-chloro-3-hydroxy-2-methylhexanoate N-propionylcysteamine thioester.

The preparation of 13-substituted 6-deoxyerythronolide B compounds is described in Khosla et al., U.S. Pat. Nos. 6,080,555, 6,274,560, 6,066,721, and 6,261,816; and Ashley et al., U.S. Pat. No. 6,492,562; each of which is incorporated herein by reference. In one embodiment, 15-chloro-6-deoxyerythronolide B is prepared by a method in which racemic (2S*,3R*)-5-chloro-3-hydroxy-2-methylpentanoyl N-propionylcysteamine thioester is provided to a 6-deoxyerythronolide B synthase ("DEBS") that is unable to act on its natural substrate, propionyl CoA, due to a mutation in the ketosynthase domain of module 1 of DEBS. This recombinant DEBS can be expressed in the natural host that normally produces erythromycin, *Saccharopolyspora erythraea*, or the entire PKS gene cluster can be inserted by plasmid in a suitable host such as *S. coelicolor* (see e.g., Jacobsen et al, Science 277:367–369 (1997), incorporated herein by reference) or *S. lividans* which has been modified to delete its endogenous actinorhodin polyketide synthesis mechanism. In a preferred embodiment, the host is *S. coelicolor* CH999/pJRJ2, which expresses a mutant 6-DEB synthase having an inactivated module 1 ketosynthase.

A cell free system as described in Khosla et al., "Synthesis of polyketides from diketides," U.S. Pat. No. 6,080,555; Khosla et al., "Cell-free synthesis of polyketides," U.S. Pat. No. 6,274,560; and PCT Publication No. WO 9702358, each of which is incorporated herein by reference, may also be employed by producing the relevant PKS proteins recombinantly and effecting their secretion or lysing the cells containing them. A typical cell-free system would include the appropriate PKS, NADPH and an appropriate buffer and substrates required for the catalytic synthesis of polyketides.

In another embodiment of the invention, the appropriate thioester diketide substrates are provided to PKS enzymes other than the 6-dEB synthase of *Saccharopolyspora erythraea*. Other PKS enzymes include the 6-dEB synthase of *Micromonospora megalomicea* and its KS1° derivative described in McDaniel & Volchegursky, "Recombinant megalomicin biosynthetic genes," PCT publication WO 01/27284; the oleandolide PKS and its KS1° derivative described in Betlach et al., "Recombinant oleandolide polyketide synthase," U.S. Pat. No. 6,251,636; and the narbonolide PKS and its KS1° derivative described in McDaniel et al., "Heterologous expression of narbonolide PKS," U.S. Pat. No. 6,503,741 and in Betlach et al., "Nucleic acids encoding narbonolide polyketide synthase enzymes from streptomyces narbonensis," U.S. Pat. No. 6,303,767; each of which is incorporated herein by reference.

In another embodiment of the invention, the appropriate thioester diketide substrates are provided to any of the above PKS enzymes in a host cell that is capable of performing one or more of the post-PKS hydroxylation and/or glycosylation steps leading to the erythromycins. Thus, a chlorinated erythronolide B is prepared by providing a chlorinated thioester diketide to a strain comprising both DEBS and a 6-hydroxylase, for example the eryF hydroxylase from *Sac. erythraea*. The production of 14-chloro-14-desmethylerythronolide B is described in Example 72 below.

The preparation of 15-chloro-6-deoxyerythronolide B is detailed in Example 2 below. Using the same methods but starting with the appropriate diketide thioesters described above, 14-chloro-14-desmethyl-6-deoxyerythronolide B and 15-(chloromethyl)-6-deoxyerythronolide B are prepared as described below in Examples 71 and 73.

In one embodiment of the invention, the chlorinated erythronolide so produced is reacted with sodium azide and sodium iodide in DMSO so as to produce the azido erythronolide by displacement of the chloride with azide. This is detailed in the Examples below. Thus, 15-azido-6-deoxyerythronolide B is prepared from 15-chloro-6-deoxyerythronolide B (Example 3), 14-azido-14-desmethyl-6-deoxyerythronolide B is prepared from 14-chloro-14-desmethyl-6-deoxyerythronolide B (Example 74), 15-(azidomethyl)-6-deoxyerythronolide B is prepared from 15-(chloromethyl)-6-deoxyerythronolide B (Example 75), 15-azido-erythronolide B is prepared from 15-chloro-erythronolide B, 14-azido-14-desmethyl-erythronolide B is prepared from 14-chloro-14-desmethyl-erythronolide B, and 15-(azidomethyl)-erythronolide B is prepared from 15-(chloromethyl)-erythronolide B.

In another embodiment of the invention, the azidoerythronolide prepared according to one of the above methods is then added to a culture of a bioconversion organism capable of glycosylating at the C-3 and C-5 positions, and optionally hydroxylating at C-6, hydroxylating at the C-12 position and/or methylating a 3-O-mycarosyl group, depending on the strain and fermentation conditions employed. In a preferred embodiment, the bioconversion organism is *Saccharopolyspora erythraea* K39-14V, a strain in which the module 1 ketosynthase of the native DEBS genes has been inactivated as described in Santi et al., "Hosts for the biosynthesis of polyketides," PCT publication WO 01/83803, incorporated herein by reference. K39-14V contains the enzyme activities needed to convert an erythronolide into the erythromycin A derivative, i.e., hydroxylation at C-6, addition of mycarose to the 3-OH, addition of desosamine to the 5-OH, hydroxylation at C-12, and methylation of the mycarose. In one embodiment of the invention, K39-14V is supplied with 15-azido-6-deoxyerythronolide B under fermentation conditions wherein 15-azidoerythromycin A is the predominant product. This is detailed below in Example 4. In another embodiment of the invention, K39-14V is supplied with 15-azido-6-deoxyerythronolide B under fermentation conditions wherein 15-azidoerythromycin B is the predominant product, for example under conditions of limited oxygen. In another embodiment of the invention, K39-14V is supplied with 14-azido-14-desmethyl-6-deoxyerythronolide B under fermentation conditions wherein 14-azido-14-desmethylerythromycin A is produced. In another embodiment of the invention, K39-14V is supplied with 14-azido-14-desmethyl-6-deoxyerythronolide B under fermentation conditions wherein 14-azido-14-desmethylerythromycin B is produced (Example 76). In another embodiment of the invention, K39-14V is supplied with 15-(azidomethyl)-6-deoxyerythronolide B under fermentation conditions wherein 15-(azidomethyl)-erythromycin A is produced. In another embodiment of the invention, K39-14V is supplied with 15-(azidomethyl)-6-deoxyerythronolide B under fermentation conditions wherein 15-(azidomethyl)-erythromycin B is produced (Example 77). In another embodiment of the invention, a bioconversion strain that lacks an active 12-hydroxylase, encoded by the eryK gene or a homologue, is used to convert the azido-6-deoxyerythromycin into the azidoerythromycin B. In another embodiment of the invention, the azidoerythromycin B compounds are produced using a mutant of K39-14V wherein the eryK gene encoding the 12-hydroxylase has been inactivated or deleted.

The resulting azidoerythromycins are isolated as described for 15-azidoerythromycin A in Example 4 below. The cells are removed from the fermentation by centrifugation, and the broth is extracted to remove the azidoerythromycins. In one embodiment of the invention, the extraction is performed using absorption onto a solid resin, such as XAD or HP20. The azidoerythromycins are subsequently eluted from the resin with an organic solvent such as methanol, ethanol, acetone, acetonitrile, or ethyl acetate. In another embodiment of the invention, the extraction is performed by mixing the broth with an immiscible organic solvent in which the azidoerythromycin is soluble, such as ethyl acetate, dichloromethane, or chloroform. After concentration of the extract, the residue is subjected to chromatography to provide purified azidoerythromycins.

In another embodiment of the invention, compounds of formula (I) wherein $R^5$=alkoxy are provided. In one embodiment, these compounds are prepared from azidoerythromycins as illustrated in Scheme 4 and exemplified in Example 80. The azidoerythromycin is first treated with hydroxylamine, typically in the presence of an acid catalyst such as acetic acid and in a mixture of water and isopropanol as solvent, to produce the 9-oxime. This procedure is exemplified in detail with 15-azidoerythromycin A in Example 48 below. The 9-oxime is protected, for example using an acetal such as 1,1-diisopropoxycyclohexane (DIPCH) or 2,2-dimethoxypropane in the presence of a mild acid catalyst such as pyridinium p-toluenesulfonate (PPTS). This procedure is exemplified in detail with 15-azidoerythromycin A 9-oxime in Example 49 below. Other protecting groups, such as trialkylsilyl ethers, can also be used to protect the 9-oxime. The 2'- and 4"-OH groups are next protected, for example as trimethylsilyl ethers by treatment with a mixture of trimethylsilylimidazole and chlorotrimethylsilane, as described below in Example 50.

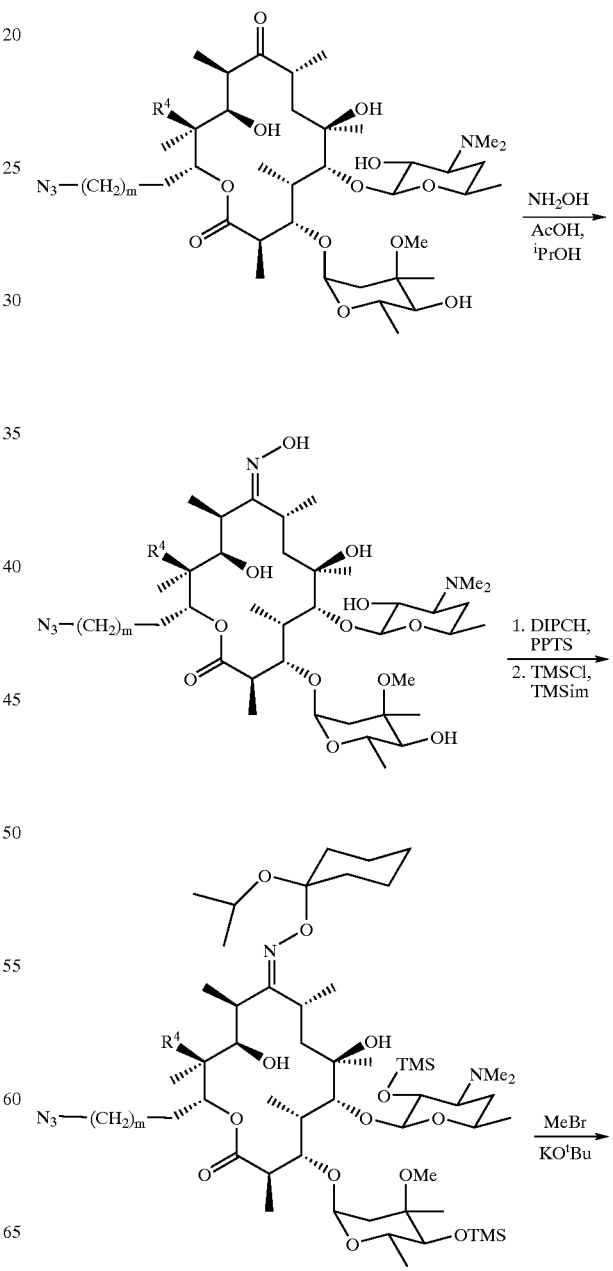

SCHEME 4

-continued

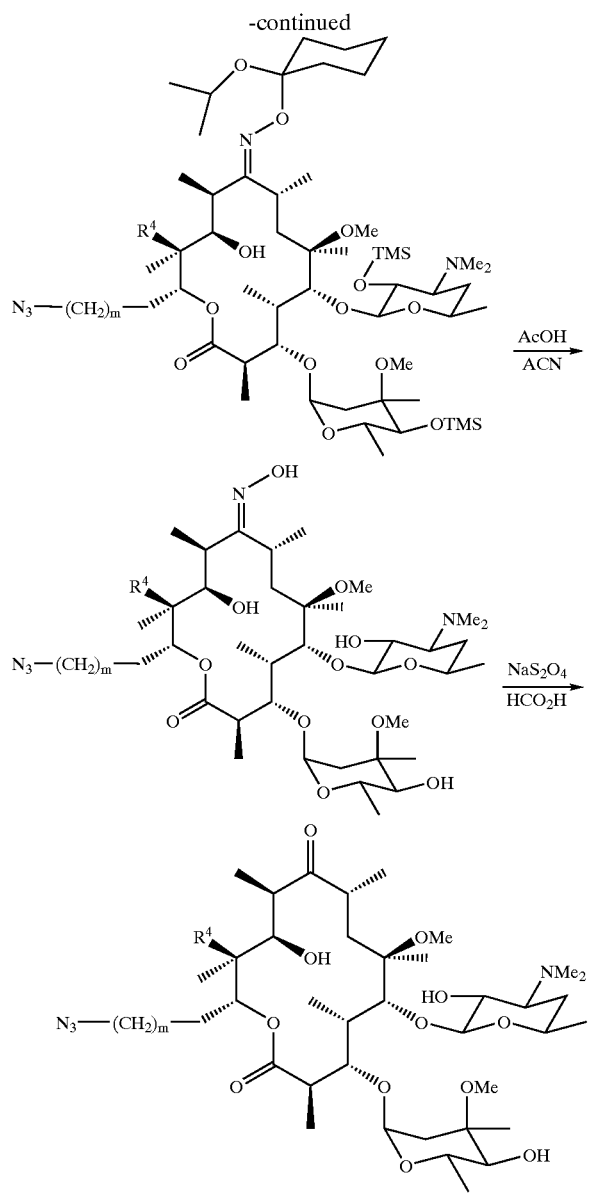

In one embodiment of the invention, the 6-OH is methylated using methyl bromide in the presence of potassium tert-butoxide or similar base to provide embodiments of the compounds of formula (I) wherein $R^5$=OMe. This process is exemplified below in Example 51. In another embodiment of the invention, the 6-OH is allylated using allyl bromide in the presence of potassium tert-butoxide or similar base to provide embodiments of the compounds of formula (I) wherein $R^5$=O-allyl. In another embodiment of the invention, the 6-OH is allylated using allyl tert-butyl carbonate in the presence of a palladium catalyst, for example palladium acetate and triphenylphosphine, to provide embodiments of the compounds of formula (I) wherein $R^5$=O-allyl.

The 9-oxime and 2'- and 4"-OH groups are deprotected by treatment with acetic acid in acetonitrile. The 9-oxime can be cleaved, for example using sodium hydrosulfite and formic acid, to provide embodiments of compounds of formula (I) wherein $R^5$=alkoxy. These steps are exemplified below in Examples 52 and 53.

In another aspect of the invention, compounds of formula (II) are provided

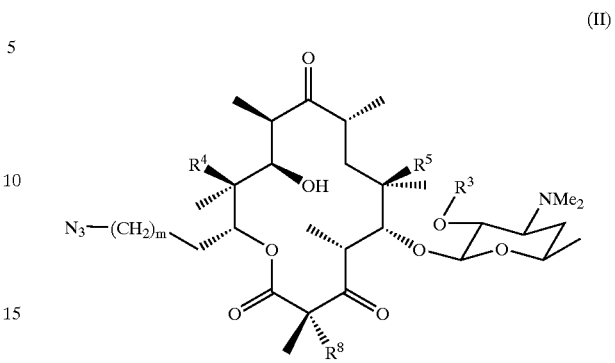

wherein $R^3$, $R^4$, and m are as defined above; $R^5$ is H, $C_1$–$C_4$ alkoxy, $C_2$–$C_4$ alkenyloxy, or $C_2$–$C_4$ alkynyloxy; and $R^8$ is H or F.

In one embodiment of the invention, compounds of formula (II) wherein m=0 are provided.

In another embodiment of the invention, compounds of formula (II) wherein m=1 are provided.

In another embodiment of the invention, compounds of formula (II) wherein m=2 are provided.

In one embodiment of the invention, the compounds of formula (II) wherein $R^4$=OH, $R^5$=$C_1$–$C_4$ alkoxy, and m=0 are provided.

In another embodiment of the invention, the compounds of formula (II) wherein $R^4$=OH, $R^5$=$C_1$–$C_4$ alkoxy, and m=1 are provided.

In another embodiment of the invention, the compounds of formula (II) wherein $R^4$=OH, $R^5$=$C_1$–$C_4$ alkoxy, and m=2 are provided.

In another embodiment of the invention, the compound of formula (II) wherein $R^4$=H, $R^5$=$C_1$–$C_4$ alkoxy, and m=0 are provided.

In another embodiment of the invention, the compound of formula (II) wherein $R^4$=H, $R^5$=$C_1$–$C_4$ alkoxy, and m=1 are provided.

In another embodiment of the invention, the compound of formula (II) wherein $R^4$=H, $R^5$=$C_1$–$C_4$ alkoxy, and m=2 are provided.

In another embodiment of the invention, the compounds of formula (II) wherein $R^3$=acetyl or benzoyl, $R^4$=OH, $R^5$=$C_1$–$C_4$ alkoxy, and m=0 are provided.

In another embodiment of the invention, the compounds of formula (II) wherein $R^3$=acetyl or benzoyl, $R^4$=OH, $R^5$=$C_1$–$C_4$ alkoxy, and m=1 are provided.

In another embodiment of the invention, the compounds of formula (II) wherein $R^3$=acetyl or benzoyl, $R^4$=OH, $R^5$=$C_1$–$C_4$ alkoxy, and m=2 are provided.

In another embodiment of the invention, the compounds of formula (II) wherein $R^3$=acetyl or benzoyl, $R^4$=H, $R^5$=$C_1$–$C_4$ alkoxy, and m=0 are provided.

In another embodiment of the invention, the compounds of formula (II) wherein $R^3$=acetyl or benzoyl, $R^4$=H, $R^5$=$C_1$–$C_4$ alkoxy, and m=1 are provided.

In another embodiment of the invention, the compounds of formula (II) wherein $R^3$=acetyl or benzoyl, $R^4$=H, $R^5$=$C_1$–$C_4$ alkoxy, and m=2 are provided.

In another embodiment of the invention, the compounds of formula (II) having the formulas

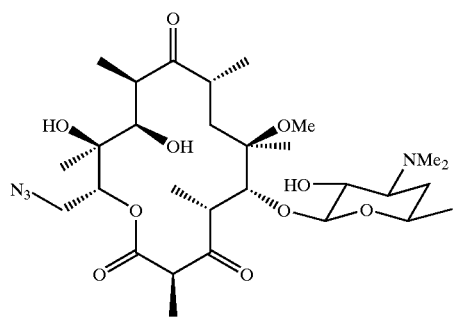
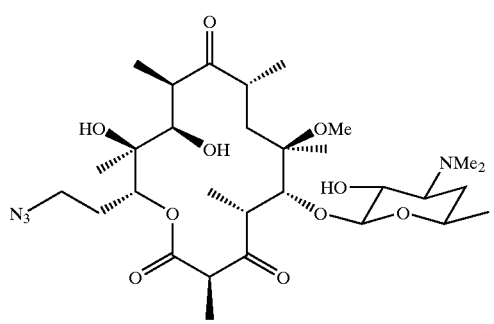
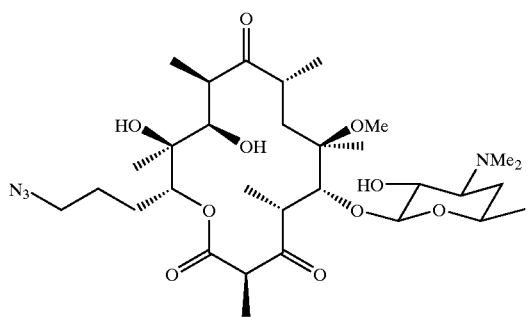
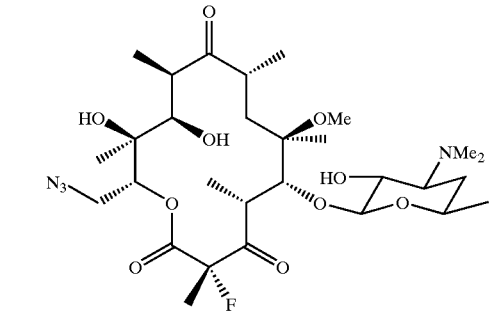
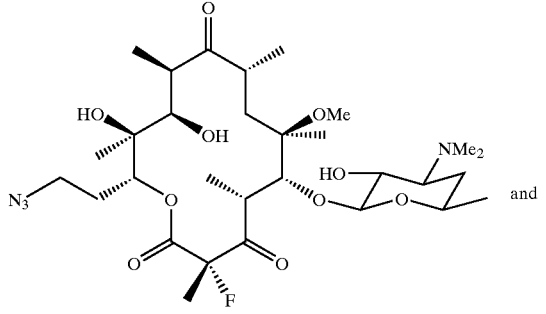 and
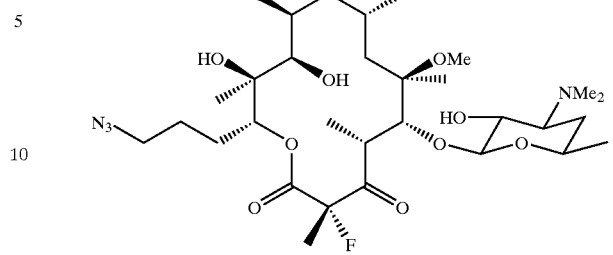
are provided.
In another aspect of the invention, methods for the preparation of compounds of formula (II) are provided. In one embodiment of the invention, certain embodiments of the compounds of formula (II) are prepared from compounds of formula (I) wherein $R^5$=alkoxy as illustrated in Scheme 5.
SCHEME 5
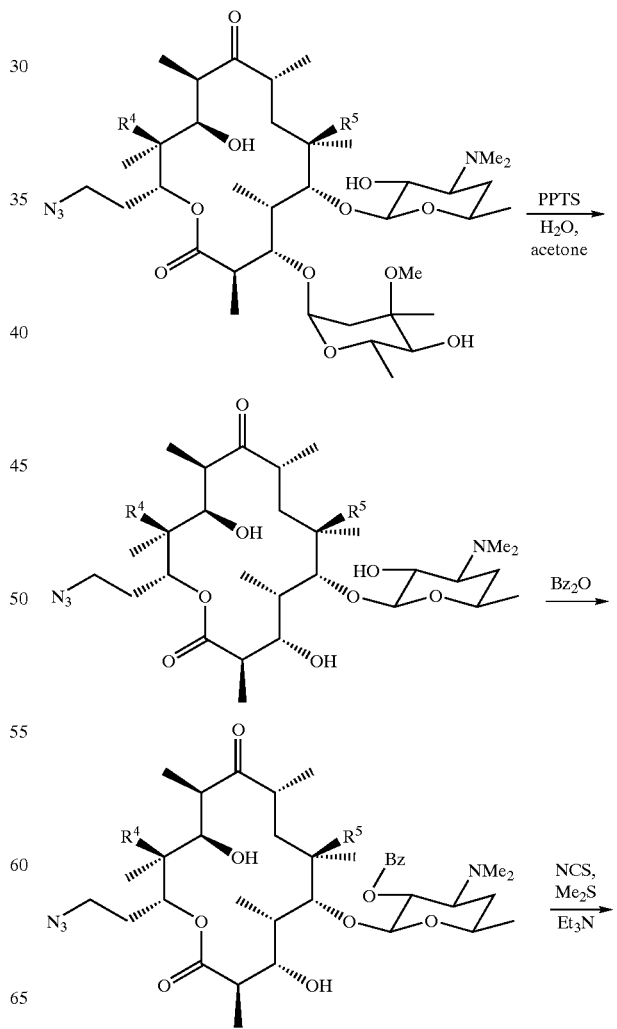

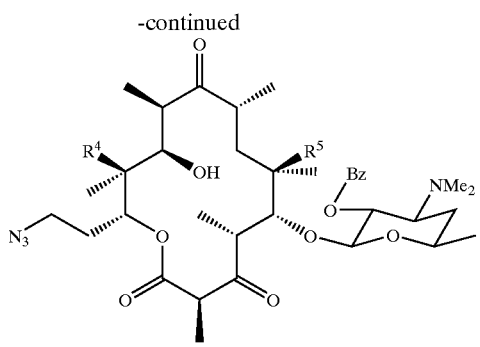

The cladinose is removed from the compound of formula (I) by treatment with a mild acid in the presence of water, for example using PPTS in a mixture of acetone and water as exemplified below in Example 54, or using aqueous HCl. After protection of the 2'-OH by treatment with benzoic anhydride in the absence of additional base (Example 55), the 3-OH is oxidized to the ketone (Example 56). Suitable oxidation methods include but are not limited to the Corey-Kim (N-chlorosuccinimide, dimethylsulfide, triethylamine), Swern (oxalyl chloride, DMSO, triethylamine), Moffat (dicyclohexylcarbodiimide, DMSO), and modified Pfizer-Moffat (1-[3-(dimethylamino)propyl]-3-ethylcarbodiimide, pyridinium trifluoroacetate, DMSO) conditions.

In another embodiment of the invention, compounds of formula (II) wherein $R^8$=F are prepared from compounds of formula (II) wherein $R^8$=H as illustrated in Scheme 6. The compound of formula (II) wherein $R^8$=H is treated with a base, for example potassium tert-butoxide, and a fluorinating agent such as N-fluorobenzenesulfonimide (NFBS) to yield the compound of formula (II) wherein $R^8$=F. A representative method for fluorination in given in Example 60.

SCHEME 6

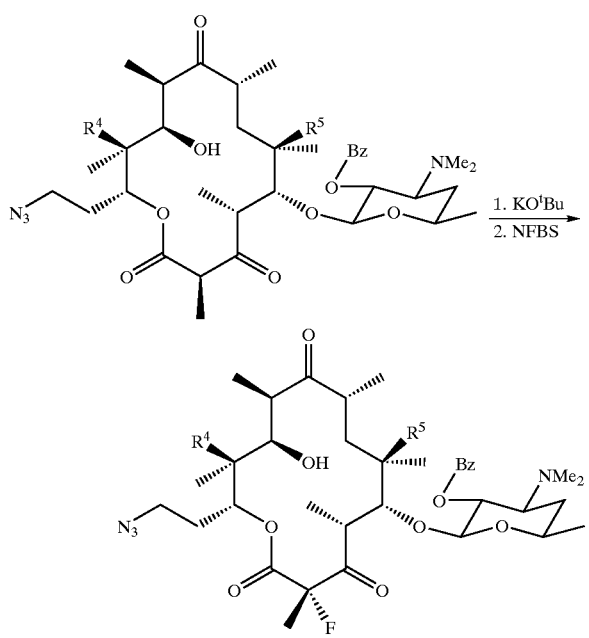

In another embodiment of the invention, the 2'-O-benzoyl protecting group is removed from the compound of formula (II) wherein $R^3$=benzoyl by heating in methanol containing triethylamine to provide the compound of formula (II) wherein $R^3$=H.

In another aspect of the invention, compounds of formula (III) are provided

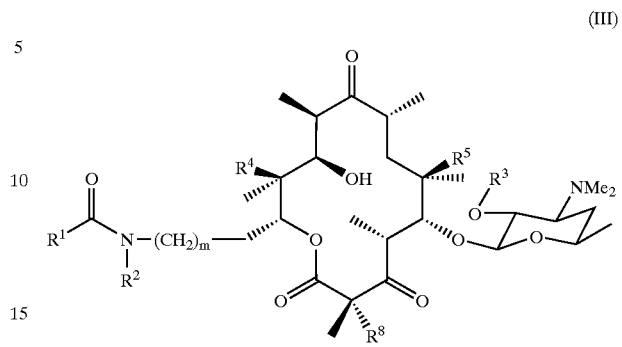

(III)

wherein $R^1$, $R^2$, $R^3$, $R^4$, $R^8$, and m are as defined above and $R^5$ is H, $C_1$–$C_4$ alkoxy, $C_2$–$C_4$ alkenyloxy, or $C_2$–$C_4$ alkynyloxy.

In one embodiment of the invention, compounds of formula (II) are provided wherein $R^1$ is $C_6$–$C_{15}$ substituted or unsubstituted arylalkyl, $C_6$–$C_{15}$ substituted or unsubstituted biarylalkyl, $C_6$–$C_{15}$ substituted or unsubstituted arylalkenyl, or $C_6$–$C_{15}$ substituted or unsubstituted arylalkynyl.

In one embodiment of the invention, compounds of formula (III) wherein $R_2$ is H and $R^5$ is alkoxy are provided.

In another embodiment of the invention, compounds of formula (III) are provided wherein $R^1$ is $C_4$–$C_{15}$ substituted or unsubstituted aryl, $C_5$–$C_{20}$ substituted or unsubstituted arylalkyl, or $C_5$–$C_{20}$ substituted or unsubstituted biarylalkyl; $R^2$ is H; and $R^5$ is alkoxy.

In another embodiment of the invention, compounds of formula (III) are provided wherein m=0.

In another embodiment of the invention, compounds of formula (III) are provided wherein m=1.

In another embodiment of the invention, compounds of formula (III) are provided wherein m=2.

In another embodiment of the invention, compounds of formula (III) are provided wherein $R^2$ is H; $R^3$ is acetyl or benzoyl; $R^4$ is H or OH; $R^5$ is alkoxy; and m=0.

In another embodiment of the invention, compounds of formula (III) are provided wherein $R^2$ is H; $R^3$ is acetyl or benzoyl; $R^4$ is H or OH; $R^5$ is alkoxy; and m=1.

In another embodiment of the invention, compounds of formula (III) are provided wherein $R^2$ is H; $R^3$ is acetyl or benzoyl; $R^4$ is H or OH; $R^5$ is alkoxy; and m=2.

In another embodiment of the invention, compounds of formula (III) are provided wherein $R^2$ is H; $R^3$ is H; $R^4$ is H or OH; $R^5$ is alkoxy; and m=0.

In another embodiment of the invention, compounds of formula (III) are provided wherein $R^2$ is H; $R^3$ is H; $R^4$ is H or OH; $R^5$ is alkoxy; and m=1.

In another embodiment of the invention, compounds of formula (III) are provided wherein $R^2$ is H; $R^3$ is H; $R^4$ is H or OH; $R^5$ is alkoxy; and m=2.

In another embodiment of the invention, compounds of formula (III) having the structures

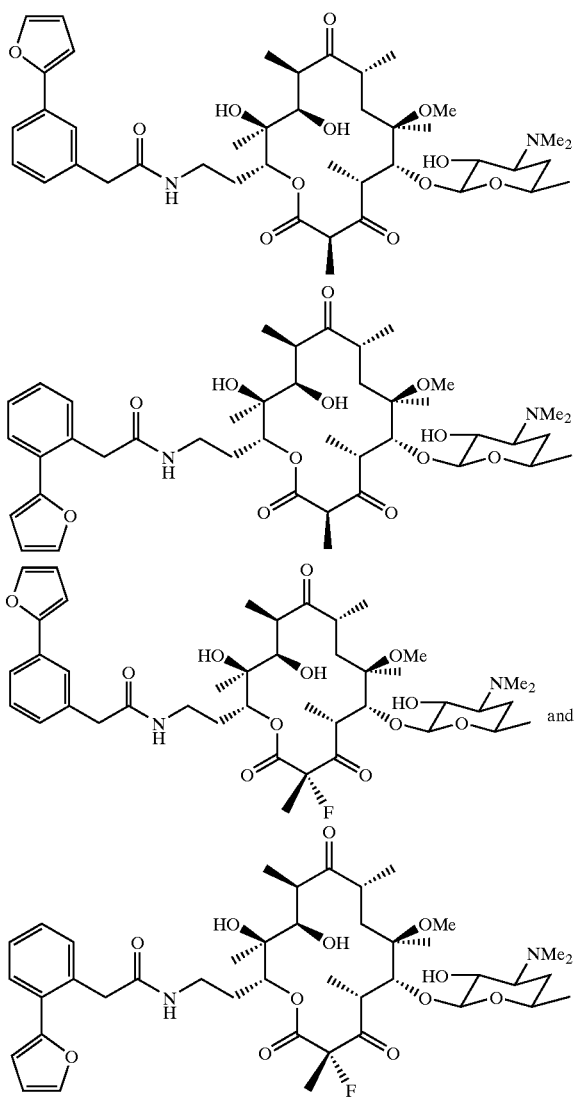

are provided.

In another aspect of the invention, methods for the preparation of compounds of formula (III) are provided. In one embodiment of the invention, compounds of formula (III) are prepared from compounds of formula (II) wherein $R^3$=benzoyl as illustrated in Scheme 7.

SCHEME 7

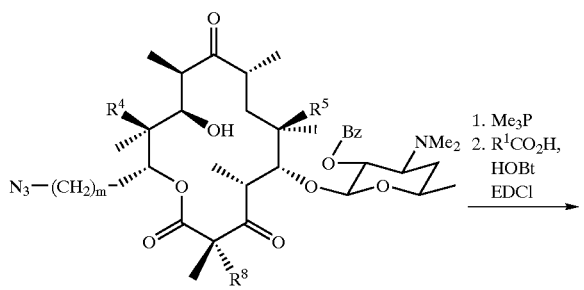

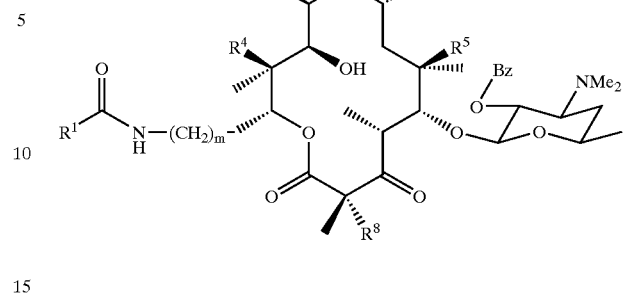

The compound of formula (II) is treated with trimethylphosphine, and the resulting phosphinimine is reacted with a carboxylic acid, a coupling agent such as a carbodiimide, and a coupling adjuvant such as HOBt, HABt, or HOSu as discussed above and exemplified below in Example 65.

In another embodiment of the invention, the compound of formula (II) is treated with trimethylphosphine, and the resulting phosphinimine is reacted with a carboxylic acid and a coupling agent such as O-benzotriazol-1-yl-N,N,N',N'-tetramethyluronium hexafluorophosphate (HBTU), O-(7-azabenzotriazol-1-yl)-N,N,N',N'-tetramethyluronium hexafluorophosphate (HATU), or a similar coupling agent which incorporates the coupling agent and adjuvant into one molecule.

In another embodiment of the invention, the 2'-O-benzoyl protecting group is removed from the compound of formula (III) wherein $R^3$=benzoyl by heating in methanol optionally containing triethylamine to provide the compound of formula (III) wherein $R^3$=H. This is exemplified below in Example 66.

In another embodiment of the invention, certain embodiments of the compounds of formula (III) wherein $R^2$=alkyl, alkenyl, or alkynyl are prepared from compounds of formula (II) as illustrated in Scheme 8. The compound of formula (II) wherein $R^3$=alkanoyl or benzoyl is reacted with trimethylphosphine to generate the phosphinimine, which is then alkylated by reaction with an alkyl halide or alkyl sulfonate, $R^2X$. Suitable alkylating agents include but are not limited to methyl iodide, methyl bromide, methyl triflate, ethyl tosylate, ethyl triflate, ethyl iodide, allyl bromide, and propargyl bromide.

SCHEME 8

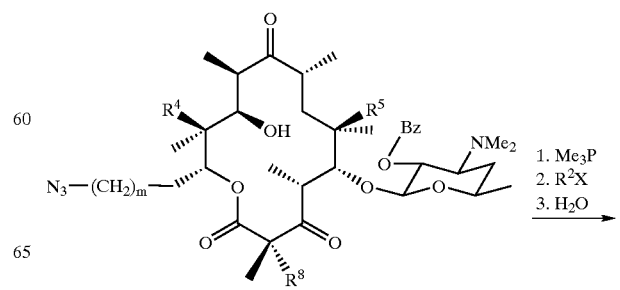

-continued

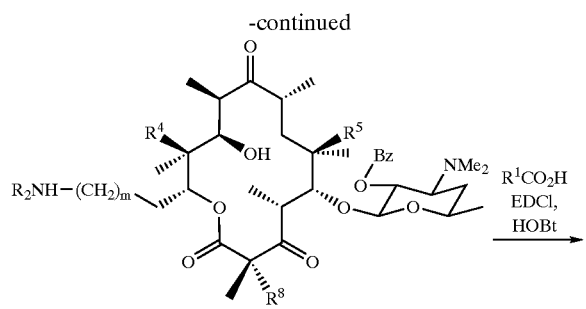

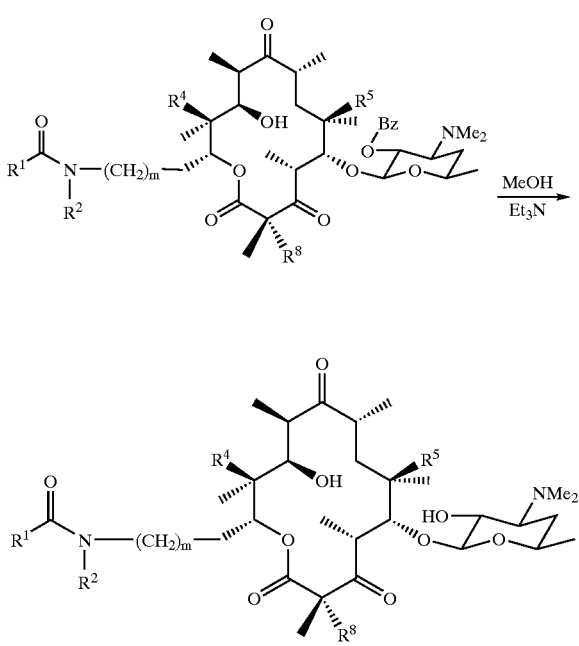

The resulting phosphonium salt is hydrolyzed, and the product a amine is acylated with the carboxylic acid, $R^1COOH$, and a coupling reagent such as EDCI and HOBt, HATU, or the like, to provide a compound of formula (III) wherein $R^2$=alkyl, alkenyl, or alkynyl and $R^3$=alkanoyl or benzoyl. Removal of the 2'-O-acyl group by methanolysis provides the compound of formula (III) wherein $R^2$=alkyl, alkenyl, or alkynyl and $R^3$=H.

In another aspect of the invention, compounds of formula (IV) are provided

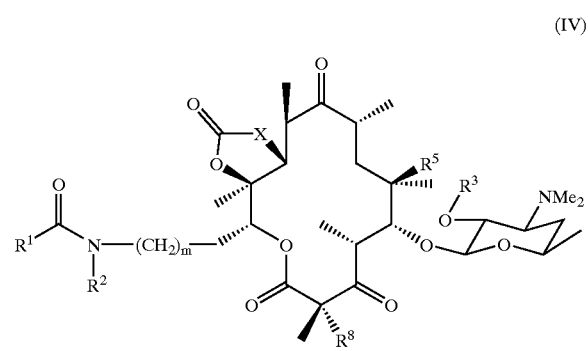

wherein $R^1$, $R^2$, $R^3$, $R^8$, and m are as defined above and $R^5$ is H, $C_1$–$C_4$ alkoxy, $C_2$–$C_4$ alkenyloxy, or $C_2$–$C_4$ alkynyloxy, and X is O or $NR^7$, wherein $R^7$ is H, $C_1$–$C_4$ alkyl, or $C_6$–$C_{20}$ arylalkyl.

In one embodiment of the invention, compounds of formula (IV) are provided wherein $R^1$ is $C_6$–$C_{15}$ substituted or unsubstituted arylalkyl, $C_6$–$C_{15}$ substituted or unsubstituted biarylalkyl, $C_6$–$C_{15}$ substituted or unsubstituted arylalkenyl, or $C_6$–$C_{15}$ substituted or unsubstituted arylalkynyl.

In another embodiment of the invention, compounds of formula (IV) are provided wherein m=0.

In another embodiment of the invention, compounds of formula (IV) are provided wherein m=1.

In another embodiment of the invention, compounds of formula (IV) are provided wherein m=2.

In another embodiment of the invention, compounds of formula (IV) are provided wherein $R^2$=H.

In one embodiment of the invention, compounds of formula (IV) are provided wherein $R^2$=H; $R^3$=H; $R^5$=OMe; X=O; and m=0.

In another embodiment of the invention, compounds of formula (IV) are provided wherein $R^2$=H; $R^3$=H; $R^5$=OMe; X=O; and m=1.

In another embodiment of the invention, compounds of formula (IV) are provided wherein $R^2$=H; $R^3$=H; $R^5$=OMe; X=O; and m=2.

In another embodiment of the invention, compounds of formula (IV) are provided wherein $R^2$=H; $R^3$=H; $R^5$=OMe; X=NH; and m=0.

In another embodiment of the invention, compounds of formula (IV) are provided wherein $R^2$=H; $R^3$=H; $R^5$=OMe; X=NH; and m=1.

In another embodiment of the invention, compounds of formula (IV) are provided wherein $R^2$=H; $R^3$=H; $R^5$=OMe; X=NH; and m=2.

In another embodiment of the invention, compounds of formula (IV) are provided wherein $R^1$ is $C_6$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; and $R^2$ is H.

In another embodiment of the invention, compounds of formula (IV) are provided wherein $R^1$ is $C_6$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; $R^2$ is H; and X is NH.

In another embodiment of the invention, compounds of formula (IV) having the structures

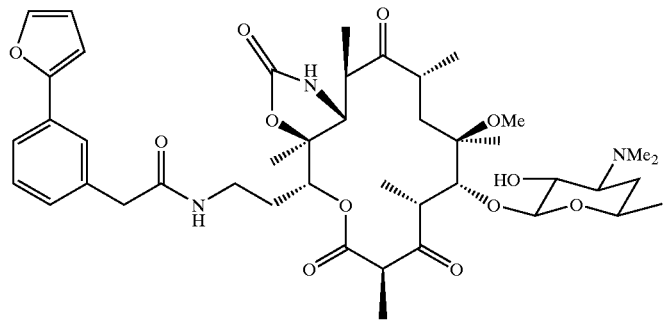
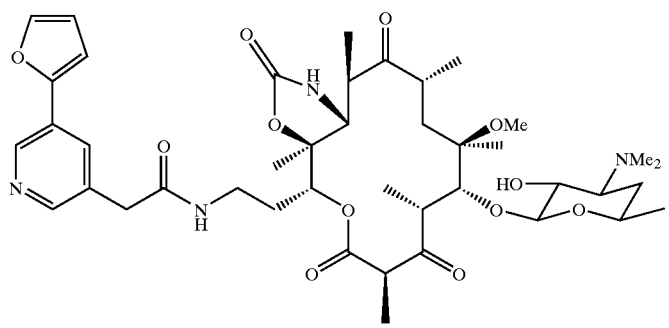
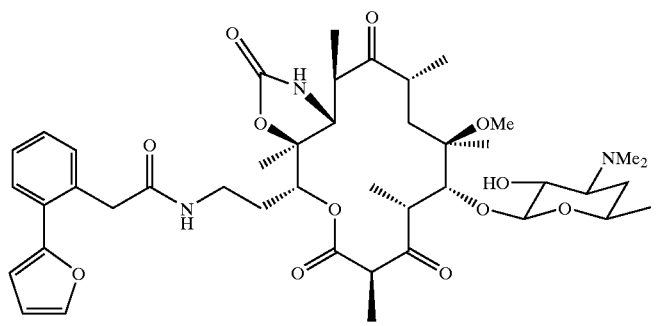
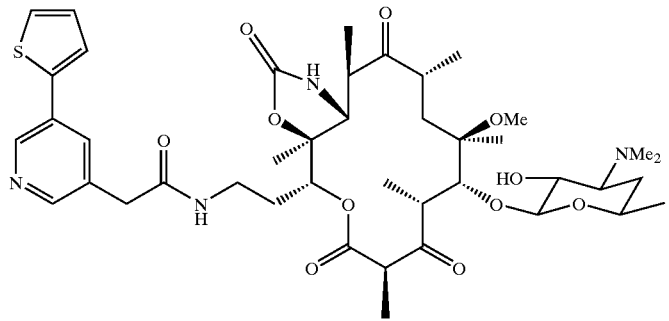
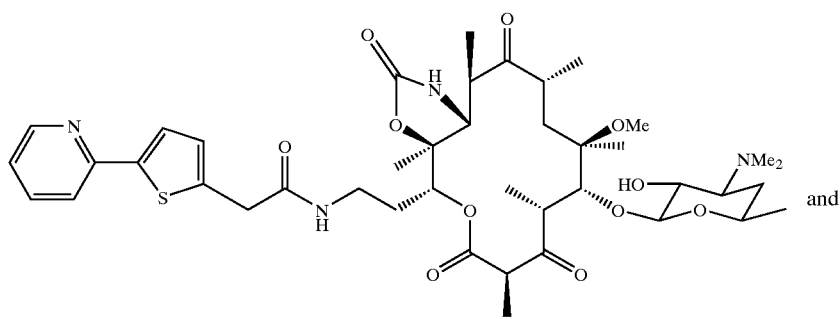

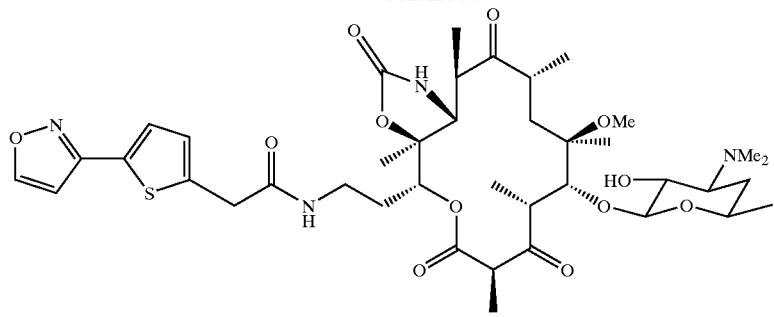
15
are provided.
In another embodiment of the invention, compounds of formula (IV) having the structures are provided:
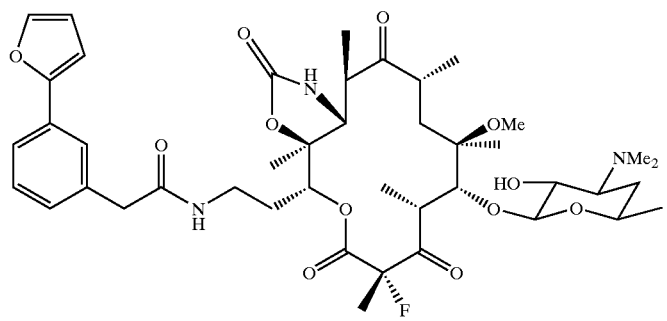
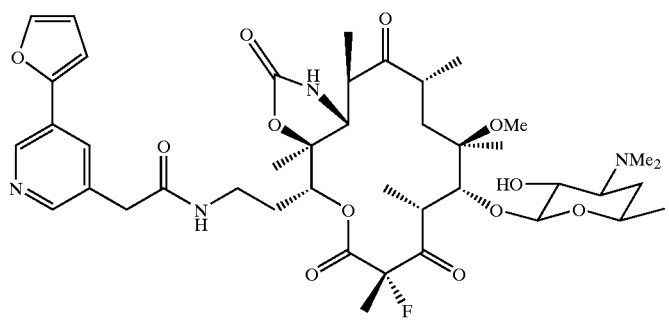
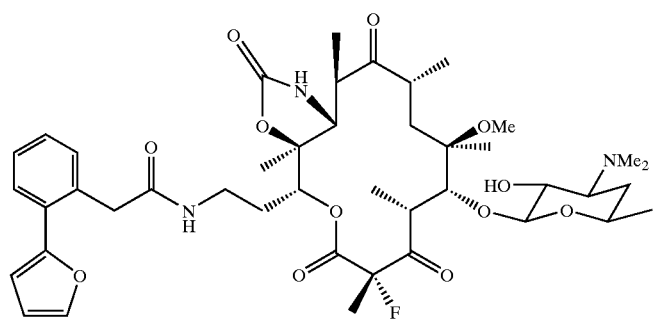

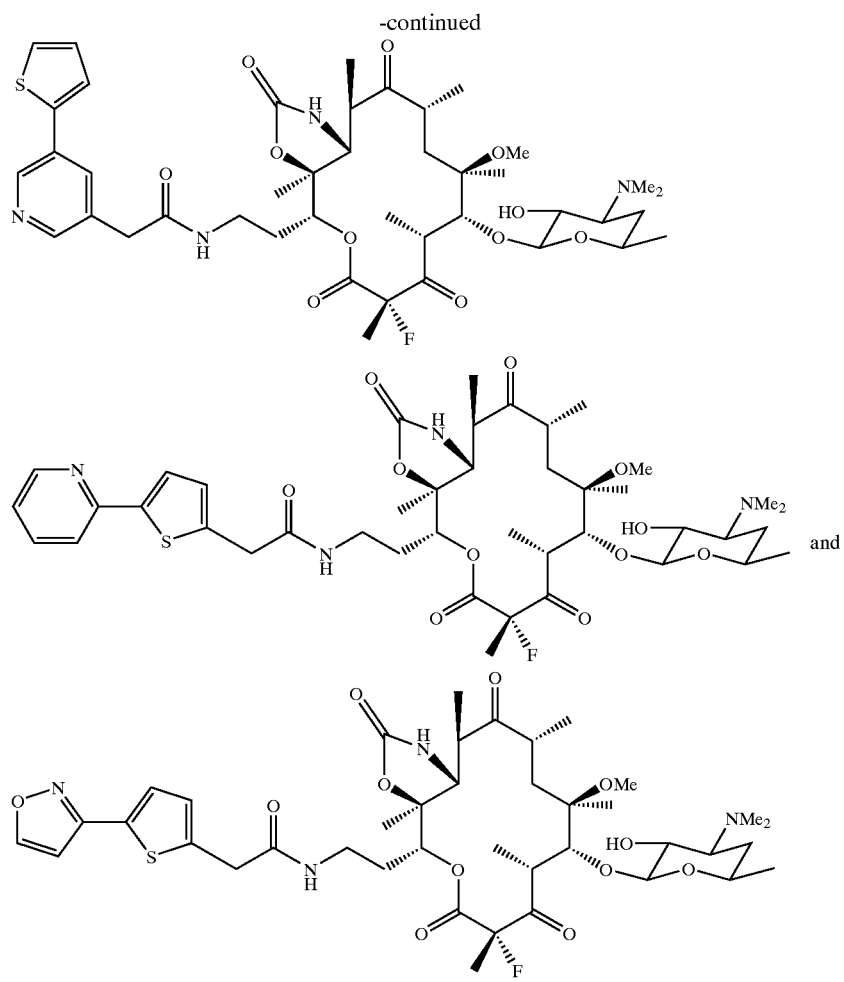

In another embodiment of the invention, compounds of formula (IV) having the structures are also provided:

In another aspect of the invention, methods for the preparation of compounds of formula (IV) are provided. In one embodiment of the invention, compounds of formula (II) wherein $R^4$=OH and $R^3$=acetyl are first treated with 1,1-carbonyldiimidazole and 4-(dimethylamino)pyridine to provide the 11,12-cyclic carbonate, as illustrated in Scheme 9.

SCHEME 9

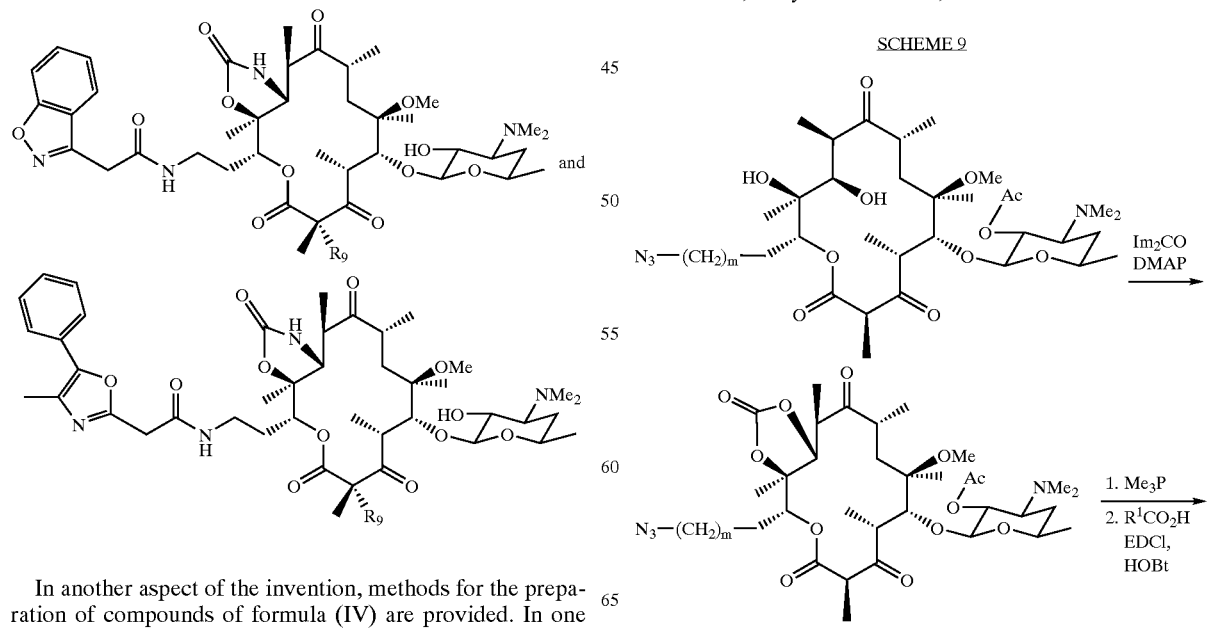

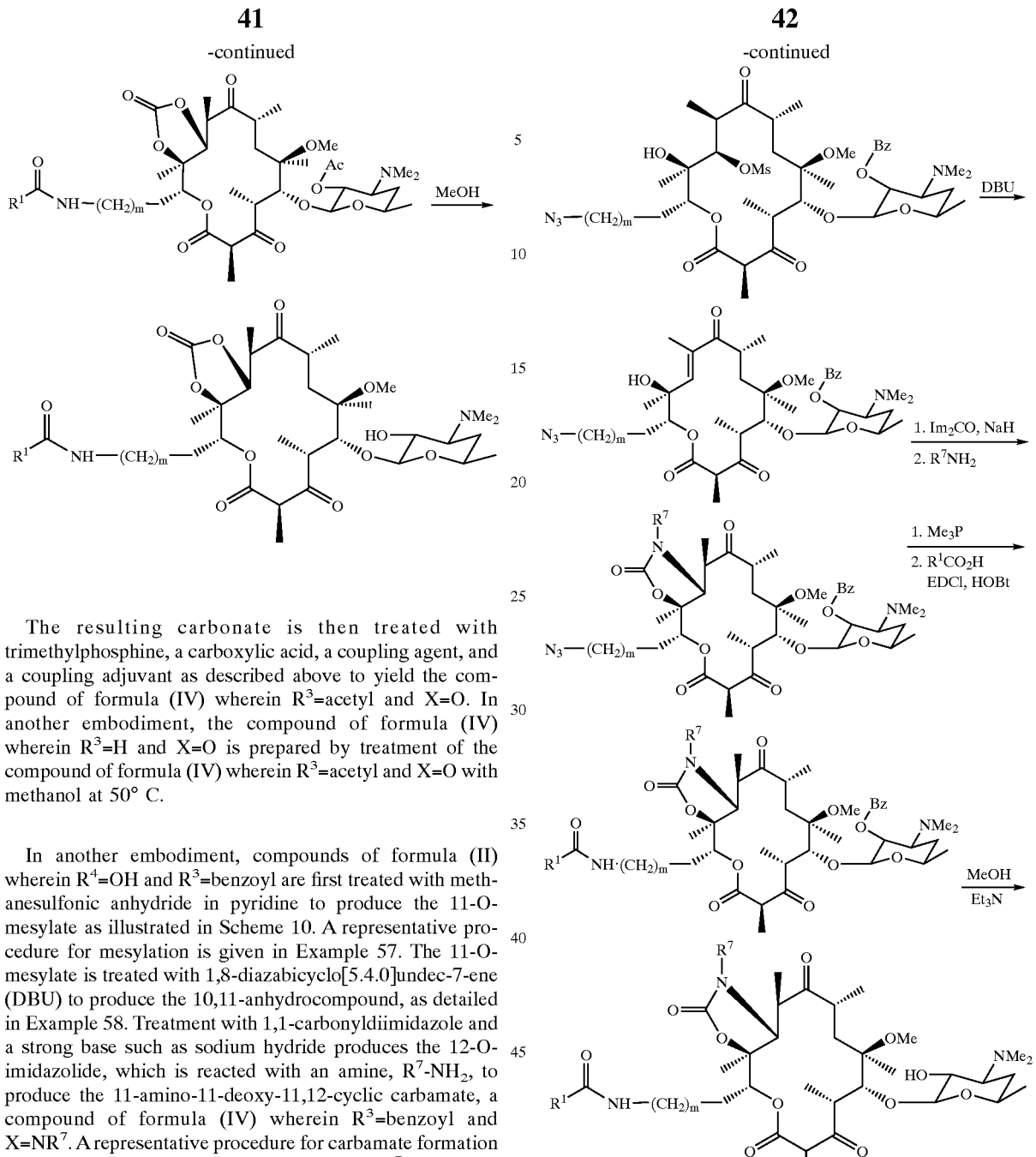

The resulting carbonate is then treated with trimethylphosphine, a carboxylic acid, a coupling agent, and a coupling adjuvant as described above to yield the compound of formula (IV) wherein $R^3$=acetyl and X=O. In another embodiment, the compound of formula (IV) wherein $R^3$=H and X=O is prepared by treatment of the compound of formula (IV) wherein $R^3$=acetyl and X=O with methanol at 50° C.

In another embodiment, compounds of formula (II) wherein $R^4$=OH and $R^3$=benzoyl are first treated with methanesulfonic anhydride in pyridine to produce the 11-O-mesylate as illustrated in Scheme 10. A representative procedure for mesylation is given in Example 57. The 11-O-mesylate is treated with 1,8-diazabicyclo[5.4.0]undec-7-ene (DBU) to produce the 10,11-anhydrocompound, as detailed in Example 58. Treatment with 1,1-carbonyldiimidazole and a strong base such as sodium hydride produces the 12-O-imidazolide, which is reacted with an amine, $R^7$-$NH_2$, to produce the 11-amino-11-deoxy-11,12-cyclic carbamate, a compound of formula (IV) wherein $R^3$=benzoyl and X=$NR^7$. A representative procedure for carbamate formation when X=NH is given in Example 59. When $R^7$=alkyl, it is usually necessary to perform the reaction at elevated temperature, for example 50° C., in order to provide the (10R) diastereomer.

SCHEME 10

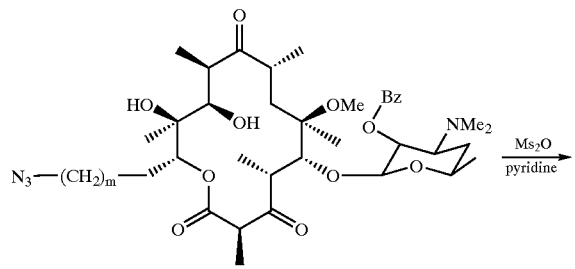

In another embodiment of the invention, a compound of formula (IV) wherein $R^3$=acetyl or benzoyl and $R^8$=F is prepared from a compound of formula (IV) wherein $R^3$=acetyl or benzoyl and $R^8$=H by treatment with potassium tert-butoxide and NFBS. A representative procedure for fluorination is given in Example 60.

Figure 3:
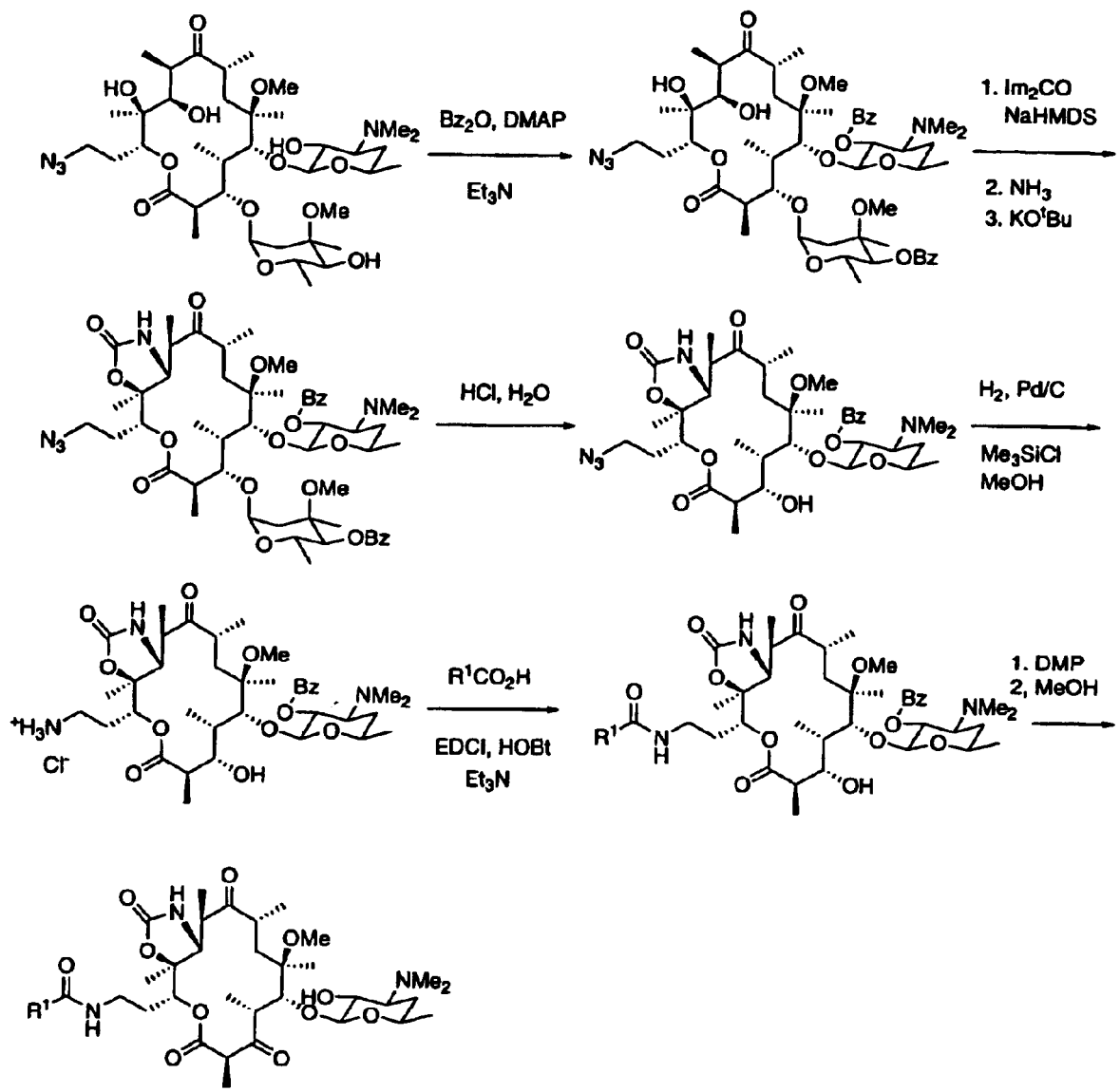
FIG. 3 shows a synthetic procedure that may be used to prepare certain macrolides according to the invention. $R^1$ is as defined in the specification and can include any of the groups shown in FIGS. 1 and 2.

In another embodiment of the invention, a compound of formula (IV) wherein X=$NR^7$ is prepared according to the method illustrated in FIG. 3. An azidoerythromycin wherein $R^4$ is OH and $R^5$ is alkoxy, alkyenyloxy, or alkynyloxy, prepared for example according to the method illustrated in Scheme 4 above, is protected as the 2',4''-diacetate or 2',4''-dibenzoate. Treatment with 1,1-carbonyldiimidazole and a strong base, for example sodium bis(trimethylsilyl) amide (NaHMDS) in an inert solvent such as tetrahydrofuran at a temperature between −10° C. and 30° C., followed by treatment with an amine, for example ammonia, and subsequently potassium tert-butoxide provides the 11,12-cyclic carbamate. The cladinose is removed, for example by treatment with aqueous acid, and the resulting 3-OH is subjected to hydrogenolysis to reduce the azide to the amine. Hydrogenolysis is performed in a solvent such as methanol in the presence of a metal catalyst, such as palladium or palladium supported on an inert material such as charcoal, and an acid, such as HCl, acetic acid, or similar, under a moderate pressure of hydrogen gas, such as that provided by a hydrogen balloon. The acid may be generated in situ, for example by addition of chlorotrimethylsilane to methanol. The resulting ammonium salt is condensed with a carboxylic acid $R^1COOH$ as described above. Subsequent to amide formation, the 3-OH is oxidized to the 3-oxo group, for example using the Dess-Martin periodinane, Swern oxidation, Corey-Kim oxidation, or similar. Finally, the 2'-protecting group is removed by methanolysis. This procedure is exemplified in detail in Example 81 below.

In another embodiment of the invention, the compound of formula (IV) wherein $R^3$=benzoyl is treated with methanol and triethylamine at 50° C. to provide the compound of formula (IV) wherein $R^3$=H and $X$=$NR^7$. A representative procedure for debenzoylation is given in Example 62.

In another aspect of the invention, compounds of formula (V) are provided

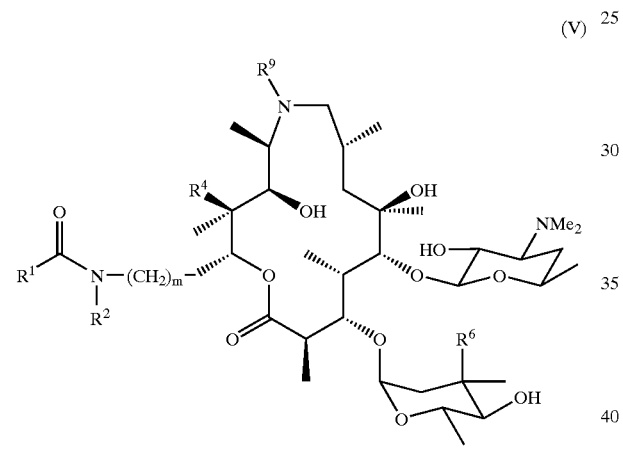

(V)

wherein $R^1$, $R^2$, $R^4$, $R^6$ and m are as defined above; and $R^9$ is H or $C_1$–$C_4$ alkyl.

In one embodiment of the invention, compounds of formula (V) are provided wherein $R^1$ is $C_6$–$C_{15}$ substituted or unsubstituted arylalkyl, $C_6$–$C_{15}$ substituted or unsubstituted biarylalkyl, $C_6$–$C_{15}$ substituted or unsubstituted arylalkenyl, or $C_6$–$C_{15}$ substituted or unsubstituted arylalkynyl.

In another embodiment of the invention, compounds of formula (V) are provided wherein m=0.

In another embodiment of the invention, compounds of formula (V) are provided wherein m=1.

In another embodiment of the invention, compounds of formula (V) are provided wherein m=2.

In one embodiment of the invention, compounds of formula (V) are provided wherein $R^2$=H; $R^4$=OH; $R^6$=OMe; $R^9$=Me; and m=0.

In another embodiment of the invention, compounds of formula (V) are provided wherein $R^2$=H; $R^4$=OH; $R^6$=OMe; $R^9$=Me; and m=1.

In another embodiment of the invention, compounds of formula (V) are provided wherein $R^2$=H; $R^4$=OH; $R^6$=OMe; $R^9$=Me; and m=2.

In another embodiment of the invention, compounds of formula (V) are provided wherein $R^1$ is $C_4$–$C_{15}$ substituted or unsubstituted aryl, $C_5$–$C_{20}$ substituted or unsubstituted arylalkyl, or $C_5$–$C_{20}$ substituted or unsubstituted biarylalkyl.

In another aspect of the invention, methods for the preparation of compounds of formula (V) are provided. In one embodiment of the invention, an azidoerythromycin 9-oxime described above is subjected to a Beckmann rearrangement as illustrated in Scheme 11.

SCHEME 11

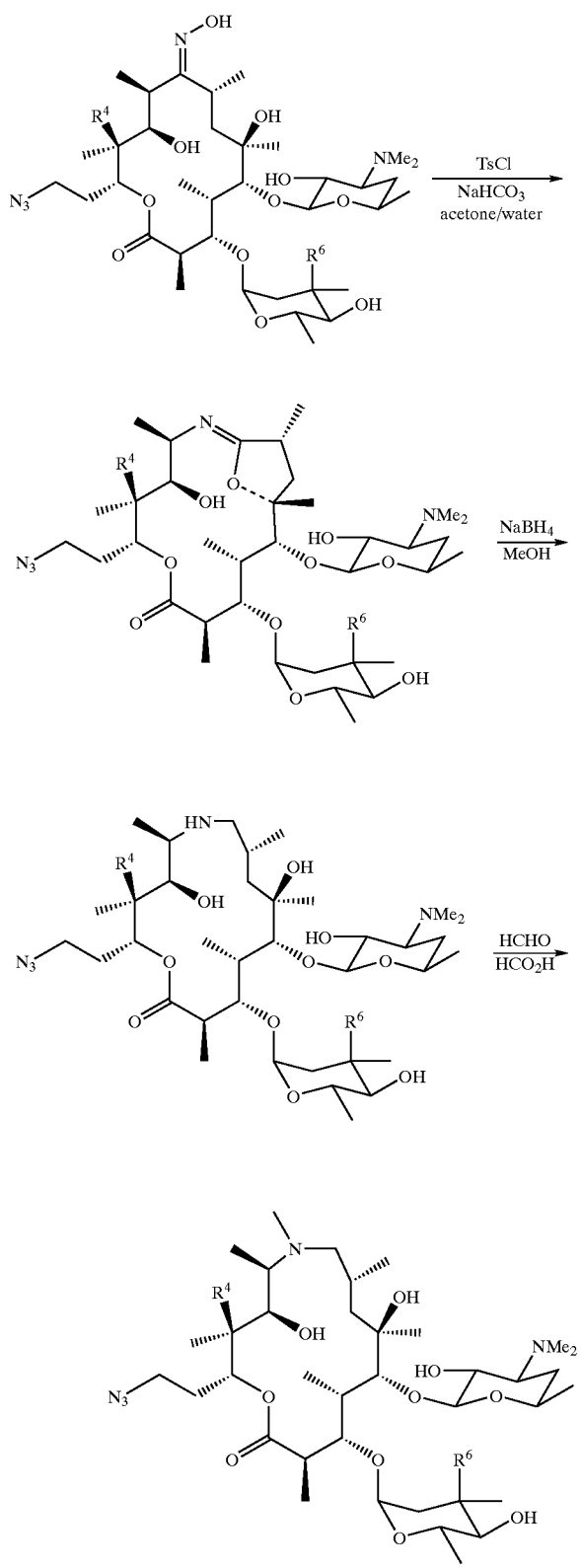

Treatment of the azidoerythromycin 9-oxime with a sulfonyl chloride, for example benzenesulfonyl chloride or p-toluenesulfonyl chloride (TsCl) in the presence of sodium bicarbonate, yields the 6,9-cyclic iminoether as described for the preparation of azalides derived from erythromycin A in Kobrehel et al., "11-Aza-10-deoxo-10-dihydroerythromycin A and derivatives thereof as well as a process for their production," U.S. Pat. No. 4,328,334, incorporated herein by reference. The oximinoether is then reduced, for example using sodium borohydride, under conditions wherein the azide group remains intact. The resulting azalide is then alkylated, for example methylated using formaldehyde and formic acid as described for the production of azithromycin in Kobrehel & Djokic, U.S. Pat. No. 4,517,359, incorporated herein by reference, to produce the azidoazalide.

In another embodiment of the invention, the azidoazalide is converted into an embodiment of the compounds of formula (V) as illustrated in Scheme 12. According to this embodiment, the 2'-OH is protected, for example as the acetate or benzoate, and the azide is reduced by treatment with a phosphine, for example trimethylphosphine or triphenylphosphine, and the amide is formed by condensation with carboxylic acid $R^1COOH$ as described above. Finally, the 2'-protecting group is removed by methanolysis.

SCHEME 12

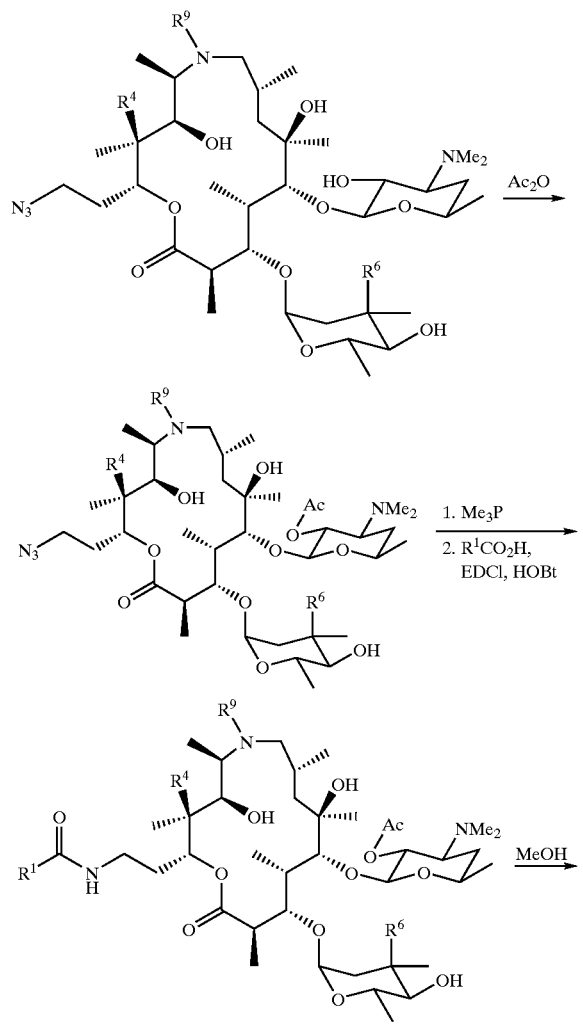

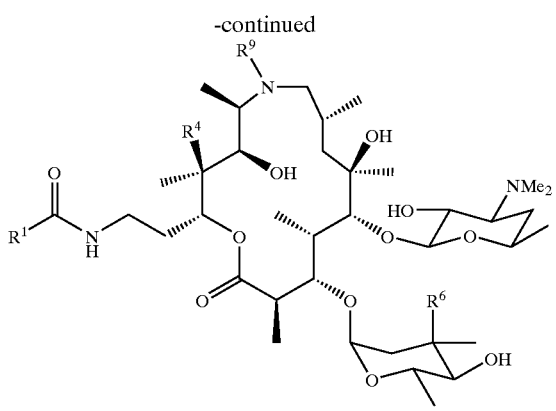

In another embodiment, the azidoazalide is converted into an embodiment of the compounds of formula (V) by protecting the 2'-OH as the acetate or benzoate, reducing the azide to the amine by hydrogenolysis and forming the amide by condensation of the aminoazalide with $R^1COOH$ as described above.

Methods of Use

This invention further provides a method of treating bacterial infections, or enhancing the activity of other antibacterial agents, in warm-blooded animals, which comprises administering to the animals a compound of the invention alone or in admixture with a diluent or in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixers containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose, and kaolin, while liquid carriers include sterile water, polyethylene glycols, non-ionic surfactants and edible oils such as corn, peanut and sesame oils, as are appropriate to the nature of the active ingredient and the particular form of administration. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The active compounds may also be administered parenterally or intraperitoneally. Solutions or suspensions of these active compounds as a free base or pharmacologically acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given once a day, or in divided doses two to four times a day, or in sustained release form. For most large mammals, including humans, the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regiment may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

A detailed description of the invention having been provided above, the following examples are given for the purpose of illustrating the present invention and shall not be construed as being a limitation on the scope of the invention or claims.

EXAMPLE 1

(±)-(2S*,3R*)-5-chloro-3-hydroxy-2-methylpentanoate N-propionylcysteamine thioester

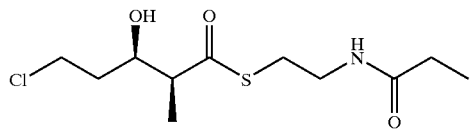

3-Chloropropanal

Anhydrous hydrogen chloride was bubbled into a stirred solution of freshly distilled acrolein (11.2 g) and dicinnamylacetone (5 mg) in 100 mL of $CH_2C_2$ at 0° C. until a red color persisted. $^1$H-NMR analysis of a 20 uL-aliquot diluted into 500 uL of $CDCl_3$ showed 95% conversion to 3-chloropropanal, and integration relative to the $CH_2Cl_2$ peak showed the reaction solution to contain 1.8 M 3-chloropropanal.

(±)-3-[(2S*,3R*)-5-chloro-3-hydroxy-2-methylpentanoyl]-2-benzoxazolone

A vigorously stirred solution of 3-propionyl-2-benzoxazolone (19.1 g) in 200 mL of $CH_2Cl_2$ at 0° C. was treated with titanium tetrachloride (12.0 mL) followed by slow addition of triethylamine (16.7 mL). After stirring for 30 minutes, the dark red solution was treated with 60 mL of 1.8 M 3-chloropropanal in $CH_2Cl_2$ for 30 minutes, then quenched by addition of 200 mL of 2 N HCl. The phases were separated, and the organic phase was filtered through a pad of silica gel. The aqueous phase was extracted with ether, and the extract was used to wash the pad of silica. The combined silica eluate was concentrated under reduced pressure, resulting in crystallization. The white crystals were collected by vacuum filtration and dried to provide 19.9 g of product; mp=116–117° C.

(±)-(2S*,3R*)-5-chloro-3-hydroxy-2-methylpentanoate N-propionylcysteamine thioester A 4.37 M solution of sodium methoxide in methanol (66.54 mL) was added to a stirred solution of N,S-dipropionylcysteamine (55.04 g) in 224.5 mL of methanol under inert atmosphere. After 25 minutes, glacial acetic acid (13.32 mL) was added followed by solid (±)-3-[(2S*,3R*)-5-chloro-3-hydroxy-2-methylpentanoyl]-2-benzoxazolone (75.0 g). After an additional 10 minutes, glacial acetic acid (9.38 mL) was added and the mixture was concentrated under reduced pressure. The residue was diluted with 1,2-dichloroethane and reconcentrated under reduced pressure. The residue was dissolved in ethyl acetate and filtered through silica gel, washing the silica with additional ethyl acetate. The eluate was concentrated and the residue was chromatographed on 500 g of silica gel, eluting with a gradient from 20% ethyl acetate in $CH_2Cl_2$ to 100% ethyl acetate. The product-containing fractions were pooled and evaporated. The residue was triturated with hexanes, concentrated, and allowed to crystallize, yielding 53.0 g of pure product. $^{13}$C-NMR ($CDCl_3$, 100 MHz): δ 203.4, 174.5, 69.0, 53.5, 41.8, 38.9, 36.9, 29.6, 28.8, 11.5, 9.8.

EXAMPLE 2

15-chloro-6-dEB

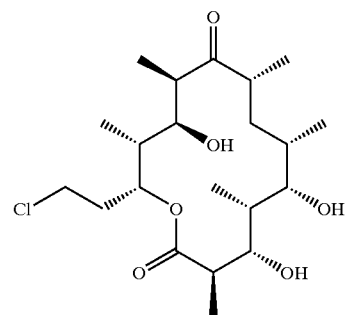

A seed culture of *Streptomyces coelicolor* CH999/pJRJ2 was made by inoculating 1 mL of frozen mycelium into a 250 mL baffled flask containing 50 mL of FKA medium (corn starch, 45 g/L; corn steep liquor, 10 g/L; dried, inactivated brewers yeast, 10 g/L; and $CaCO_3$, 1 g/L), 0.050 mL of 50 mg/mL thiostrepton in DMSO (filter sterilized), and 0.500 mL of 50% Antifoam B. The flask was incubated at 30° C. with shaking at 175 rpm for 48 hours (Innova floor shaker). The culture was transferred into a 2.8-L baffled flask containing 500 mL of FKA medium, 0.500 mL of 50 mg/mL thiostrepton in DMSO, and 5 mL of 50% Antifoam B, and the flask was incubated at 30° C. with shaking at 175 rpm for 48 hours.

A 10-L stirred tank bioreactor (B. Braun) was autoclaved, filled with 5 L of sterile FKA medium and 5 mL of 50 mg/mL thiostrepton in DMSO, and then inoculated with 500 mL (10%) of seed culture. The bioreactor was run for 24 hours at 30° C. with stirring at 600 rpm, sparged with air at 1.33 LPM, and the pH was maintained at 6.50 by automated addition of 2.5 N NaOH and 2.5 N $H_2SO_4$.

Three liters of the above culture was used to inoculate a 100-L bioreactor containing 55 L of sterile FKA medium with 2 g/L Tastone 310 added prior to sterilization. The fermentor agitation rate was set at a tip speed of 2.5 m/s, the temperature was maintained at 30° C., the pH was controlled at pH 6.5 by automated addition of 2.5 N NaOH and 2.5 N $H_2SO_4$, and the airflow was set at 0.4 vvm. Foaming was controlled by automated addition of 50% Antifoam B. During the fermentation, the dissolved oxygen was maintained at ≧50% air saturation by cascade control using the agitation rate (tip speed of 2.5–3.0 m/s) and back pressure (0.1–0.4 bar) in that order. After 24 hours post-inoculation, a 400 g/L solution of (±)-(2S*,3R*)-5-chloro-3-hydroxy-2-methylpentanoate N-propionylcysteamine thioester in DMSO was added to a final concentration of 1 g/L. Titers of 15-chloro-6-deoxyerythronolide B were monitored by HPLC, and the culture was harvested by centrifugation when a maximum titer was reached.

The 15-chloro-6-deoxyerythronolide B was isolated by solid phase extraction. The broth was clarified by centrifugation and loaded onto a column containing HP-20 resin (Rohm and Haas) at a concentration of 1 L resin20 g 15-chloro-6-deoxyerythronolide B. The column was then equilibrated with 5 column volumes of water at a flow rate of 2–4 mL/cm²-min. The loaded resin was washed with 2 column volumes of water followed by 2 column volumes of 30% methanol in water. The 15-chloro-6-deoxyerythronolide B was eluted from the resin with methanol. The fractions containing 15-chloro-6-deoxyerythronolide B were identified by HPLC with ELSD detection.

The methanol fractions containing 15-chloro-6-deoxyerythronolide B were pooled, and the volatiles were removed under reduced pressure. The dried solids were extracted with 3–5 L of methanol and filtered to yield a solution containing 6–10 mg/mL 15-chloro-6-deoxyerythronolide B, which was diluted with an equal volume of water. This solution was loaded onto a column of HP20SS (1 L resin/20 g of 15-chloro-6-deoxyerythronolide B), which was then washed with 2 column volumes of 50% aqueous methanol. The 15-chloro-6-deoxyerythronolide B was then eluted with 70% methanol in water, and the fractions were analyzed by HPLC. Product-containing fractions were pooled and evaporated to dryness to yield 19.07 g of 15-chloro-6-deoxyerythronolide B of 88% purity. $^{13}$C-NMR (CDCl$_3$, 100 MHz): δ 213.7, 178.0, 79.3, 76.3, 71.6, 70.7, 43.8, 43.2, 41.0 (2C), 39.5, 37.6, 37.5, 35.4, 35.0, 16.6, 14.6, 13.3, 9.4, 6.9, 6.2.

EXAMPLE 3

15-azido-6-dEB

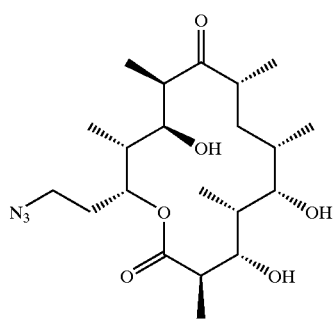

A mixture of 15-chloro-6-dEB (19.07 g, ca. 88% pure), sodium iodide (5.95 g), and sodium azide (10.31 g) in 60 mL of dimethylsulfoxide was heated at 50° C. for 3 days. The mixture was cooled to ambient temperature and diluted with ethyl acetate. The solution was washed with water, and the aqueous phase was extracted with ethyl acetate. The combined organic phases were washed with brine, dried over MgSO$_4$, filtered, and evaporated. The residue was purified by silica gel chromatography using ethyl acetate/hexanes, yielding 13.96 g of 15-azido-6-dEB. $^{13}$C-NMR (CDCl$_3$, 100 MHz): δ 213.6, 178.0, 79.3, 76.4, 71.8, 70.7, 48.5, 43.9, 43.2, 41.2, 39.6, 37.7, 37.5, 35.6, 31.7, 16.6, 14.7, 13.4, 9.3, 6.9, 6.3.

EXAMPLE 4

15-azidoerythromycin A

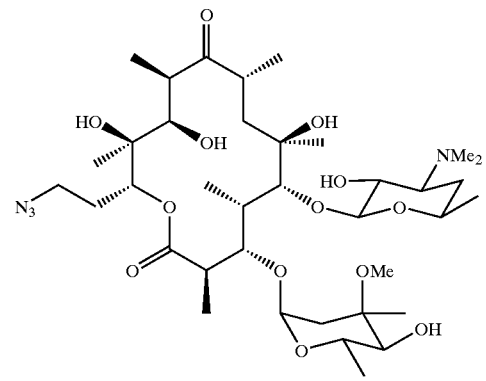

A seed culture of *Saccharopolyspora erythraea* K39-14V was made by inoculating a 1 mL aliquot of frozen mycelium into each of three 250 mL baffled flasks containing 50 mL of V1 medium (corn starch, 16 g/L; corn dextrin, 10 g/L; soya meal flour, 15 g/L; corn steep liquor, 5 g/L; soy bean oil, 6 g/L; sodium chloride, 2.5 g/L; ammonium sulfate, 1 g/L; and CaCO$_3$, 4 g/L) and 0.100 mL of Antifoam B. The flasks were incubated at 34° C. with shaking at 175 rpm for 48 hours (Innova floor shaker). Each culture was transferred into a 2.8-L baffled flask containing 500 mL of V1 medium and 1 mL of Antifoam B, and the flasks were incubated at 34° C. with shaking at 175 rpm for 48 hours.

Three 10-L stirred tank bioreactors (B. Braun) were autoclaved, and each filled with 10 L of sterile 50% F1 medium (corn starch, 17.5 g/L; corn dextrin (type 3), 16 g/L; soy meal flour, 16.5 g/L; calcium carbonate, 4 g/L, corn steep liquor, 6 g/L; soy bean oil, 3 g/L; sodium chloride 2.5 g/L; and ammonium sulfate, 1 g/L). The fermentor agitation rate was set at a tip speed of 2–4 m/s, the pH was controlled at pH 7.0 by automated addition of 2.5 N NaOH and 2.5 N H$_2$SO$_4$, the temperature was maintained at 34° C., and the airflow was set at 0.15 vvm. Foaming was controlled by automated addition of 50% Antifoam B. Each fermentor was inoculated with a 500-mL seed culture prepared above. During the fermentation, the dissolved oxygen was maintained at ≧80% air saturation by cascade control using agitation rate (tip speed of 2–4 m/s)airflow (0.15–0.5 vvm), and oxygen enrichment in that order. After 24 hours post-inoculation, a continuous 2 g/L/day dextrin feed (150 g/L dextrin in deionized water) was initiated, and a 4% wv solution of 15-azido-6-deoxyerythronolide B was added to a final concentration of 250–300 mg/L of 15-azido-6-deoxyerythronolide B. Samples were analyzed by HPLC every 12 hours. After cessation of 15-azidoerythromycin production (ca. 60 hours), the culture was harvested by centrifugation.

The 15-azido-erythromycin A was isolated by solid phase extraction. The broth was adjusted to pH 9 using 2.5 N NaOH, clarified by centrifugation, and loaded onto a column containing HP-20 resin (Rohm and Haas) at a concentration of 1 L resin20 g 15-azidoerythromycin A. The column was then equilibrated with 5 column volumes of water at a flow rate of 2–4 mL/cm$^2$-min. The loaded resin was washed with 2 column volumes of water. The 15-azido-erythromycin A was eluted from the resin with 5 column volumes of methanol. The fractions containing 15-azido-erythromycin A were identified by HPLC, pooled, and the volatiles were removed under reduced pressure. The dried solids were mixed with 800 mL of acetone and 3.2-L of hexane for 20 minutes. The mixture was then filtered using a #4 Whatman filter paper. The solids were extracted twice in this manner, and the filtrates were combined and evaporated.

The crude product was dissolved in methanol and diluted with an equal volume of water. This solution was loaded onto a column of HP20SS (1 L resin/20 g of 15-azido-erythromycin A), which was then washed successively with 1 column volume of 50% aqueous methanol, 3 column volumes of 3:2 methanol/water, 3 column volumes of 7:3 methanol/water, 10 column volumes of 4:1 methanol/water, and finally 5 column volumes of 100% methanol. The fractions were analyzed by HPLC. Product-containing fractions were pooled and evaporated to dryness to yield 13 g of 15-azidoerythromycin A of 95% purity. $^{13}$C-NMR (CDCl$_3$, 100 MHz): δ221.9, 175.4, 103.2, 96.3, 83.3, 79.8, 78.0, 75.0, 74.4, 73.0, 72.6, 70.9, 69.0, 68.6, 65.6, 65.4, 49.5, 49.1, 45.2, 44.7, 40.3 (2C), 39.6, 38.5, 37.7, 34.9, 28.6, 27.8, 27.0, 21.5, 21.4, 18.7, 18.2, 16.2, 15.6, 12.0, 9.1.

EXAMPLE 5

2'-O-acetyl-15-azidoerythromycin A

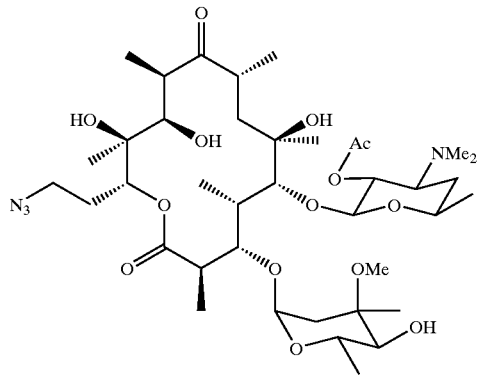

A solution of 15-azidoerythromycin A in CH$_2$Cl$_2$ was treated with acetic anhydride for 1 hour at ambient temperature, then the solution was concentrated to dryness. The residue was chromatographed on silica gel using acetone/hexanes+1% Et$_3$N. $^{13}$C-NMR (CDCl$_3$, 100 MHz): δ 222.0, 175.3, 170.0, 100.9, 96.1, 83.3, 79.6, 77.9, 75.0, 74.4, 73.1, 72.7, 71.7, 68.6, 68.4, 65.7, 63.5, 49.4, 49.1, 45.1, 44.6, 40.7 (2C), 39.4, 38.1, 37.7, 34.9, 30.3, 29.7, 27.8, 27.0, 21.5, 21.2, 18.6, 18.1, 16.3, 15.5, 12.0, 9.0.

EXAMPLE 6

General procedure for preparation of 15-amidoerythromycins

To a solution of 2'-O-acetyl-15-azidoerythromycin A (0.050 g, 0.062 mmol, 1.0 eq) in dichloromethane or tetrahydrofuran (1.0 ml) is added trimethylphosphine (0.31 ml of a 1M solution in THF, 0.306 mmol, 5.0 eq). The solution is stirred at room temperature for 45 minutes before transferring to a solution of the carboxylic acid (0.092 mmol, 1.5 eq), 1-[(3-(dimethylamino)propyl]-1-ethylcarbodiimide hydrochloride (0.019 g, 0.099 mmol, 1.6 eq) and 1-hydroxybenzotriazole (0.017 g, 0.124 mmol, 2.0 eq) in dichloromethane or tetrahydrofuran (1.0 ml) also stirred at room temperature for 45 minutes. The resulting solution is stirred at room temperature for 3 to 14 hours before partitioning between ethyl acetate (10 ml) and NaHCO$_3$ (10 ml). The aqueous phase is extracted with ethyl acetate (3×10 ml) and the combined organics further washed with brine (25 ml) before drying (Na$_2$SO$_4$), filtering, and concentrating under reduced pressure. The residue is dissolved in methanol (2 ml) and stirred at 50° C. for 14 hours before concentrating under reduced pressure. Silica gel chromatography (0→10 min 50% acetone-hexane, 1% Et$_3$N; 10→20 min 60% acetone-hexane, 1% Et$_3$N; 20→30 min 70% acetone-hexane, 1% Et$_3$N; 30+min 80% acetone-hexane, 1% Et$_3$N) yields the 15-amido compound as a white solid.

EXAMPLE 7

15-(6-quinolinecarboxamido)erythromycin A

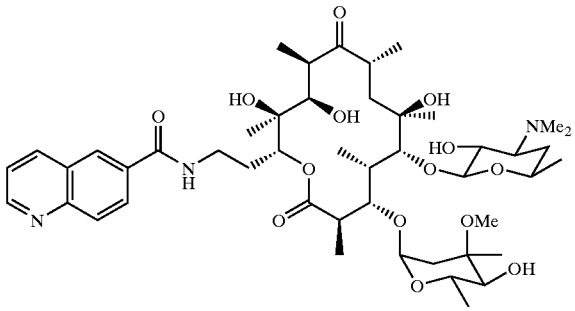

This compound was prepared according to the method of Example 6 using quinoline-6-carboxylic acid. $^{13}$C-NMR (CDCl$_3$, 100 MHz): δ 222.2, 177.0, 166.7, 151.8, 149.3, 137.2, 132.6, 129.9, 127.7, 127.6, 127.3, 121.8, 103.2, 96.3, 83.1, 79.4, 78.0, 75.1, 74.4, 73.0, 72.6, 70.8, 69.0 (2C), 65.7 (2C), 49.5, 45.1, 44.8, 40.3 (2C), 40.2, 38.4, 37.9, 36.6, 34.9, 28.6, 28.4, 27.0, 21.5, 21.4, 18.7, 18.0, 16.3, 15.5, 11.9, 9.0. ES-MS: m/z 905 [M+H]$^+$.

EXAMPLE 8

15-(4-quinolinecarboxamido)erythromycin A

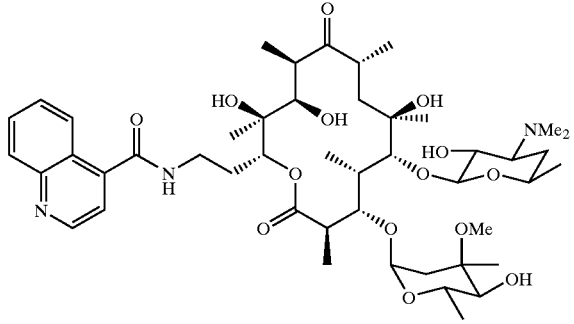

This compound was prepared according to the method of Example 6 using quinoline-4-carboxylic acid. $^{13}$C-NMR (CDCl$_3$, 100 MHz): δ 221.8, 176.7, 167.4, 149.9, 148.5, 142.2, 129.9, 129.7, 127.6, 125.4, 124.6, 118.6, 103.2, 96.3, 83.2, 79.5, 78.0, 74.9, 74.4, 72.9, 72.6, 70.8, 69.0, 68.9, 65.6, 49.5, 44.7, 40.3, 39.9, 38.4, 37.9, 36.6, 34.9, 29.2, 28.6, 26.8, 21.5, 18.7, 18.0, 16.3, 15.5, 11.9, 9.0. ES-MS: m/z 905 [M+H]$^+$, 747, 453.

EXAMPLE 9

15-(3-indoleacetamido)erythromycin A

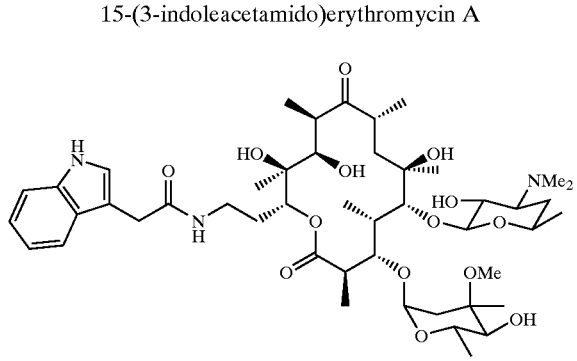

This compound was prepared according to the method of Example 6 using 3-indoleacetic acid. $^{13}$C-NMR (CDCl$_3$, 100 MHz): δ 222.0, 176.1, 171.6, 136.5, 127.1, 124.1, 122.3, 119.8, 118.7, 111.4, 108.9, 103.2, 96.3, 83.3, 79.5, 76.7, 75.0, 74.3, 72.6, 72.5, 70.8, 69.0, 68.8, 65.7, 65.5, 49.5, 45.1, 44.7, 40.2, 39.9, 38.0, 36.0, 34.9, 33.4, 29.7, 28.5, 28.2, 26.9, 21.5, 21.4, 18.6, 18.1, 16.4, 15.4, 11.9, 9.0. ES-MS: m/z 907 [M+H]$^+$, 749, 454.

EXAMPLE 10

15-(phenylacetamido)erythromycin A

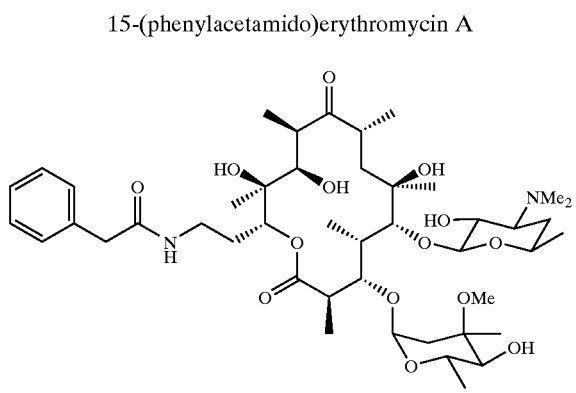

This compound was prepared according to the method of Example 6 using phenylacetic acid. $^{13}$C-NMR (CDCl$_3$, 100 MHz): δ 176.1, 170.9, 135.0, 129.4, 128.9, 127.2, 103.2, 96.3, 83.2, 79.6, 78.0, 75.1, 74.3, 72.7, 72.6, 70.8, 69.0, 68.8, 65.6, 49.5, 45.2, 44.7, 43.8, 40.3, 38.5, 37.9, 36.3, 34.9, 29.7, 28.7, 28.4, 26.9, 21.5, 21.4, 18.6, 18.2, 16.2, 15.5, 11.9, 9.1. ES-MS: m/z 868 [M+H]$^+$.

EXAMPLE 11

15-(phenylapropionamido)erythromycin A

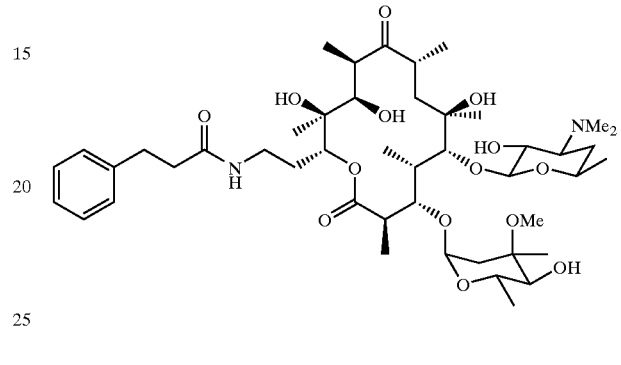

This compound was prepared according to the method of Example 6 using hydrocinnamic acid. $^{13}$C-NMR (CDCl$_3$, 100 MHz): δ 222.0, 176.5, 172.0, 141.0, 128.5, 128.4, 126.1, 103.2, 96.3, 83.2, 79.5, 78.0, 75.1, 74.3, 72.8, 72.6, 70.8, 69.9, 68.9, 65.6, 49.5, 45.2, 44.7, 40.3, 40.0, 38.4, 37.9, 35.8, 34.9, 31.7, 28.6, 28.4, 26.9, 21.5, 21.4, 18.6, 18.1, 16.2, 15.5, 11.9, 9.0. ES-MS: m/z 882 [M+H]$^+$.

EXAMPLE 12

15-(2-quinoxalinecarboamido)erythromycin A

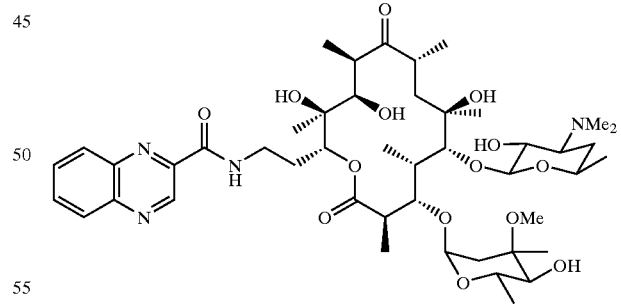

This compound was prepared according to the method of Example 6 using 2-quinazolinecarboxylic acid. $^{13}$C-NMR (CDCl$_3$, 100 MHz): δ 222.1, 175.9, 163.2, 143.9, 143.5, 140.3, 131.5, 130.7, 129.7, 129.5, 103.0, 96.4, 83.5, 79.7, 77.9, 75.0, 74.4, 73.1, 72.6, 70.8, 68.8, 65.7, 65.6, 60.4, 49.5, 45.1, 44.8, 40.3, 39.8, 38.5, 37.9, 36.7, 34.9, 29.7, 29.2, 28.7, 26.9, 22.7, 21.5, 21.3, 18.6, 18.2, 16.3, 15.7, 11.9, 9.2. ES-MS: m/z 906 [M+H]$^+$.

EXAMPLE 13
15-(4-(4-chlorophenyl)benzamido)erythromycin A
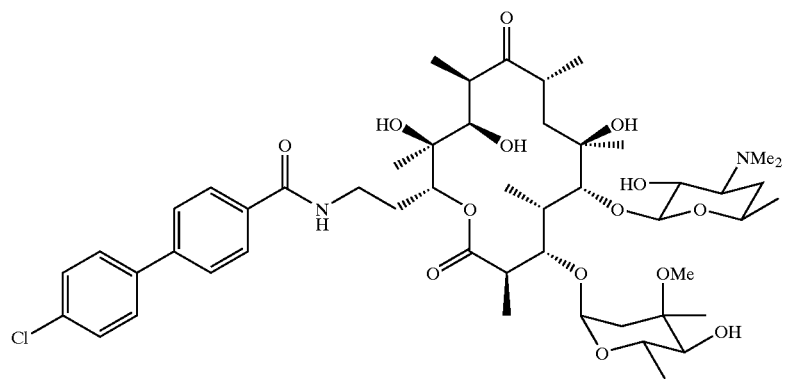
This compound was prepared according to the method of Example 6 using 4-(4-chlorophenyl)benzoic acid. $^{13}$C-NMR (CDCl$_3$, 100 MHz): δ 168.8, 142.7, 134.1, 133.6, 129.0, 128.4, 127.6, 127.0, 103.1, 96.3, 83.1, 79.4, 78.0, 75.2, 74.3, 72.9, 70.8, 69.1, 65.5, 60.4, 49.5, 45.1, 44.8, 40.2, 38.4, 37.9, 36.3, 34.9, 29.7, 28.6, 28.3, 27.0, 21.5, 21.4, 21.0, 18.6, 18.0, 16.3, 15.5, 11.9, 9.0. ES-MS: m/z 964 [M+H]$^+$.
EXAMPLE 14
15-(5-phenylpentamido)erythromycin A
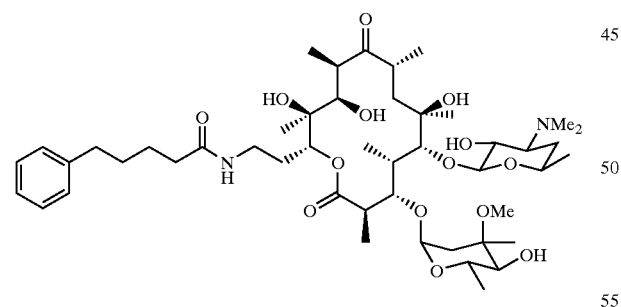
This compound was prepared according to the method of Example 6 using 5-phenylpentanoic acid. $^{13}$C-NMR (CDCl$_3$, 100 MHz): δ 178.7, 172.8, 151.7, 142.3, 128.4, 128.3, 125.7, 102.9, 101.8, 94.5, 85.7, 79.8, 78.1, 75.9, 75.0, 74.8, 73.0, 70.7, 70.3, 68.9, 65.9, 49.6, 44.4, 43.6, 40.3, 36.7, 35.9, 34.6, 31.1, 30.5, 28.6, 28.2, 26.5, 25.4, 21.6, 21.4, 18.2, 16.4, 14.7, 13.0, 11.8. ES-MS: m/z 892 [M+H]$^+$.

EXAMPLE 15

15-(4-(4-chlorophenyl)phenylacetamido)erythromycin A

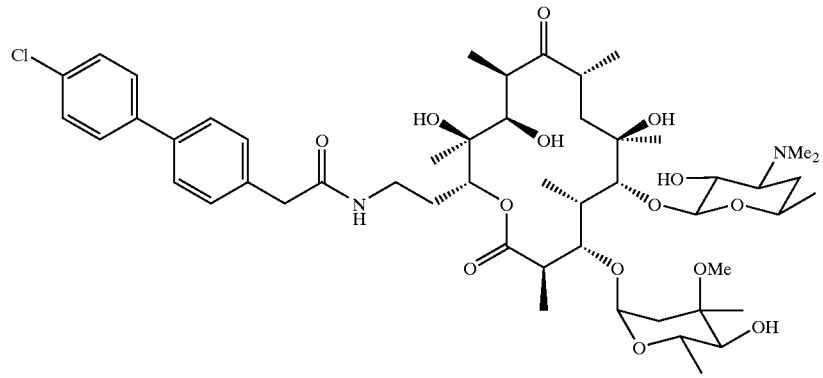

This compound was prepared according to the method of Example 6 using 4-(4-chlorophenyl)phenylacetic acid. $^{13}$C-NMR (CDCl$_3$, 100 MHz): δ 222.8, 176.2, 170.8, 139.2, 138.8, 134.5, 133.4, 129.9, 128.9, 128.3, 127.4, 103.1, 96.3, 83.2, 79.5, 78.0, 75.0, 74.3, 72.6, 70.8, 69.0, 68.9, 65.6, 65.6, 49.5, 45.1, 44.7, 43.4, 40.2, 39.9, 38.4, 36.2, 34.8, 29.7, 28.3, 26.9, 21.5, 21.4, 18.6, 18.1, 16.2, 15.5, 11.9, 9.0. ES-MS: m/z 978 [M+H]$^+$.

EXAMPLE 16

15-(2-(2-furyl)phenylacetamido)erythromycin A

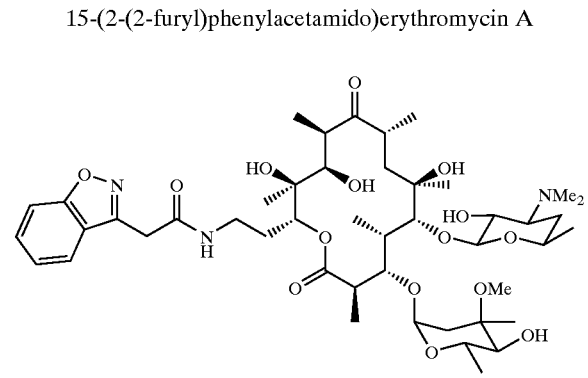

This compound was prepared according to the method of Example 6 using 2-(1,2-benzisoxaol-3-yl)acetic acid. $^{13}$C-NMR (CDCl$_3$, 100 MHz): δ 176.3, 166.9, 163.2, 153.7, 130.1, 123.7, 122.1, 121.3, 109.8, 103.2, 96.3, 79.6, 78.0, 74.9, 74.4, 72.9, 72.6, 69.0, 68.8, 65.5, 49.5, 45.1, 44.7, 40.3, 39.9, 38.5, 38.0, 36.6, 34.9, 33.6, 29.7, 28.6, 28.4, 26.8, 21.5, 21.4, 18.6, 18.2, 16.2, 15.5, 11.9, 9.1. ES-MS: m/z 909 [M+H]$^+$.

EXAMPLE 17

15-(2-(2-furyl)phenylacetamido)erythromycin A

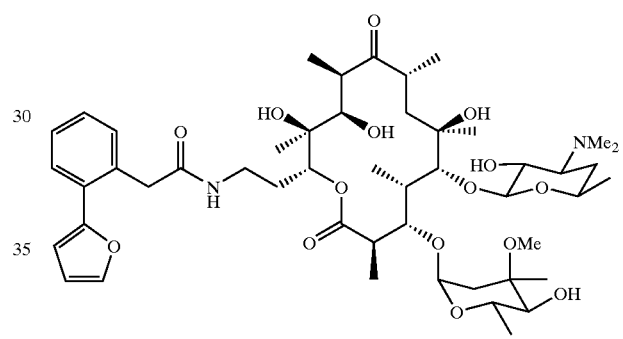

This compound was prepared according to the method of Example 6 using 2-(2-furyl)phenylacetic acid. $^{13}$C-NMR (100 MHz, CDCl$_3$): δ 222.1, 175.8, 170.9, 152.9, 142.5, 131.9, 131.5, 130.8, 128.3, 128.3, 127.7, 111.5, 108.8, 103.1, 96.3, 83.2, 79.5, 77.9, 75.1, 74.2, 72.7, 72.6, 70.8, 69.0, 68.8, 65.7, 65.6, 49.5, 45.1, 44.6, 42.7, 40.2, 39.9, 38.5, 37.9, 36.3, 34.9, 29.7, 28.7, 28.4, 27.0, 21.5, 21.4, 18.6, 18.1, 16.1, 15.5, 11.8, 9.1. ES-MS: m/z 934 [M+H]$^+$.

EXAMPLE 18

15-(3-(2-furyl)phenylacetamido)erythromycin A

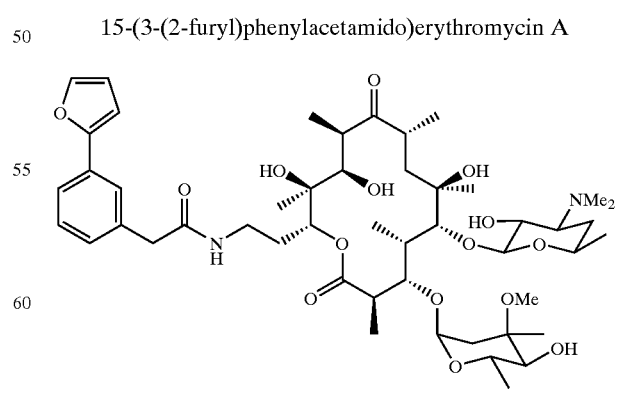

This compound was prepared according to the method of Example 6 using 3-(2-furyl)phenylacetic acid. $^{13}$C-NMR (CDCl$_3$, 100 MHz): δ 222.1, 176.1, 170.7, 153.7, 142.1, 134.0, 131.9, 131.1, 129.8, 124.3, 111.6, 105.0, 103.1, 96.3, 83.1, 79.4, 77.9, 77.2, 75.1, 74.2, 72.6, 70.8, 69.0, 68.9, 65.6, 49.5, 45.1, 44.7, 43.6, 43.4, 40.3, 38.4, 37.9, 36.2, 34.8, 30.4, 29.7, 28.6, 28.3, 27.0, 21.5, 21.4, 18.6, 18.1, 16.2, 15.4, 11.8, 9.0. ES-MS: m/z 934 [M+H]$^+$.

EXAMPLE 19

15-(4-(2-furyl)phenylacetamido)erythromycin A

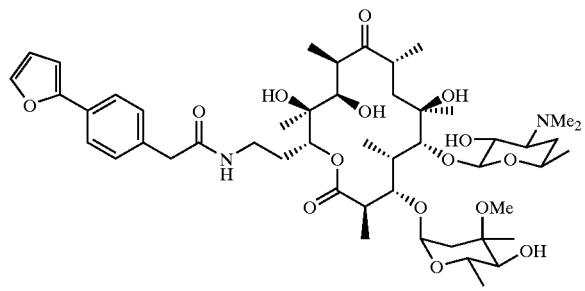

This compound was prepared according to the method of Example 6 using 3-(2-furyl)phenylacetic acid.

EXAMPLE 20

15-(4-phenylbutyramido)erythromycin A

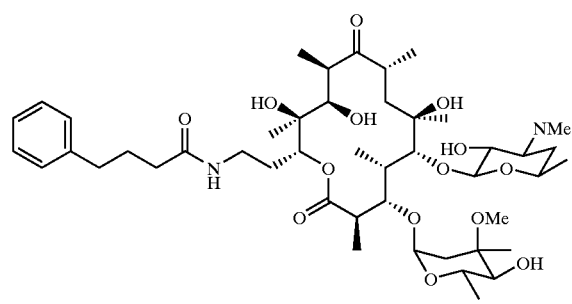

This compound was prepared according to the method of Example 6 using 4-phenylbutyric acid.

EXAMPLE 21

15-(benzyloxyacetamido)erythromycin A

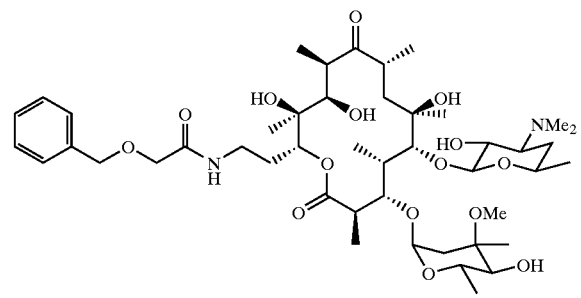

This compound was prepared according to the method of Example 6 using benzyloxyacetic acid.

EXAMPLE 22

15-(3-(3-quinoline)propionamido)erythromycin A

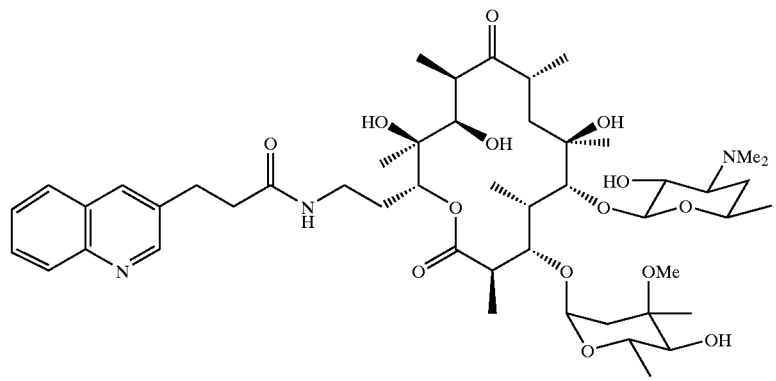

This compound was prepared according to the method of Example 6 using 3-(3-quinolyl)propionic acid.

EXAMPLE 23

15-((3,4,5-trimethoxyphenyl)oxalamido)erythromycin A

This compound was prepared according to the method of Example 6 using (3,4,5-trimethoxybenzoyl)formic acid.

EXAMPLE 24

15-((4-methyl-5-phenyloxazol-2-yl)acetamido)erythromycin A

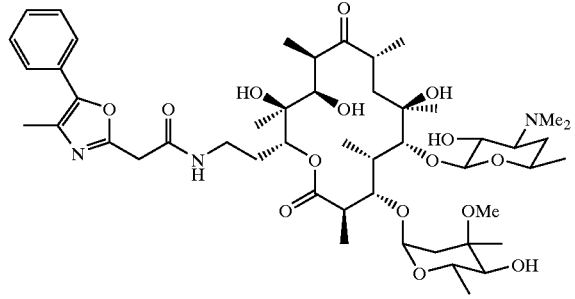

This compound was prepared according to the method of Example 6 using (4-methyl-5-phenyloxazol-2-yl)acetic acid.

EXAMPLE 25

15-(3-quinolinecarboxamido)erythromycin A

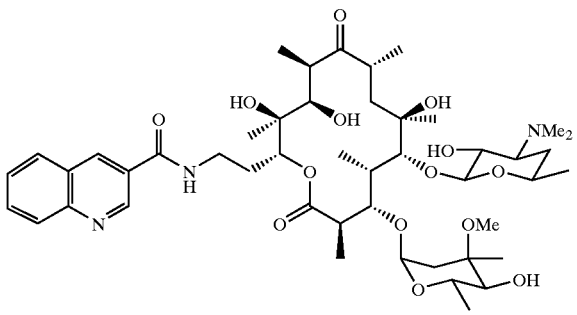

This compound was prepared according to the method of Example 6 using quinoline-3-carboxylic acid.

EXAMPLE 26

15-(3-pyridinecarboxamido)erythromycin A

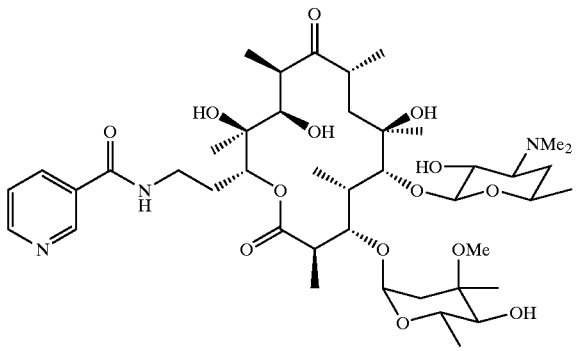

This compound was prepared according to the method of Example 6 using pyridine-3-carboxylic acid.

EXAMPLE 27

15-(5-indolecarboxamido)erythromycin A

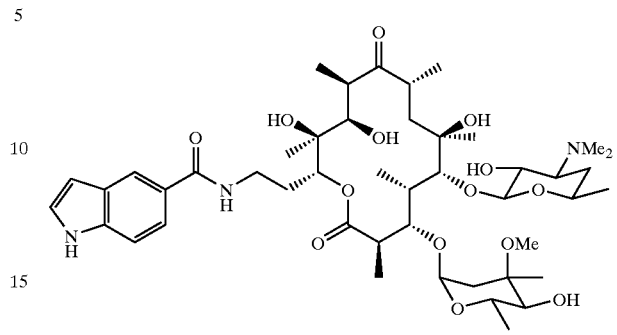

This compound was prepared according to the method of Example 6 using indole-5-carboxylic acid.

EXAMPLE 28

15-(3-indolecarboxamido)erythromycin A

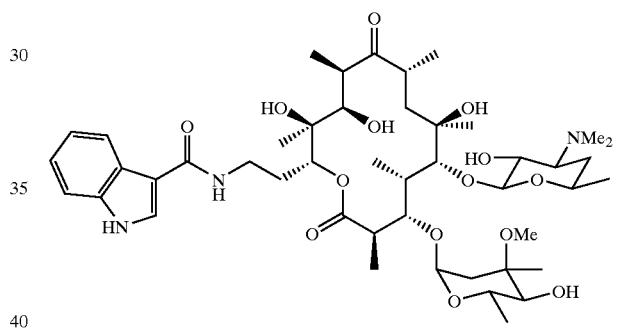

This compound was prepared according to the method of Example 6 using indole-3-carboxylic acid.

EXAMPLE 29

15-(4-(2-furyl)benzamido)erythromycin A

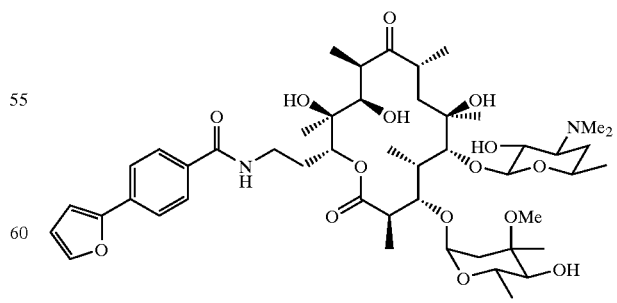

This compound was prepared according to the method of Example 6 using 4-(2-furyl)benzoic acid.

EXAMPLE 30

15-(4-biphenylacetamido)erythromycin A

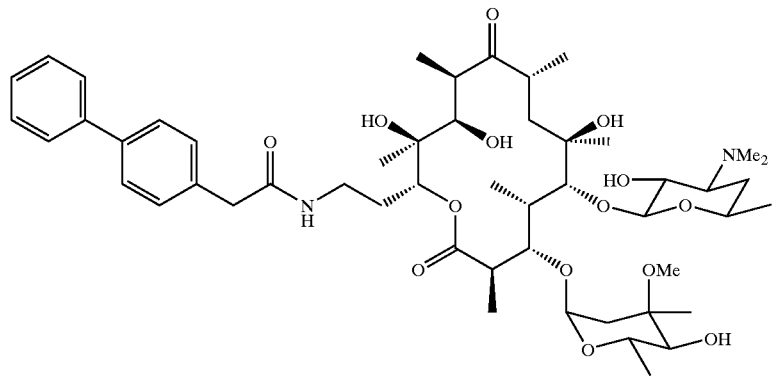

This compound was prepared according to the method of Example 6 using 4-biphenylacetic acid.

EXAMPLE 31

15-(3-(3-furyl)phenylacetamido)erythromycin A

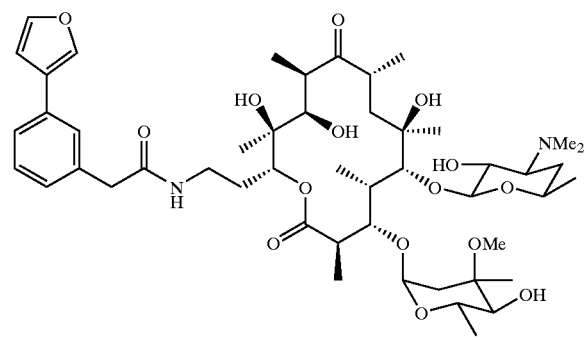

This compound was prepared according to the method of Example 6 using 3-(3-furyl)phenylacetic acid.

EXAMPLE 32

15-(3-(3-thienyl)phenylacetamido)erythromycin A

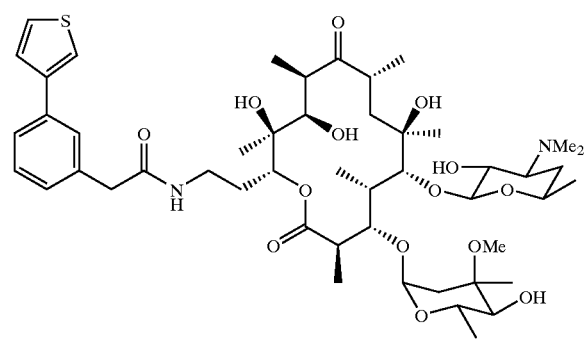

This compound was prepared according to the method of Example 6 using 3-(3-thienyl)phenylacetic acid.

EXAMPLE 33

15-(3-(2-thienyl)phenylacetamido)erythromycin A

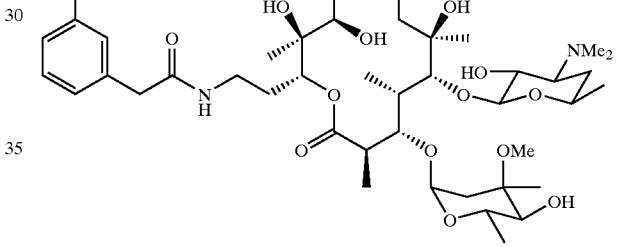

This compound was prepared according to the method of Example 6 using 3-(2-thienyl)phenylacetic acid.

EXAMPLE 34

15-(2-(2-thienyl)phenylacetamido)erythromycin A

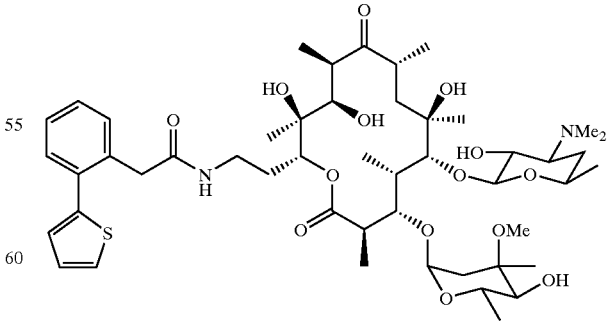

This compound was prepared according to the method of Example 6 using 2-(2-thienyl)phenylacetic acid.

EXAMPLE 35

15-(3-(2-pyrrolyl)phenylacetamido)erythromycin A

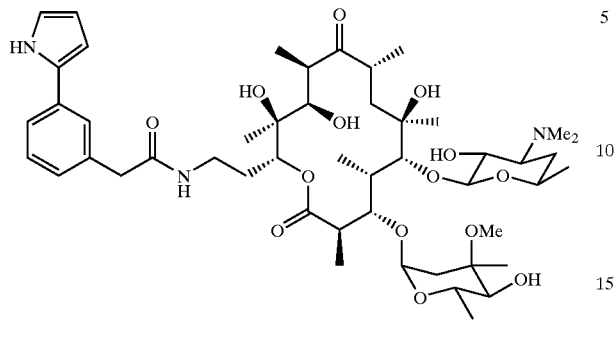

This compound was prepared according to the method of Example 6 using 3-(2-pyrrolyl)phenylacetic acid.

EXAMPLE 36

15-(3-(4-pyridyl)phenylacetamido)erythromycin A

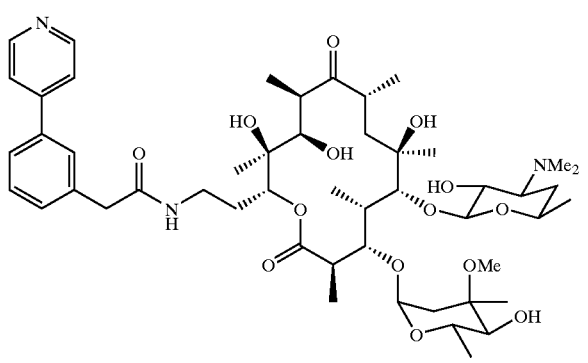

This compound is prepared according to the method of Example 6 using 3-(4-pyridyl)phenylacetic acid.

EXAMPLE 37

15-(3-(2-furyl)pyridyl-5-acetamido)erythromycin A

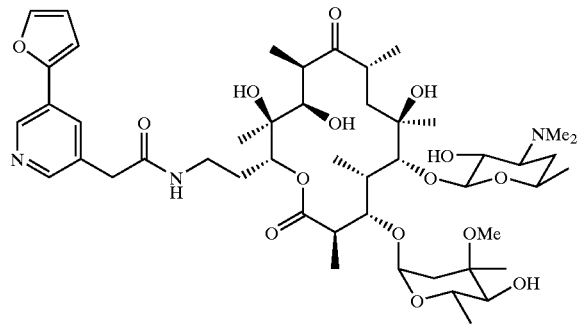

This compound is prepared according to the method of Example 6 using 3-(2-furyl)pyridyl-5-acetic acid.

EXAMPLE 38

15-(3-(2-thienyl)pyridyl-5-acetamido)erythromycin A

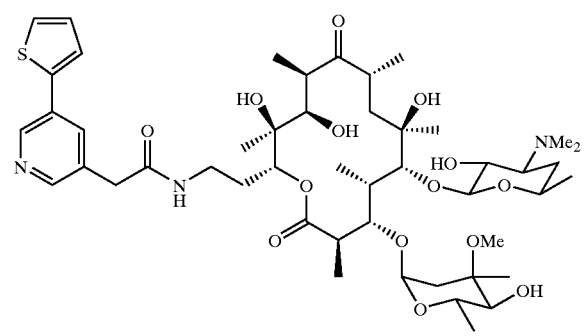

This compound is prepared according to the method of Example 6 using 3-(2-thienyl)-pyridyl-5-acetic acid.

EXAMPLE 39

15-(3-(2-pyrrolyl)pyridyl-5-acetamido)erythromycin A

This compound is prepared according to the method of Example 6 using 3-(2-pyrrolyl)-pyridyl-5-acetic acid.

EXAMPLE 40
15-(5-phenylthienyl-2-acetamido)erythromycin A
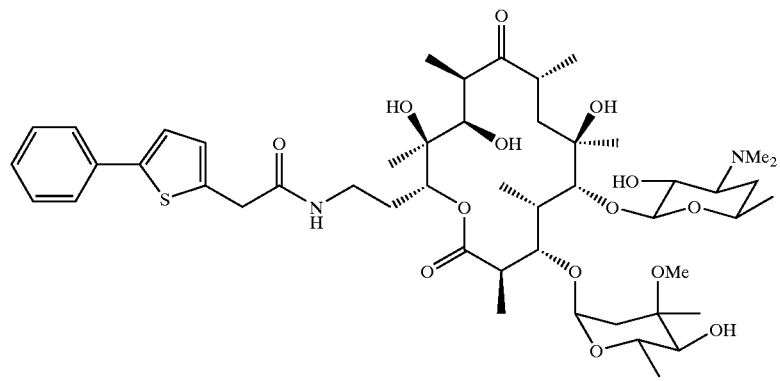
This compound is prepared according to the method of Example 6 using 5-phenylthienyl-2-acetic acid.
EXAMPLE 41
15-(5-(2-pyridyl)thienyl-2-acetamido)erythromycin A
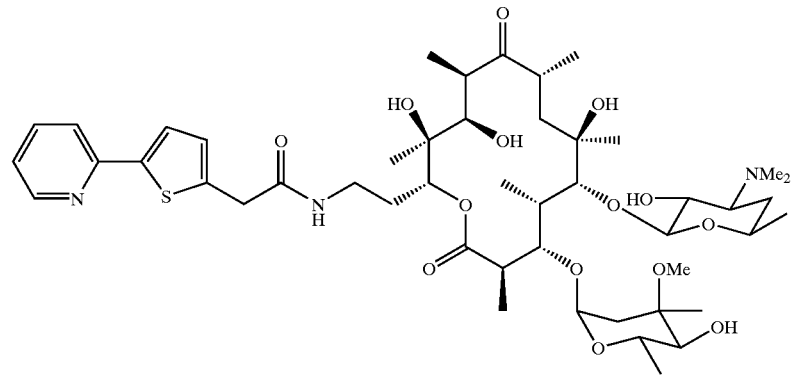
This compound is prepared according to the method of Example 6 using 5-(2-pyridyl)-thienyl-2-acetic acid.
EXAMPLE 42
15-(5-(3-isoxazolyl)thienyl-2-acetamido) erythromycin A
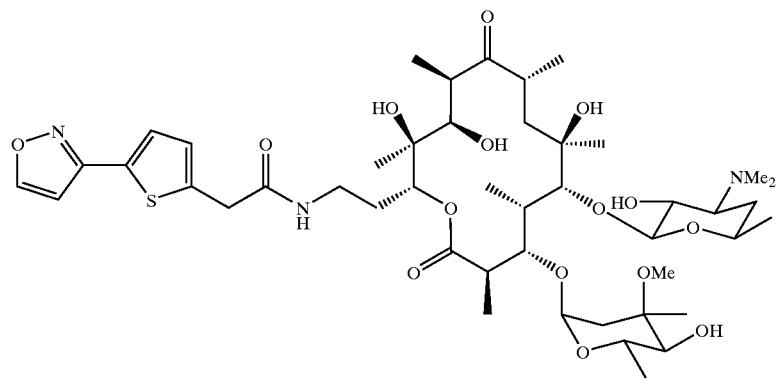

This compound is prepared according to the method of Example 6 using 5-(3-isoxazolyl)-thienyl-2-acetic acid.

EXAMPLE 43

15-(3-(5-phenylthien-2-yl)propionamido) erythromycin A

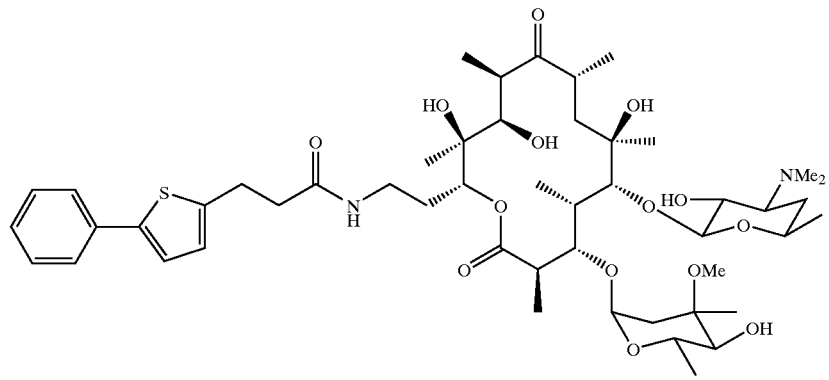

This compound was prepared according to the method of Example 6 using 3-(5-phenylthien-2-yl)propionic acid.

EXAMPLE 44

15-(3-(5-(2-pryidyl)thien-2-yl)propionamido) erythromycin A

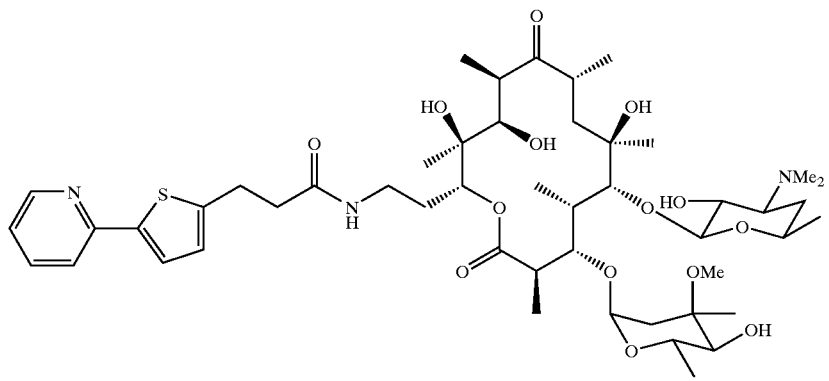

This compound is prepared according to the method of Example 6 using 3-(5-(2-pyridyl)thien-2-yl)propionic acid.

EXAMPLE 45

15-(3-(5-(3-isoxazolyl)thien-2-yl)propionamido) erythromycin A

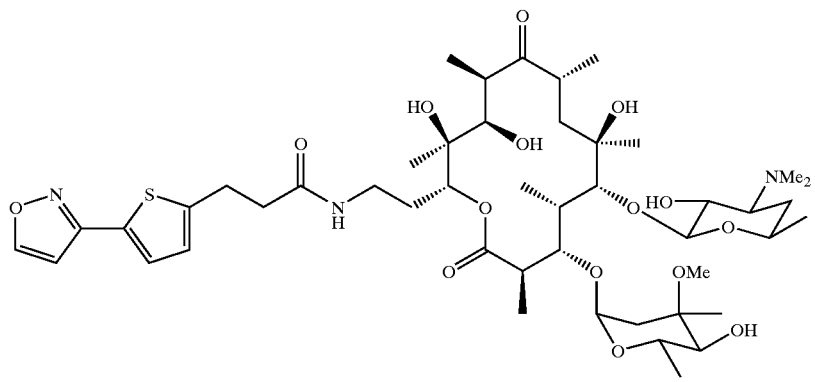

This compound is prepared according to the method of Example 6 using 3-(5-(3-isoxazolyl)-thien-2-yl)propionic acid.

EXAMPLE 46

General Preparation of Biaryl Carboxylic Acids

1. Biaryl Carboxylic Ester

To a solution of the haloaryl carboxylic ester (1.0 mmol) in tetrahydrofuran (15 mL) is added the boronic acid (1.3 mmol) and 2 M aq. sodium carbonate (1 mL). The solution is degassed and sonicated three times before adding tetrakis (triphenylphosphine)-palladium (0.1 mmol). The mixture is degassed and sonicated a further three times before stirring at 50° C. for 14 hours. After cooling to room temperature the solution is concentrated under reduced pressure. The product ester is purified by column chromatography.

2. Biaryl Carboxylic Acid

To a solution of the biaryl carboxylic ester (1.0 mmol) in acetone (15 mL) is added 30% aq. potassium hydroxide (2.5 mL). The mixture is stirred at room temperature for 16 hours before diluting with 1 N NaOH (50 ml), and washing with $CH_2Cl_2$ (75 ml). The aqueous phase is acidified with 1 N HCl (75 ml) and the organics extracted with $CH_2Cl_2$ (3×100 ml). The extract is dried ($Na_2SO_4$), filtered, and concentrated under reduced pressure to yield the biaryl carboxylic acid.

EXAMPLE 47

3-(2-furyl)phenylacetic acid

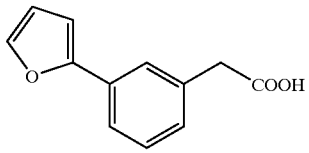

1. Methyl 3-(2-furyl)phenylacetate

To a solution of bromophenylacetic acid methyl ester (0.075 g, 0.328 mmol, 1.0 eq) in tetrahydrofuran (5.0 ml) was added 2-furanboronic acid (0.048 g, 0.426 mmol, 1.3 eq) and sodium carbonate (0.328 ml of a 2M soln in $H_2O$). The solution was degassed and sonicated three times before adding tetrakis(triphenylphosphine)palladium (0.038 g, 0.033 mmol, 0.1 eq). The mixture was degassed and sonicated a further three times before stirring at 50° C. for 14 hours. After cooling to room temperature the solution was concentrated under reduced pressure. Column chromatography (silica, 20% EtOAc/hexane) yielded 3-furanylphenylacetic acid methyl ester (0.047 g, 67%) as a white solid; $^1$H-NMR (CDCl$_3$, 400 MHz): δ 7.60 (1H, d, J=1.6 Hz), 7.47 (1H, t, J=1.0 Hz), 7.34 (1H, t, J=7.5 Hz), 7.19 (2H, m), 6.65 (1H, d, J=3.6 Hz), 6.48 (1H, dd, J=3.6, 1.6 Hz), 3.71 (3H, s), 3.66 (2H, s).

2. 3-(2-Furyl)phenylacetic acid

To a solution of 3-(2-furyl)phenylacetic acid methyl ester (0.047 g, 0.217 mmol, 1.0 eq) in acetone (3.0 ml) was added potassium hydroxide (0.5 ml of a 30% solution in $H_2O$). The mixture was stirred at room temperature for 16 hours before diluting with 1 N NaOH (10 ml), and washing with $CH_2Cl_2$ (15 ml). The aqueous phase was acidified with 1 N HCl (15 ml) and the organics extracted with $CH_2Cl_2$ (3×20 ml). The extract was dried ($Na_2SO_4$) and concentrated under reduced pressure to yield 3-(2-furyl)phenylacetic acid (0.043 g, 100%) as a white solid; $^1$H-NMR (CDCl$_3$, 400 MHz): δ 7.60 (1H, br s), 7.46 (1H, t, J=1.0 Hz), 7.34 (1H, t, J=7.5 Hz), 7.19 (2H, m), 6.65 (1H, d, J=3.2 Hz), 6.46 (1H, m), 3.67 (2H, s).

EXAMPLE 48

15-azidoerythromycin A 9-oxime

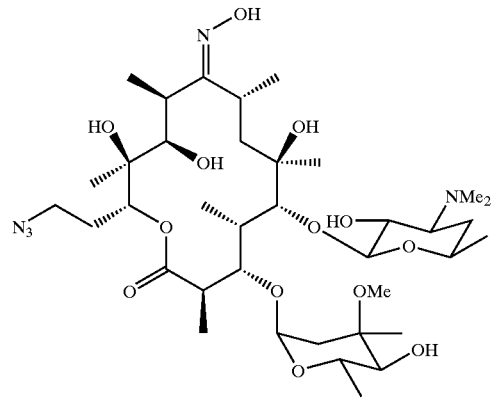

A mixture of 15-azidoerythromycin A (4.0 g) and 50% aqueous hydroxylamine (5.0 mL) in 10 mL of isopropanol was treated with 1.6 mL of acetic acid and stirred at 50° C. for 15 hours. The mixture was cooled to ambient temperature, treated with 20 mL of sat. aq. NaHCO$_3$, and concentrated under reduced pressure to an aqueous slurry, which was extracted with chloroform. The extract was washed with sat. aq. NaHCO$_3$ and brine, then dried over Na$_2$SO$_4$, filtered, and evaporated to yield 4.2 g of product. ES-MS: m/z 791 [M+H]$^+$.

EXAMPLE 49

15-azidoerythromycin A 9-oxime IPCH ketal

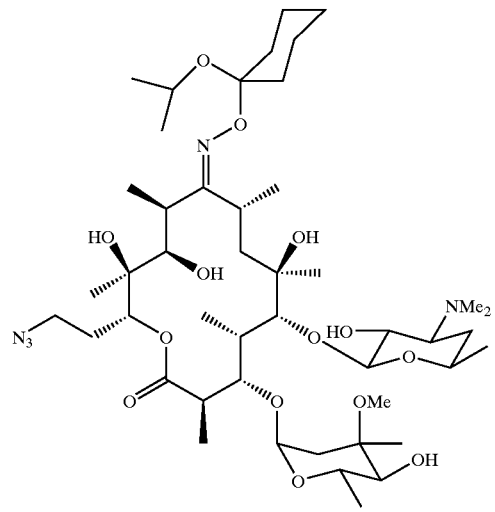

A mixture of 15-azidoerythromycin A 9-oxime (4.2 g), 1,1-diisopropoxycyclohexane (6.8 mL), and pyridinium p-toluenesulfonate (2.45 g) in 14 mL of dichloromethane was stirred at ambient temperature for 16 hours. The mixture was diluted with dichloromethane and washed with sat. aq. NaHCO$_3$ and brine, then dried over Na$_2$SO$_4$, filtered, and evaporated. The product was purified by silica gel chromatography (70:30 acetone/hexane+1% Et$_3$N) to yield 4.0 g of product. $^{13}$C-NMR (100 MHz, CDCl$_3$): δ 174.6, 104.2, 103.0, 96.3, 83.1, 78.0, 75.3, 74.0, 73.0, 72.7, 70.9, 70.2, 68.8, 65.5, 63.4, 61.9, 49.5, 49.2, 40.3, 36.0, 35.0, 27.0, 26.7, 25.7, 25.4, 24.7, 24.3, 23.4, 22.9, 21.5, 18.6, 18.5, 16.3, 15.8, 14.4, 9.2; ES-MS: m/z 931 [M+H]$^+$, 791.

EXAMPLE 50

2',4"bis-O-(trimethylsilyl)-15-azidoerythromycin A 9-oxime IPCH ketal

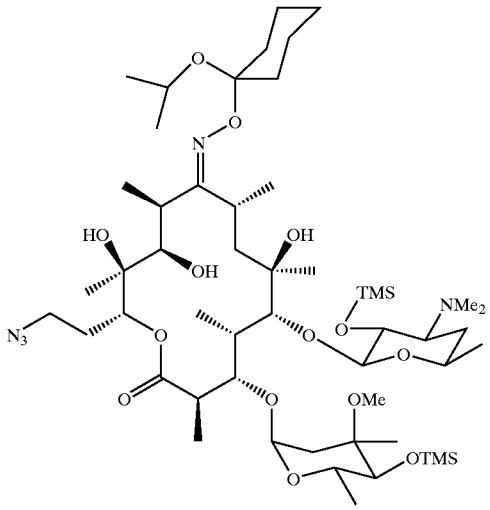

A solution of chlorotrimethylsilane (0.08 mL) and trimethylsilylimidazole (1.57 mL) in 4 mL of dichloromethane was added to a solution of 15-azidoerythromycin A 9-oxime IPCH ketal (4.0 g) in 12 mL of dichloromethane. After 5 minutes, 100 mL of ethyl acetate was added and the solution was washed with sat. aq. NaHCO$_3$ and brine, then dried over Na$_2$SO$_4$, filtered, and evaporated to give 4.2 g of product. $^{13}$C-NMR (100 MHz, CDCl$_3$): δ 175.4, 170.5, 135.2, 104.0, 102.6, 101.0, 96.6, 94.7, 80.8, 75.4, 73.9, 73.2, 73.1, 70.2, 67.6, 65.0, 64.9, 63.1, 61.7, 49.6, 49.1, 44.4, 40.8, 35.9, 26.9, 25.6, 24.6, 24.2, 23.3, 22.9, 21.9, 21.6, 19.2, 18.3, 16.2, 14.3, 9.6, 0.9, 0.8; ES-MS: m/z 1075 [M+H]$^+$.

EXAMPLE 51

2',4"bis-O-(trimethylsilyl)-6-O-azidoerythromycin A 9-oxime IPCH ketal

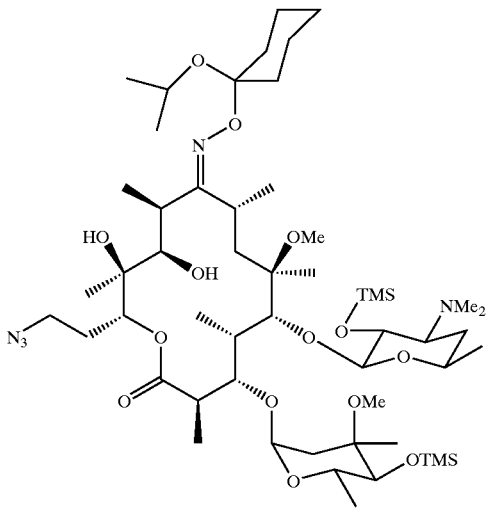

A mixture of 2',4"-bis-O-(trimethylsilyl)-15-azidoerythromycin A 9-oxime IPCH ketal (4.2 g), 2 M methyl bromide in ether (3.9 mL), 7 mL of THF, and 7 mL of DMSO was cooled on ice. A mixture of 1.0 M potassium tert-butoxide in DMSO (7.8 mL) and DMSO (7 mL) was added by syringe pump at a rate of 4 ml/hour, and the reaction was monitored by thin-layer chromatography (15% acetone in hexane, pretreating with ammonia vapor). The addition was continued for 3.5 hours before addition of sat. aq. NaHCO$_3$ (100 mL) and extracting the mixture with ethyl acetate. The extract was washed sequentially with NH$_4$Cl/NaCl, water, and brine, then dried over Na$_2$SO$_4$, filtered, and evaporated to yield 4.0 g of product. $^{13}$C-NMR (100 MHz, CDCl$_3$): δ 175.7, 169.8, 103.6, 102.5, 101.2, 96.2, 80.8, 79.1, 77.9, 73.6, 73.3, 73.1, 72.9, 69.7, 67.2, 65.1, 62.8, 61.8, 51.1, 49.7, 49.1, 40.9, 36.0, 26.5, 25.7, 25.6, 24.7, 24.5, 24.4, 23.4, 22.9, 22.2, 22.0, 20.2, 19.5, 18.6, 16.2, 15.1, 9.6, 1.0, 0.9. ES-MS: m/z 1089 [M+H]$^+$, 791.

EXAMPLE 52

6-O-methyl-15-azidoerythromycin A 9-oxime

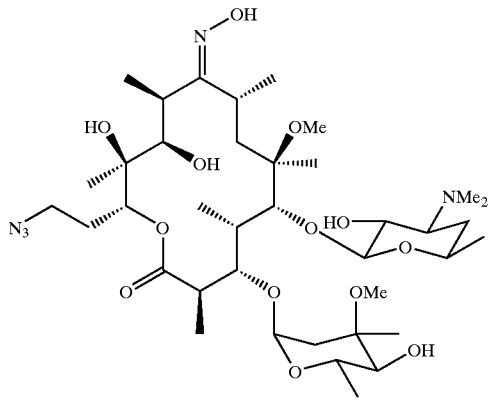

A solution of 2',4"-bis-O-(trimethylsilyl)-6-O-methyl-15-azidoerythromycin A 9-oxime IPCH ketal (4.0 g) in 50 mL of acetonitrile was treated with water (25 mL) and acetic acid (30 mL), the mixture was stirred for 16 hours at ambient temperature, and then concentrated under reduced pressure. The residue was concentrated from isopropanol and toluene to remove volatiles, then chromatographed on silica gel (1:1 acetone/hexanes+1% Et$_3$N) to yield 2.4 g of product. $^{13}$C-NMR (100 MHz, CDCl$_3$): δ 175.4, 171.2, 169.3, 102.7, 96.0, 80.3, 78.6, 78.2, 78.0, 77.5, 73.8, 72.8, 72.6, 71.3, 68.6, 65.5, 65.2, 60.4, 51.1, 49.4, 49.0, 45.7, 44.9, 40.3, 39.2, 25.3, 21.4, 21.4, 21.0, 20.0, 18.6, 18.6, 16.1, 15.7, 15.0, 9.1. ES-MS: m/z 805 [M+H]$^+$.

EXAMPLE 53

6-O-methyl-15-azidoerythromycin A

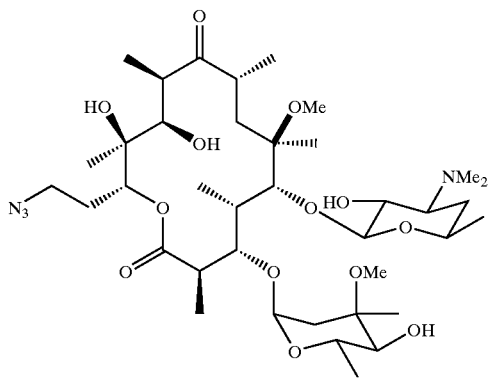

A solution of 15-azidoerythromycin A 9-oxime (2.4 g) in 25 mL of ethanol was treated with 25 mL of water, sodium hydrosulfite (4.8 g), and formic acid (0.77 ml) and heated to 80° C. After 4 hours, the mixture was cooled to ambient temperature, adjusted to pH 10 using 6 N NaOH, and extracted with ethyl acetate. The extract was washed with brine, dried over $Na_2SO_4$, filtered, and evaporated to yield 2.4 g of product. $^{13}$C-NMR (100 MHz, $CDCl_3$): δ 221.3, 175.6, 102.8, 96.1, 80.7, 78.4, 78.3, 78.0, 74.0, 72.7, 72.7, 70.9, 68.8, 65.8, 65.6, 50.6, 49.5, 49.1, 45.2, 45.0, 40.2, 39.4, 37.1, 34.9, 28.6, 27.7, 21.5, 19.7, 18.7, 17.9, 16.0, 15.6, 12.3, 9.0. ES-MS: m/z 790 $[M+H]^+$.

EXAMPLE 54

3-O-descladinosyl-6-O-methyl-15-azidoerythromycin A

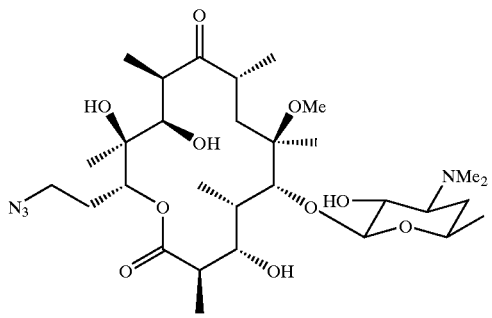

A mixture of 6-O-methyl-15-azidoerythromycin A (2.0 g) and pyridinium p-toluenesulfonate (3.82 g) in 20 mL of acetone and 5 mL of water was stirred at 50° C. for 44 hours, then cooled to ambient temperature and treated with sat. aq. $NaHCO_3$ and extracted with ethyl acetate. The extract was washed with brine, dried over $Na_2SO_4$, filtered, and evaporated. The residue was chromatographed on silica gel to yield product (0.5 g) and unreacted starting material, which was recycled through the procedure. $^{13}$C-NMR (100 MHz, $CDCl_3$): δ 220.5, 174.7, 106.4, 88.1, 78.7, 78.0, 74.0, 72.7, 70.6, 70.0, 69.4, 65.6, 49.5, 49.0, 48.8, 45.4, 44.4, 40.4, 40.2, 38.7, 35.4, 29.2, 28.7, 28.0, 21.2, 21.0, 18.7, 18.3, 17.7, 16.2, 15.1, 15.0, 12.5, 8.2. ES-MS: m/z 632 $[M+H]^+$.

EXAMPLE 55

2'-O-benzoyl-3-O-descladinosyl-6-O-methyl-15-azidoerythromycin A

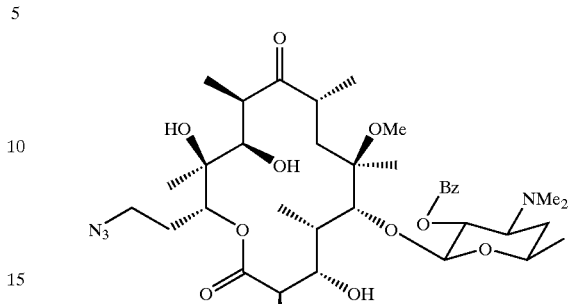

To a solution of 3-O-descladinosyl-6-O-methyl-15-azidoerythromycin A (0.6 g, 0.951 mmol, 1.0 eq) in dichloromethane (10 ml) was added benzoic anhydride (0.32 g, 1.426 mmol, 1.5 eq) and the mixture stirred at room temperature for 14 hours. Sat. aq. $NaHCO_3$ (30 ml) was added and the organics extracted with $CH_2Cl_2$ (3×30 ml). The combined organics were dried ($Na_2SO_4$), filtered, and concentrated under reduced pressure to yield a pale yellow oil, which was taken on without further purification; ES-MS: m/z 736 $[M+H]^+$.

EXAMPLE 56

2'-O-benzoyl-3-des(cladinosyloxy)-3-oxo-6-O-methyl-15-azidoerythromycin A

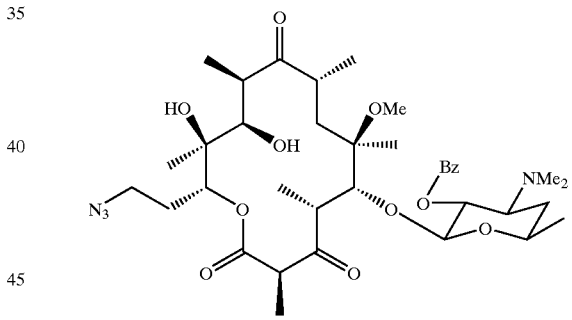

N-Chlorosuccinimide (0.191 g, 1.427 mmol, 1.5 eq) was added to a solution of dimethyl sulfide (0.085 ml, 1.712 mmol, 1.8 eq) and dichloromethane (5 ml) at −15° C. After stirring at −15° C. for 15 minutes, 2'-O-benzoyl-3-O-descladinosyl-6-O-methyl-15-azidoerythromycin A (0.951 mmol, 1.0 eq) in dichloromethane (5 ml) was added dropwise and the resulting solution was stirred at −15° C. for 30 minutes before adding triethylamine (0.132 ml, 0.951 mmol, 1.0 eq). The mixture was warmed to room temperature over 40 minutes before diluting with EtOAc (100 ml) and washing with sat. aq. $NaHCO_3$ (2×100 ml) and brine (100 ml). The organics were dried ($Na_2SO_4$), filtered, and concentrated under reduced pressure. The product was purified by silica gel chromatography (0→10 min 20% acetone-hexane, 1% $Et_3N$; 10→20 min 30% acetone-hexane, 1% $Et_3N$; 20+min 40% acetone-hexane, 1% $Et_3N$) to provide the product (0.5 g, 72% over two steps) as a white solid; $^{13}$C-NMR (100 MHz, $CDCl_3$): δ 220.8, 205.0, 169.0, 165.2, 132.8, 130.4, 129.7, 128.3, 101.3, 74.2, 73.6, 71.9, 69.1, 68.9, 63.6, 53.5, 50.7, 49.5, 49.1, 46.4, 44.8, 41.5, 40.7, 39.0, 37.2, 31.3, 28.2, 27.8, 21.0, 19.4, 17.5, 16.2, 14.3, 12.0. ES-MS: m/z 734 [M+H]$^+$.

EXAMPLE 57

2'-O-benzoyl-3-des(cladinosyloxy)-3-oxo-6-O-methyl-11-O-methanesulfonyl-15-azidoerythromycin A

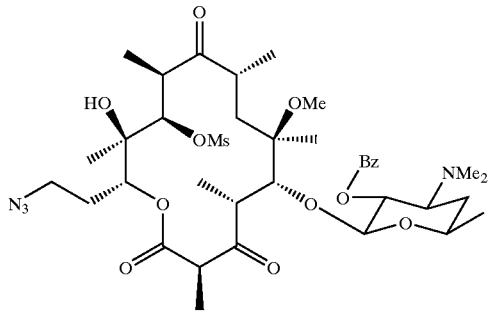

To a solution of 2'-O-benzoyl-3-des(cladinosyloxy)-3-oxo-6-O-methyl-15-azidoerythromycin A (0.5 g, 0.683 mmol, 1.0 eq) in pyridine (7.0 eq) was added methanesulfonyl chloride (0.26 ml, 3.415 mmol, 5.0 eq) dropwise. The resulting solution was stirred at room temperature for 16 hours before diluting with ethyl acetate (100 ml) and washing with sat. aq. NaHCO$_3$ (2×70 ml) and brine (70 ml). The organics were dried (Na$_2$SO$_4$), filtered, and concentrated under reduced pressure to yield product as a brown solid (0.5 g) which was taken on without further purification.

EXAMPLE 58

2'-O-benzoyl-10,11-anhydro-3-des(cladinosyloxy)-3-oxo-6-O-methyl-15-azidoerythromycin A

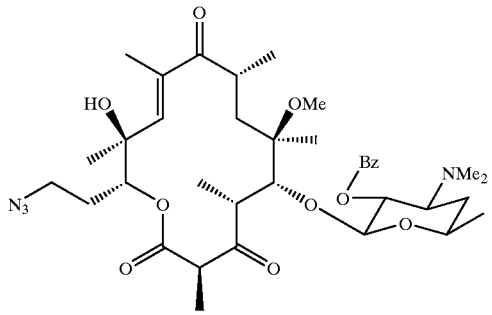

To a solution of 2'-O-benzyl-3-des(cladinosyloxy)-3-oxo-6-O-methyl-11-O-methanesulfonyl-15-azidoerythromycin A (0.683 mmol, 1.0 eq) in acetone (7.0 ml) was added 1,8-diazabicyclo[5.4.0]undec-7-ene (0.510 ml, 3.415 mmol, 5.0 eq) and the solution stirred at room temperature for 8 hours before concentrating under reduced pressure. Purification by silica gel chromatography (0→10 min 25% acetone-hexane, 1% Et$_3$N; 10→20 min 30% acetone-hexane, 1% Et$_3$N; 20→30 min 35% acetone-hexane, 1% Et$_3$N; 30+min 40% acetone-hexane, 1% Et$_3$N) yielded the product (0.25 g, 50% over two steps) as a white solid; $^{13}$C-NMR (100 MHz, CDCl$_3$): δ 206.8, 176.4, 169.4, 165.1, 141.5, 139.2, 132.7, 130.5, 129.7, 128.3, 102.1, 78.4, 72.7, 72.0, 69.2, 63.7, 51.0, 50.4, 49.0, 47.1, 41.5, 40.7, 40.1, 38.3, 31.6, 31.2, 29.0, 28.2, 22.6, 21.5, 21.0, 18.6, 14.5, 14.2, 13.6. ES-MS: m/z 716 [M+H]$^+$.

EXAMPLE 59

2'-O-benzoyl-11-amino-11-deoxy-3-O-des(cladinosyloxy)-3-oxo-6-O-methyl-15-azidoerythromycin A 11,12-cyclic carbamate

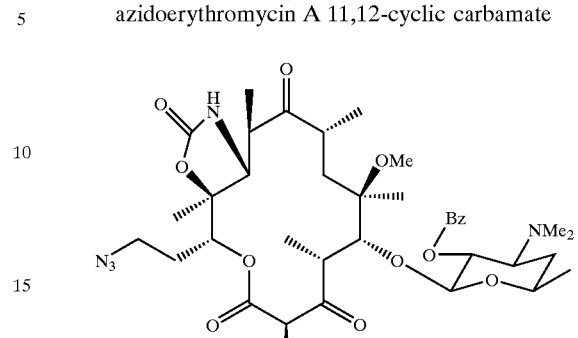

To a solution of 2'-O-benzoyl-10,11-anhydro-3-O-des(cladinosyloxy)-3-oxo-6-O-methyl-15-azidoerythromycin A (0.246 g, 0.344 mmol, 1.0 eq) in tetrahydrofuran (3.0 ml) at −15° C. was added sodium hydride (0.028 g of a 60% soln. in oil, 0.688 mmol, 2.0 eq). The solution was stirred at −15° C. for 15 minutes before adding a solution of 1,1-carbonyldiimidazole (0.167 g, 1.032 mmol, 3.0 eq) in tetrahydrofuran (3.0 ml) dropwise. The solution was stirred at −15° C. for 15 minutes before warming to room temperature over a period of 40 minutes. Sat. aq. NaHCO$_3$ (25 ml) was added followed by ethyl acetate (50 ml), and the solution was partitioned. The organics were further washed with sat. aq. NaHCO$_3$ (25 ml) and brine (25 ml) before drying (Na$_2$SO$_4$), filtering, and concentrating under reduced pressure. The residue was dissolved in a mixture of acetonitrile and tetrahydrofuran (10:1, 4 ml) and conc. ammonium hydroxide (4 ml) was added. The mixture was stirred at room temperature for 16 hours before diluting with ethyl acetate (50 ml) and washing with sat. aq. NaHCO$_3$ (2×25 ml) and brine (30 ml). The organics were dried (Na$_2$SO$_4$), filtered, and concentrated under reduced pressure. Silica gel chromatography (0→10 min 25% acetone-hexane, 1% Et$_3$N; 10→20 min 30% acetone-hexane, 1% Et$_3$N; 20→30 min 35% acetone-hexane, 1% Et$_3$N; 30+min 40% acetone-hexane, 1% Et$_3$N) yielded the product as a white solid; ES-MS: m/z 759 [M+H]$^+$.

EXAMPLE 60

2'-O-benzoyl-11-amino-11-deoxy-3-des(cladinosyloxy)-2-fluoro-3-oxo-6-O-methyl-15-azidoerythromycin A 11,12-cyclic carbamate

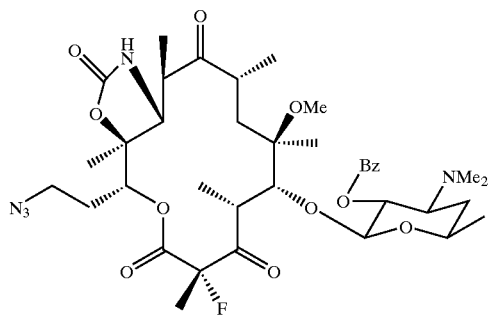

A solution of 2'-O-benzoyl-11-amino-11-deoxy-3-des(cladinosyloxy)-3-oxo-6-O-methyl-15-azidoerythromycin A 11,12-cyclic carbamate (1.0 eq) in THF is cooled on ice and treated with a 1 M solution of potassium tert-butoxide in THF (1.0 eq.), followed by N-fluoro-benzenesulfonimide (1.2 eq). After 1 hour, the mixture is warmed to ambient temperature and poured into a mixture of ethyl acetate and sat. aq. NH$_4$Cl. The organic phase is washed with brine, dried over MgSO$_4$, filtered, and evaporated. The product is purified by silica gel chromatography (acetone/hexanes+1% Et$_3$N).

EXAMPLE 61

2'-O-benzoyl-11-amino-11-deoxy-3-des (cladinosyloxy)-3-oxo-6-O-methyl-15-(3-(2-furyl) phenylacetamido)erythromycin A 11,12-cyclic carbamate

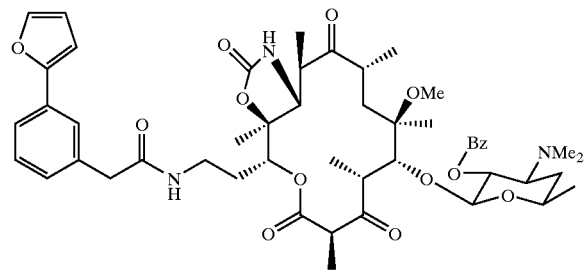

To a solution of 2'-O-benzoyl-11-amino-11-deoxy-3-des (cladinosyloxy)-3-oxo-6-O-methyl-15-azidoerythromycin A 11,12-cyclic carbamate (0.050 g, 0.062 mmol, 1.0 eq) in dichloromethane (1.0 ml) was added trimethylphosphine (0.31 ml of a 1M solution in THF, 0.306 mmol, 5.0 eq). The solution was stirred at room temperature for 45 minutes before transferring to a solution of the carboxylic acid (0.092 mmol, 1.5 eq), 1-[(3-(dimethylamino)propyl]-1-ethylcarbodiimide hydrochloride (0.019 g, 0.099 mmol, 1.6 eq) and 1-hydroxybenzotriazole (0.017 g, 0.124 mmol, 2.0 eq) in dichloromethane (1.0 ml) also stirred at room temperature for 45 minutes. The resulting solution was stirred at room temperature for 14 hours before partitioning between ethyl acetate (10 ml) and NaHCO$_3$ (10 ml). The aqueous phase was extracted with ethyl acetate (3×10 ml) and the combined organics further washed with brine (25 ml) before drying (Na$_2$SO$_4$), filtering, and concentrating under reduced pressure. The product was purified by silica gel chromatography using acetone/hexane+1% Et$_3$N.

EXAMPLE 62

11-amino-11-deoxy-3-des(cladinosyloxy)-3-oxo-6-O-methyl-15-(3-(2-furyl)phenylacetamido) erythromycin A 11,12-cyclic carbamate

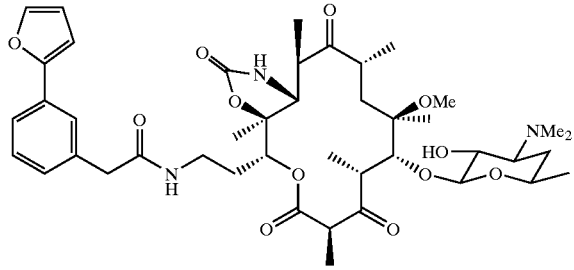

A mixture of 2'-O-benzoyl-11-amino-11-deoxy-3-des (cladinosyloxy)-3-oxo-6-O-methyl-15-(3-(2-furyl) phenylacetamido)erythromycin A 11,12-cyclic carbamate and triethylamine in methanol was heated at 50° C. overnight, then evaporated to dryness. The product was purified by silica gel chromatography (acetone/hexanes+1% Et$_3$N).

EXAMPLE 63

2'-O-benzoyl-11-amino-11-deoxy-3-des (cladinosyloxy)-2-fluoro-3-oxo-6-O-methyl-15-(3-(2-furyl)phenylacetamido)erythromycin A 11,12-cyclic carbamate

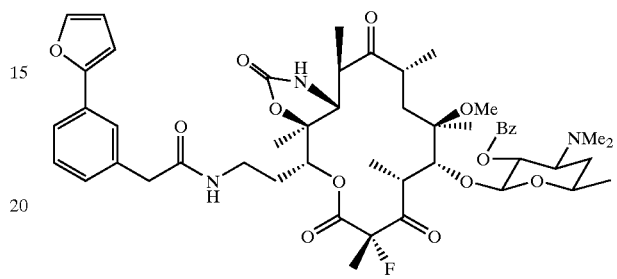

To a solution of 2'-O-benzoyl-11-amino-11-deoxy-3-des (cladinosyloxy)-2-fluoro-3-oxo-6-O-methyl-15-azidoerythromycin A 11,12-cyclic carbamate (0.050 g, 0.062 mmol, 1.0 eq) in dichloromethane or tetrahydrofuran (1.0 ml) is added trimethylphosphine (0.31 ml of a 1M solution in THF, 0.306 mmol, 5.0 eq). The solution is stirred at room temperature for 45 minutes before transferring to a solution of the carboxylic acid (0.092 mmol, 1.5 eq), 1-[(3-(dimethylamino)propyl]-1-ethylcarbodiimide hydrochloride (0.019 g, 0.099 mmol, 1.6 eq) and 1-hydroxybenzotriazole (0.017 g, 0.124 mmol, 2.0 eq) in dichloromethane or tetrahydrofuran (1.0 ml) also stirred at room temperature for 45 minutes. The resulting solution is stirred at room temperature for 14 hours before partitioning between ethyl acetate (10 ml) and NaHCO$_3$ (10 ml). The aqueous phase is extracted with ethyl acetate (3×10 ml) and the combined organics further washed with brine (25 ml) before drying (Na$_2$SO$_4$), filtering, and concentrating under reduced pressure. The product is purified by silica gel chromatography using acetone/hexane+1% Et$_3$N.

EXAMPLE 64

11-amino-11-deoxy-3-des(cladinosyloxy)-2fluoro-3-oxo-6-O-methyl-15-(3-(2-furyl)phenylacetamido) erythromycin A 11,12-cyclic carbamate

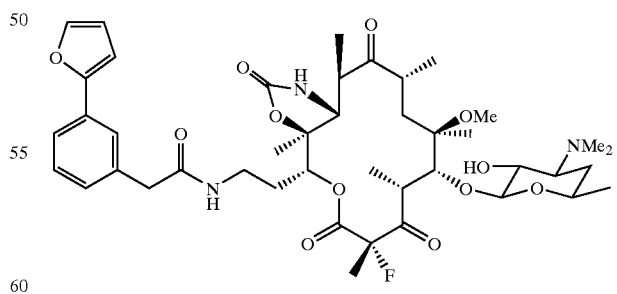

A solution of 2'-O-benzoyl-11-amino-11-deoxy-3-des (cladinosyloxy)-3-oxo-6-O-methyl-15-(3-(2-furyl) phenylacetamido)erythromycin A 11,12-cyclic carbamate and triethylamine in methanol is heated at 50° C. overnight, then evaporated to dryness. The product is purified by silica gel chromatography (acetone/hexanes+1% Et$_3$N).

EXAMPLE 65

2'-O-benzoyl-3-des(cladinosyloxy)-3-oxo-6-O-methyl-15-(3-(2-furyl)phenylacetamido)erythromycin A

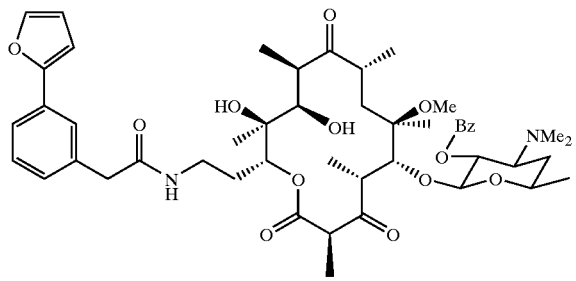

To a solution of 2'-O-benzoyl-3-des(cladinosyloxy)-3-oxo-6-O-methyl-15-azidoerythromycin A (0.045 g, 0.062 mmol, 1.0 eq) in dichloromethane or tetrahydrofuran (1.0 ml) is added trimethylphosphine (0.31 ml of a 1M solution in THF, 0.306 mmol, 5.0 eq). The solution is stirred at room temperature for 45 minutes before transferring to a solution of the carboxylic acid (0.092 mmol, 1.5 eq), 1-[(3-(dimethylamino)propyl]-1-ethylcarbodiimide hydrochloride (0.019 g, 0.099 mmol, 1.6 eq) and 1-hydroxybenzotriazole (0.017 g, 0.124 mmol, 2.0 eq) in dichloromethane or tetrahydrofuran (1.0 ml) also stirred at room temperature for 45 minutes. The resulting solution is stirred at room temperature for 14 hours before partitioning between ethyl acetate (10 ml) and NaHCO$_3$ (10 ml). The aqueous phase is extracted with ethyl acetate (3×10 ml) and the combined organics further washed with brine (25 ml) before drying (Na$_2$SO$_4$), filtering, and concentrating under reduced pressure. The product is purified by silica gel chromatography using acetone/hexane+1% Et$_3$N.

EXAMPLE 66

3-des(cladinosyloxy)-3-oxo-6-O-methyl-15-(3-(2-furyl)phenylacetamido)erythromycin A

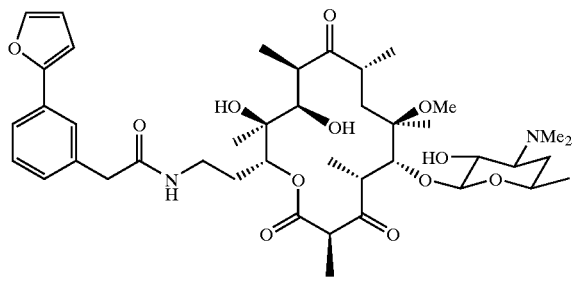

A mixture of 2'-O-benzoyl-3-des(cladinosyloxy)-3-oxo-6-O-methyl-15-(3-(2-furyl)phenylacetamido)erythromycin A and triethylamine in methanol is heated at 50° C. overnight, then evaporated to dryness. The product is purified by silica gel chromatography (acetone/hexanes+1% Et$_3$N).

EXAMPLE 67

2'-O-acetyl-3-des(cladinosyloxy)-3-oxo-6-O-methyl-15-(3-(2-furyl)phenylacetamido)erythromycin A 11,12-cyclic carbonate

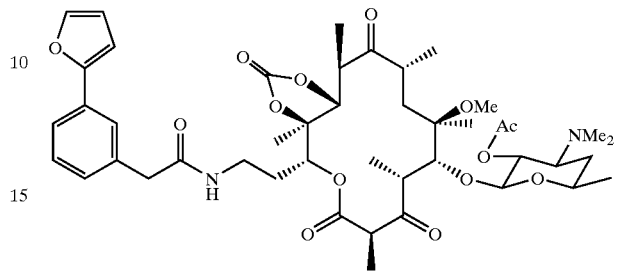

To a solution of 2'-O-acetyl-3-des(cladinosyloxy)-3-oxo-6-O-methyl-15-azidoerythromycin A 11,12-cyclic carbonate (0.043 g, 0.062 mmol, 1.0 eq) in dichloromethane or tetrahydrofuran (1.0 ml) is added trimethylphosphine (0.31 ml of a 1M solution in THF, 0.306 mmol, 5.0 eq). The solution is stirred at room temperature for 45 minutes before transferring to a solution of the carboxylic. acid (0.092 mmol, 1.5 eq), 1-[(3-(dimethylamino)propyl]-1-ethylcarbodiimide hydrochloride (0.019 g, 0.099 mmol, 1.6 eq) and 1-hydroxybenzotriazole (0.017 g, 0.124 mmol, 2.0 eq) in dichloromethane or tetrahydrofuran (1.0 ml) also stirred at room temperature for 45 minutes. The resulting solution is stirred at room temperature for 14 hours before partitioning between ethyl acetate (10 ml) and NaHCO$_3$ (10 ml). The aqueous phase is extracted with ethyl acetate (3×10 ml) and the combined organics further washed with brine (25 ml) before drying (Na$_2$SO$_4$), filtering, and concentrating under reduced pressure. The product is purified by silica gel chromatography using acetone/hexane+1% Et$_3$N.

EXAMPLE 68

3-des(cladinosyloxy)-3-oxo-6-O-methyl-15-(3-(2-furyl)phenylacetamido)erythromycin A 11,12-cyclic carbomate

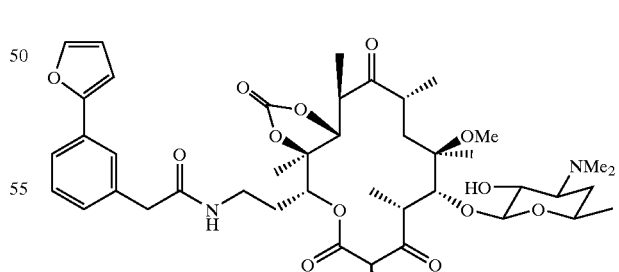

A solution of 2'-O-acetyl-3-des(cladinosyloxy)-3-oxo-6-O-methyl-15-(3-(2-furyl)phenylacetamido)erythromycin A 11,12-cyclic carbonate in methanol is heated at 50° C. for 16 hours, then evaporated to dryness. The product is purified by silica gel chromatography (acetone/hexane+1% Et$_3$N).

EXAMPLE 69

(±)-(2S*,3R*)-4-chloro-3-hydroxy-2-methylbutanoate N-propionylcysteamine thioester

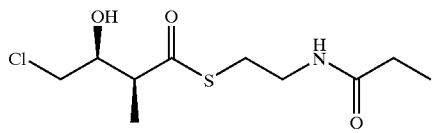

This is prepared according to the method of Example 1, substituting chloroacetaldehyde in place of 3-chloropropanal.

EXAMPLE 70

(±)-(2S*,3R*)-4-chloro-3-hydroxy-2-methylbutanoate N-propionylcysteamine thioester

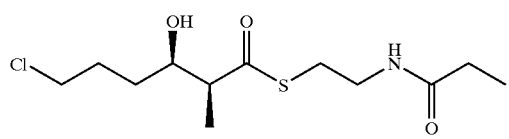

This is prepared according to the method of Example 1, substituting chlorobutyraldehyde in place of 3-chloropropanal.

EXAMPLE 71

14-chloro-14-desmethyl-6-deoxyerythronolide B

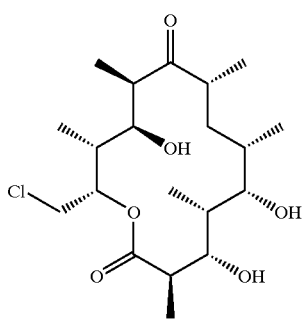

This is prepared according to the method of Example 2, substituting (±)-(2S*,3R*)-4-chloro-3-hydroxy-2-methylbutanoate N-propionylcysteamine thioester in place of (±)-(2S*,3R*)-5-chloro-3-hydroxy-2-methylpentanoate N-propionylcysteamine thioester.

EXAMPLE 72

14-chloro-14-desmethyl-erythronolide B

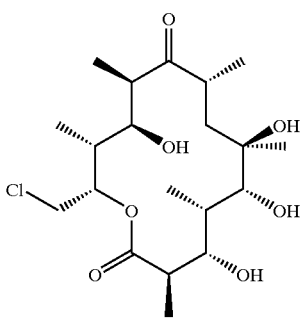

This is prepared according to the method of Example 2, substituting (±)-(2S*,3R*)-4-chloro-3-hydroxy-2-methylbutanoate N-propionylcysteamine thioester in place of (±)-(2S*,3R*)-5-chloro-3-hydroxy-2-methylpentanoate N-propionylcysteamine thioester, and substituting *Streptomyces coelicolor* CH999/p23–55/pJRJ2, a strain containing the eryF gene on the chromosome along with plasmid pJRJ2, in place of *Streptomyces coelicolor* CH999/pJRJ2. $^{13}$C-NMR (CDCl$_3$+CD$_3$OD, 100 MHz): δ 218.6, 176.2, 81.1, 79.2, 74.9, 73.0, 69.7, 44.7, 43.7, 43,7, 39.7, 38.6, 38.1, 36.0, 25.8, 17.4, 14.6, 9.2, 8.6, 6.9.

EXAMPLE 73

15-(chloromethyl)-6-deoxyerythronolide B

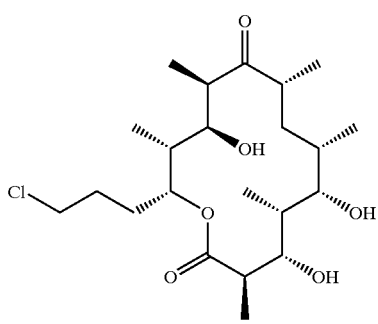

This is prepared according to the method of Example 2, substituting (±)-(2S*,3R*)-6-chloro-3-hydroxy-2-methylhexanoate N-propionylcysteamine thioester in place of (±)-(2S*,3R*)-5-chloro-3-hydroxy-2-methylpentanoate N-propionylcysteamine thioester.

EXAMPLE 74

14-azido-14-desmethyl-6-deoxyerythronolide B

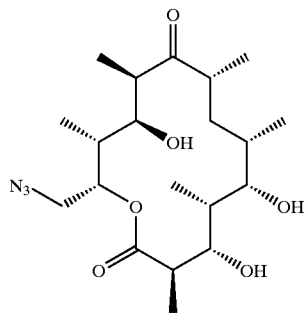

This is prepared according to the method of Example 3, substituting 14-chloro-14-desmethyl-6-deoxyerythronolide B in place of 15-chloro-6-deoxyerythronolide B.

EXAMPLE 75

14-(azidomethyl)-6-deoxyerythronolide B

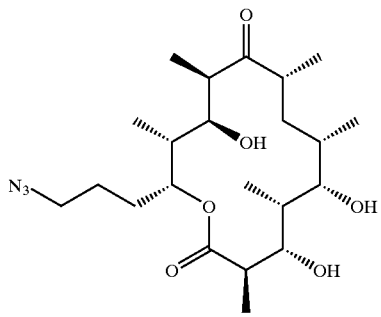

This is prepared according to the method of Example 3, substituting 15-(chloromethyl)-6-deoxyerythronolide B in place of 15-chloro-6-deoxyerythronolide B.

EXAMPLE 76

14-azido-14-desmethyl-erythromycin A

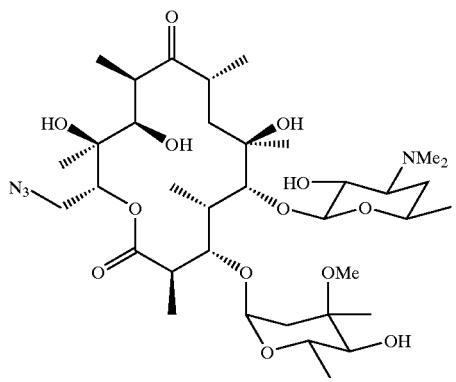

This is prepared according to the method of Example 4, substituting 14-azido-14-desmethyl-6-deoxyerythronolide B or 14-azido-14-desmethylerythronolide B in place of 15-azido-6-deoxyerythronolide B.

EXAMPLE 77

15-(azidomethyl)-erythromycin A

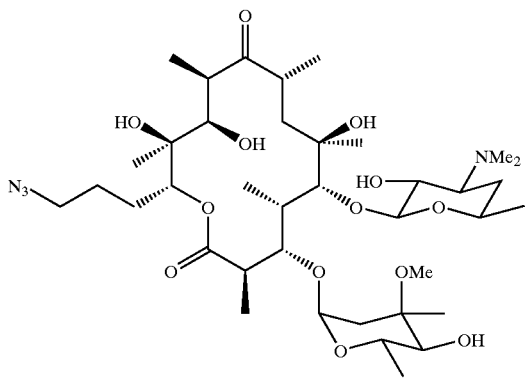

This is prepared according to the method of Example 4, substituting 15-(azidomethyl)-6-deoxyerythronolide B in place of 15-azido-6-deoxyerythronolide B.

EXAMPLE 78

15-((6-methoxy-1-benzofuran-3-yl)acetamido) erythromycin A

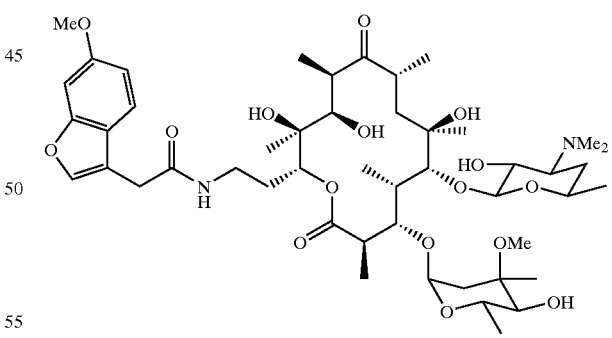

This compound was prepared according to the method of Example 6 using 2-(6-methoxy-1-benzofuran-3-yl)acetic acid. $^{13}$C-NMR (100 MHz, CDCl$_3$): δ 222.1, 176.3, 169.8, 158.3, 156.5, 142.3, 120.8, 119.8, 113.8, 111.8, 103.1, 96.5, 83.1, 79.4, 78.0, 75.0, 74.2, 72.6, 70.8, 69.0, 68.8, [65.6, 65.6] (2C), 55.7, 49.5, 46.0, 45.1, 44.6, 40.3, 40.0, 38.4, 37.9, 36.2, 34.9, 31.8, 29.7, 28.6, 28.3, 26.9, 21.5, 21.4, 18.6, 18.1, 16.1, 15.3, 11.8, 9.0.

EXAMPLE 79

15-((5-chlorobenzo[b]thiophen-3-yl)acetamido)erythromycin A

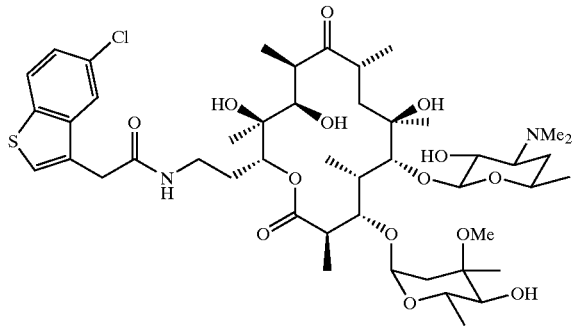

This compound was prepared according to the method of Example 6 using 2-(5-chlorobenzo[b]thiophen-3-yl)acetic acid. $^{13}$C-NMR (100 MHz, CDCl$_3$): δ 222.0, 169.4, 139.8, 138.6, 130.8, 129.0, 126.9, 125.0, 123.8, 121.5, 103.1, 96.3, 83.1, 79.4, 77.3, 75.1, 74.2, 72.7, 72.6, 70.8, 69.0, 68.9, 49.5, 45.1, 44.6, 40.3, 44.6, 40.3, 40.0, 38.4, 37.9, 36.5, 36.2, 34.9, 29.7, 29.3, 28.6, 28.4, 26.9, 21.5, 21.4, 18.6, 18.1, 16.1, 15.4, 11.9, 9.0.

EXAMPLE 80

6-O-methyl-15-azidoerythromycin A (a) Formation of 15-azidoerythromycin A 9-oxime.

A suspension of 15-azido-erythromycin A (33.0 g, 90% purity, 42.5 mmol) in 90 ml of 2-propanol was treated with 32.0 ml of 50% aqueous hydroxylamine and stirred while acetic acid (10.30 ml) was added and the mixture was stirred for 15 hours at 50° C. The reaction can be followed by thin-layer chromatography (10:1:0.05/CHCl$_3$/MeOH/MH$_4$OH). Upon cooling to ambient temperature, saturated NaHCO$_3$ was added and the mixture was concentrated in vacuo to remove isopropanol. The resulting aqueous mixture was extracted three times with 300-ml portions of CHCl$_3$. The organic extracts were combined, washed with saturated NaHCO$_3$, water, and brine, then dried over MgSO$_4$, filtered, and concentrated to yield 34 g of crude product. Analysis by LC/MS revealed no clean separation of E and Z oximes, [M+H]$^+$=791. $^{13}$C NMR (CDCl$_3$, 100 MHz) δ 175.1, 171.3, 103.1, 96.4, 83.4, 80.1, 78.1, 75.3, 74.2, 73.2, 72.6, 71.1, 70.6, 68.7, 65.5, 65.4, 49.5, 49.1, 44.6, 40.2, 39.0, 37.8, 35.1, 32.6, 29.7, 29.4, 29.2, 27.6, 27.0, 25.5, 22.6, 21.5, 21.3, 18.6, 16.4, 15.9, 14.3, 9.2.

(b) Oxime Protection.

The crude oxime from step (a) above (34.0 g, 42.5 mmol) was suspended in 120 ml of CH$_2$Cl$_2$ and treated with 1,1-diisopropoxycyclohexane (51.0 ml, 246.8 mmol, 6 eq.) and pyridinium p-toluenesulfonate (24.8 g, 98.8 mmol, 2 eq.) for 15 hours at ambient temperature. The mixture was diluted with 600 ml of CH$_2$Cl$_2$, and then washed sequentially with saturated NaHCO$_3$, water, and brine. The organic phase was dried with MgSO$_4$, filtered, and evaporated to yield brown syrup. Chromatography on silica gel (gradient from 2:1 to 1:1 hexanes/acetone+1% Et$_3$N) yielded 32 g of product. $^{13}$C NMR (CDCl$_3$, 100 MHz) δ 174.6, 170.2, 104.2, 103.0, 96.3, 83.1, 78.0, 77.4, 75.2, 74.0, 73.0, 72.6, 70.9, 70.2, 68.8, 65.5, 63.4, 61.9, 49.5, 49.2, 44.5, 40.3, 39.2, 37.8, 36.0, 35.0, 33.4, 33.0, 28.6, 27.7, 27.0, 26.7, 25.7, 25.4, 24.7, 24.3, 23.4, 22.9, 21.5, 18.6, 18.5, 16.3, 15.8, 14.4, 9.2.

(c) Trimethylsilylation.

A solution of 15-azidoerythromycin A 9-[O-(1-isopropoxy-cyclohexyl)]oxime (32.00 g, 34.4 mmol) in 120 ml of CH$_2$Cl$_2$ was cooled on ice under inert atmosphere and treated with a solution of chlorotrimethylsilane (0.628 ml, 4.95 mmol, 0.15 eq.)) and 1-trimethylsilylimidazole (12.1 ml, 82.6 mmol, 2.4 eq.) in 30 ml of CH$_2$Cl$_2$. After 5 minutes, the reaction was diluted with 1L of ethyl acetate and washed sequentially with saturated NaHCO$_3$, water, and brine. The organic phase was dried with MgSO$_4$, filtered, and evaporated. The crude product was purified by silica gel chromatography (gradient from hexanes to 10:1 hexanes/acetone+1% Et$_3$N), yielding 29 g of product. $^{13}$C NMR (CDCl$_3$, 100 MHz) δ 175.5, 170.5, 104.1, 102.7, 96.8, 81.4, 80.9, 79.2, 75.6, 74.0, 73.3, 73.2, 70.3, 67.8, 65.2, 65.0, 63.2, 49.7, 49.2, 44.5, 41.0, 38.3, 35.8, 34.4, 33.6, 33.2, 31.6, 29.8, 28.1, 26.7, 25.4, 24.3, 22.9, 22.6, 22.1, 21.7, 19.3, 18.4, 16.3, 15.1, 14.4, 14.1, 9.7, 1.0, 0.9.

(d) Methylation.

To a solution of 29 g of fully protected oxime from step (c) above (27.0 mmol) in a mixture of 55 ml of freshly distilled THF and 55 ml of dry DMSO was added 27.05 ml of a 2N solution of methyl bromide in ether (54 mmol, 2 eq.). The resulting solution was cooled to 5° C. and put under nitrogen before addition of 54 ml of $^t$BuOK (54 mmol, 2 eq.) diluted with 55 ml of DMSO using a syringe pump over a 3 h period. When thin-layer chromatographic analysis (5:1 toluene/acetone, NH$_4$OH) showed no starting material remaining, 200 ml of sat.aq. NaHCO$_3$ was added, and the mixture was extracted with 1 L of ethyl acetate. The organic extract was washed sequentially with saturated NaHCO$_3$, water, and brine. The organic phase was dried with MgSO$_4$, filtered, and evaporated. The crude product was purified by silica gel chromatography (gradient from hexanes to 10:1 hexanes/acetone+1% Et$_3$N), yielding 30 g of product. $^{13}$C NMR (CDCl$_3$, 100 MHz) δ 175.7, 169.8, 103.7, 102.6, 96.2, 80.8, 79.1, 78.6, 77.9, 73.7, 73.3, 73.1, 73.0, 69.7, 65.1, 65.1, 62.8, 51.1, 49.7, 49.1, 45.3, 41.0, 39.8, 37.7, 35.8, 34.6, 33.6, 33.1, 29.6, 28.0, 26.5, 25.6, 24.5, 24.4, 22.9, 22.2, 22.0, 20.2, 19.5, 18.6, 16.2, 15.8, 15.1, 9.6, 1.0, 0.8.

(e) Removal of Silyl and Acetal Protection.

A solution of the above product 6-O-methyl-2',4"-bis-O-trimethylsilyl-15-azidoerythromycin A 9-[O-(1-isopropoxy-cyclohexyl)]-oxime in 150 ml of acetonitrile was treated with 75 ml of water and 90 ml of acetic acid, and stirred for 18 hours at ambient temperature. The mixture was concentrated after addition of 2-propanol, then repeatedly after addition of toluene. Chromatography of the residue on silica gel (gradient from 2:1 to 1:1 hexanes/acetone+1% Et$_3$N) gave 20 g of 6-O-methyl-15-azidoerythromycin A 9-oxime as white solid. $^{13}$C NMR (CDCl$_3$, 100 MHz) δ 175.4, 169.7, 102.8, 96.1, 80.4, 78.8, 78.4, 78.0, 73.8, 73.0, 72.7, 71.1, 70.0, 68.6, 65.6, 65.5, 51.1, 49.5, 49.1, 45.7, 45.0, 40.3, 39.3, 37.4, 34.9, 32.6, 29.0, 27.8, 25.3, 21.4, 20.0, 19.8, 18.6, 16.1, 15.7, 15.0, 10.6, 9.1.

(f) Deoximation.

A solution of 6-O-methyl-15-azidoerythromycin A 9-oxime (20 g, 25.1 mmol) and sodium hydrosulfite (85%, 52.0 g, 254 mmol, 10 eq.) in 350 ml of 1:1 ethanol/water was placed under inert atmosphere. Formic acid (4.82 ml, 127.8 mmol, 5 eq.) was added dropwise, and the mixture was stirred at 80° C. for 4.5 hours. After cooling to ambient temperature, the reaction was adjusted to pH 10 with 6 N NaOH and extracted three times with 250-ml portions of ethyl acetate. The organic extracts were combined and washed sequentially with saturated NaHCO$_3$, water, and brine. The organic phase was dried with MgSO$_4$, filtered, and evaporated to yield 16 g of 6-O-methyl-15-azidoerythromycin A. $_{13}$C NMR (CDCl$_3$, 100 MHz) δ 221.0, 175.6, 102.8, 96.1, 80.6, 78.4, 78.3, 77.9, 74.0, 72.7, 72.6, 70.9, 68.7, 68.7, 65.8, 65.6, 50.6, 49.5, 49.0, 45.2, 44.9, 40.2, 39.4, 39.4, 37.1, 34.8, 28.7, 27.6, 25.3, 21.4, 19.7, 18.7, 17.9, 16.0, 15.6, 12.4, 9.0.

EXAMPLE 81

2'-O-benzoyl-6-O-methyl-3-descladinosyl-11-amino-11-deoxy-3-15-azidoerythromycin A 11,12-cyclic carbamate (a) Benzoylation of the 2' and 4" Hydroxyl Groups.

To a solution of 14 g of 6-O-methyl-15-azidoerythromycin A (17.7 mmol, 1.0 eq.) in a mixture of 28 ml of tetrahydrofuran and 112 ml of ethyl acetate was added 11.62 g of benzoic anhydride (51.4 mmol, 2.9 eq.), 2.17 g of 4-(dimethylamino)pyridine (17.7, 1eq.), and 7.28 ml of triethylamine (52.3 mmol, 3 eq.) sequentially at ambient temperature. The resulting solution was stirred for 3 days. Analysis by thin-layer chromatography (5:1 toluene/acetone, $NH_4OH$) showed less than 10% starting material remaining. After addition of 200 ml of sat. $NaHCO_3$ the resulting mixture was extracted with 2×600 ml of ethyl acetate. The organic extracts were combined and washed sequentially with saturated $NaHCO_3$, water, and brine. The organic phase was dried with $MgSO_4$, filtered, and evaporated to give a slight yellow solid. Column purification on silica gel (8:1 hexane/acetone, +1% $Et_3N$ to 4:1 hexane/acetone, +1% $Et_3N$) yielded 12 g of the 2',4"-dibenzoate product. $^{13}C$ NMR ($CDCl_3$, 100 MHz) δ 220.9, 175.2, 166.1, 165.3, 133.3, 132.6, 130.8, 129.8, 129.6, 129.6, 128.3, 128.2, 100.2, 95.7, 80.3, 78.8, 78.2, 77.6, 73.8, 72.9, 72.7, 72.4, 68.7, 67.5, 63.6, 63.5, 50.3, 49.6, 48.9, 46.2, 45.1, 44.6, 40.8, 38.8, 38.5, 37.1, 35.2, 31.6, 27.6, 21.2, 19.8, 18.4, 17.7, 16.0, 15.5, 12.2, 9.3.

(b) Carbamate Formation.

To a solution of 12 g (12.0 mmol) of the 2',4"-dibenzoate from step (a) above in a mixture of 42 ml of freshly distilled THF and 15 ml of dry DMF was added 8.8 g of solid 1,1-carbonyldiimidazole (54.3, 4.5 eq.). The resulting mixture was stirred under nitrogen for 20 min. at ambient temperature before 8 ml of a 2 N solution of sodium bis(trimethylsilyl)amide (NaHMDS) in THF (16 mmol, 1.3 eq.) was added dropwise. The resulting mixture was stirred overnight under nitrogen. The temperature of the mixture was lowered to −15° C., and liquid $NH_3$ was added in by condensation of anhydrous ammonia gas using a dry ice condenser. The mixture was capped and stirred for 2 h at −15° C. Liquid $N_3$ was dripped in above mixture again before the mixture was capped, and stirred for another 2 h at 0° C. The mixture was capped and stirred at 0° C. for another 1 h after liquid $NH_3$ was dripped in the mixture for the third time. After the temperature of above mixture was raised to room temperature, 15 ml of a 1 N solution of potassium tert-butoxide in THF (15 mmol, 1.2 eq.) was added in dropwise, and the mixture was stirred overnight under nitrogen. Then the mixture was diluted with sat. $NaHCO_3$, and extracted with 2×600 ml of ethyl acetate. The organic extracts were combined and washed sequentially with saturated $NaHCO_3$, water, and brine. The organic phase was dried with $MgSO_4$, filtered, and evaporated to give a slight yellow solid, which was used for next step reaction without further purification.

(c) Cladinose Removal.

The crude product from step (b) was dissolved in 120 ml of EtOH and 120 ml of 2N aqueous HCl, and the resulting solution was heated at 45° C. for 4 h. The solution was cooled to room temperature, and the pH was adjusted to 9 by adding 4N NaOH. The mixture was extracted with 2×500 ml of ethyl acetate, the organic extracts were combined, and then washed sequentially with saturated $NaHCO_3$, water, and brine. The organic phase was dried with $MgSO_4$, filtered, and evaporated. The crude product was purified by silica gel chromatography (gradient from 3:1 hexanes/acetone+1% $Et_3N$, to 1:1 hexanes/acetone+1% $Et_3N$), yielding 5.7 g of product. $^{13}C$ NMR ($CDCl_3$, 100 MHz) δ 217.7, 174.8, 265.3, 158.0, 132.6, 130.6, 129.7, 128.2, 99.7, 83.4, 80.7, 77.9, 77.5, 72.1, 71.9, 68.9, 63.2, 57.9, 49.5, 48.4, 45.2, 43.9, 40.7, 38.7, 37.0, 35.8, 31.9, 28.5, 21.0, 19.2, 18.0, 14.8, 13.7, 13.3, 7.7.

EXAMPLE 82

2'-O-benzoyl-6-O-methyl-3-descladinosyl-11-amino-11-deoxy-3-15-aminoerythromycin A 11,12-cyclic carbamate hydrochloride 400 mg of 10% activated palladium on carbon was weighed out into a round bottom flask under nitrogen, and 50 ml of methanol was added in slowly followed by sequential addition of 400 mg of 2'-O-benzoyl-6-O-methyl-3-descladinosyl-11-amino-11-deoxy-3-15-azidoerythromycin A 11,12-cyclic carbamate (0.53 mmol) (Example 81) and 0.13 mL (2 eq.) of trimethylsilyl chloride. The atmosphere in the flask was then purged using a hydrogen balloon three times before the flask was closed and stirred vigorously under a hydrogen atmosphere overnight. The mixture was filtered, and the solid was washed with 3×50 ml of methanol. The combined methanol solution was evaporated under vacuum to give 380 mg of the amine hydrochloride, which was used without purification for the next reaction.

EXAMPLE 83

General procedure for 15-amidoketolide formation from 2'-O-benzoyl-6-O-methyl-3-descladinosyl-11-amino-11-deoxy-3-15-aminoerythromycin A 11,12-cyclic carbamate hydrochloride (a) To a solution of 26 mg of amine hydrochloride salt from Example 82, 1.3 eq. of $R^1COOH$, and 1.2 eq. of 1-hydroxybenzotriazole in 2 ml of dry dimethylformamide was added 1.2 eq. Of 1-[3-(dimethylamino)propyl]-3-ethylcarbodiimide hydrochloride, and 3 eq. of triethylamine at ambient temperature. The mixture was stirred overnight before it was diluted with 30 ml of sat $NaHCO_3$, and extracted with 50 ml of $CH_2Cl_2$. The organic extract was washed sequentially with saturated $NaHCO_3$, water, and brine. The organic phase was dried with $MgSO_4$, filtered, and evaporated to give a slight yellow solid, which was used for next step reaction without further purification.

(b) To the solution of the 3-hydroxyl compound from Step (a) above in 2 ml of $CH_2Cl_2$ was added an excess amount of $NaHCO_3$ and the Dess-Martin periodinane (4 eq.), and the resultant mixture was stirred at ambient temperature for 30 min. The mixture was treated with 15 mL of saturated aqueous sodium thiosulfate for 10 minutes, then diluted with sat. $NaHCO_3$, and extracted with $CH_2Cl_2$, the organic extract was washed sequentially with saturated $NaHCO_3$, water, and brine. The organic phase was dried with $MgSO_4$, filtered, and evaporated to give a slight yellow solid, which was used for next step reaction without further purification. The compound from step (b) above was dissolved in 2 ml of methanol and heated at 70° C. under stirring overnight. Evaporation of the methanol under vacuum gave a yellow solid, which was purified by flash column to provide final 15-amidoketolide.

EXAMPLE 84

11-amino-11-deoxy-3-descladinosyloxy-3-oxo-15-(3-(2-furyl)phenylacetamido)-erythromycin A 11,12-cyclic carbamate This compound was prepared according to the methods of Example 83, using 3-(2-furyl)phenylacetic acid.

$^1H$ NMR ($CDCl_3$, 400 MHz) δ 7.53 (m, 2H), 7.45 (d, J=1.8 Hz, 1H), 7.40 (t, J=7.6 Hz, 1H), 7.12 (d, J=7.6 Hz,

1H), 6.65(d, J=3.3 Hz, 1H), 6.45 (d,d, J=1.8 Hz, J=3.3 Hz, 1H), 5.92 (s, 1H), 5.64 (s, 1H), 4.89 (d, J=5.6 Hz, 1H), 4.25 (d, J=7.2 Hz, 1H), 4.13 (d, J=8.0 Hz, 1H), 3.75 (q, J=6.4 Hz, 1H), 3.63 (s, 1H), 3.53 (m, 5H), 3.13 (m, 1H), 2.96 (m, 1H), 2.83 (m, 1H), 2.71 to 2.30 (m, 6H), 2.22 (s, 6H), 2.01 to 1.57 (m, 5H), 1.40 (s, 3H), 1.34 (d, J=6.8 Hz, 3H), 1.33 (s, 3H), 1.24 (d, J=7.6 Hz, 3H), 1.21 (d, J=6.0 Hz, 3H), 1.09 (d, J=6.4 Hz, 3H), 1.08 (d, J=6.0 Hz, 3H).

$^{13}$C NMR (CDCl$_3$, 100 MHz) δ 217.8, 203.9, 170.7, 169.4, 157.4, 153.4, 142.1, 135.2, 131.4, 129.3, 128.2, 124.7, 122.6, 111.6, 105.4, 103.8, 82.9, 79.2, 77.9, 72.9, 70.2, 69.5, 65.8, 57.8, 51.0, 49.1, 48.0, 44.4, 43.6, 40.1, 39.7, 37.3, 36.6, 29.2, 28.1, 21.1, 19.3, 17.6, 16.5, 16.5, 14.2, 13.5, 13.2.

EXAMPLE 85

11-amino-11-deoxy-3-descladinosyloxy-3-oxo-15-(3-quinolylacetamido)-erythromycin A 11,12-cyclic carbamate This compound was prepared according to the methods of Example 83, using 3-quinolyl-acetic acid.

$^1$H NMR (CDCl$_3$, 400 MHz) δ 8.78 (s, 1H), 8.07 (s, 1H), 8.01 (d, J=8.4 Hz, 1H), 7.77 (d, J=8.0 Hz, 1H), 7.62 (t, J=8.0 Hz, 1H), 7.48(d, J=7.6 Hz, 1H), 6.54 (s, 1H), 5.74 (s, 1H), 4.94 (d, d, J=2.4 Hz, J=10 Hz, 1H), 4.25 (d, J=7.2 Hz, 1H), 4.12 (d, J=8.0 Hz, 1H), 3.75 (q, J=6.8 Hz, 1H), 3.70 to 3.42 (m, 6H), 3.16 (m, 1H), 2.95 (m, 1H), 2.80 (m, 2H), 2.60 to 2.50 (m, 2H), 2.45 (s, 3H), 2.28 (s, 6H), 1.97 (m, 1H), 1.78 to 1.56 (m, 4H), 1.40 (s, 3H), 1.33 (d, J=6.8 Hz, 3H), 1.26 (s, 3H), 1.23 (d, J 8.0 Hz, 3H), 1.20 (d, J=6.4 Hz, 3H), 1.08 (d, J=6.8 Hz, 3H), 1.06 (d, J=6.4 Hz, 3H).

$^{13}$C NMR (CDCl$_3$, 100 MHz) δ 217.9, 203.9, 169.9, 169.6, 157.5, 151.6, 147.2, 136.0, 129.2, 129.0, 127.9, 127.8, 127.7, 126.7, 103.8, 83.0, 79.4, 77.9, 72.9, 70.2, 69.5, 65.7, 57.8, 51.0, 49.2, 48.2, 44.4, 40.6, 40.2, 39.8, 37.3, 35.7, 29.1, 28.0, 21.1, 19.4, 17.5, 16.7, 16.7, 14.2, 13.6, 13.2.

EXAMPLE 86

11-amino-11-deoxy-3-descladinosyloxy-3-oxo-15-(2-([1,2,4]-triazol-1-yl)pyrid-5-ylacetamido) erythromycin A 11,12-cyclic carbamate, This compound was prepared according to the methods of Example 83, using 2-([1,2,4]-tetrazol-1-yl)pyrid-5-ylacetic acid.

$^1$H NMR (CDCl$_3$, 400 MHz) δ 9.11 (s, 1H), 8.34 (s, 1H), 8.11(d, 1H), 7.86 (m, 2H), 6.21 (s, 1H), 5.92 (s, 1H), 4.82 (d, d, J=2.0 Hz, J=10.4 Hz, 1H), 4.25 (d, J=7.6 Hz, 1H), 4.10 (d, J=8.8 Hz, 1H), 3.75 (q, J=6.4 Hz, 1H), 3.71 to 3.46 (m, 6H), 3.16 (m, 1H), 2.96 (m, 1H), 2.82 (m, 1H), 2.71 to 2.40 (m, 3H), 2.49 (s, 3H), 2.32 (s, 6H), 2.02 to 1.96 (m, 1H), 1.82 to 1.55 (m, 4H), 1.43 (s, 3H), 1.37 (d, J=7.0 Hz, 3H), 1.27 (s, 3H), 1.24 (d, J=4.0 Hz, 3H), 1.23 (d, J=6.4 Hz, 3H), 1.08 (d, J=6.8 Hz, 3H), 1.10 (d, J=6.8 Hz, 6H).

$^{13}$C NMR (CDCl$_3$, 100 MHz) δ 217.7, 203.7, 169.9, 169.5, 157.5, 148.6, 148.4, 141.4, 140.0, 130.5, 129.6, 113.2, 82.9, 79.5, 78.0, 72.8, 70.2, 69.5, 65.8, 57.8, 51.0, 49.0, 48.3, 44.3, 40.1, 39.9, 39.7, 37.3, 35.4, 29.2, 28.9, 28.1, 21.1, 19.4, 17.5, 17.1, 14.2, 13.6, 13.2.

EXAMPLE 87

11-amino-11-deoxy-3-descladinosyloxy-3-oxo-15-(4-(3-pyridyl)imidazol-1-ylacetamido)erythromycin A 11,12-cyclic carbamate This compound was prepared according to the methods of Example 83, using 4-(3-pyridyl)imidazol-1-ylacetic acid.

EXAMPLE 88

Preparation of 3-(2-furanyl)phenylacetic Acid (a) Methyl 3-bromophenylacetate.

To a solution of 0.710 g of 3-bromophenylacetic acid (3.28 mmol) in 5 ml of methanol was added trimethylsilyl-diazomethane dropwise until the solution became yellow, then acetic acid was added dropwise until the solution was clear again. The solvent was then evaporated under vacuum to give the methyl ester of the bromophenylacetic acid, which was used for next step reaction without further purification.

(b) Methyl 3-(2-furanyl)phenylacetate.

The above ester, 2-furanboronic acid (1.44 g, 12.78 mmol, 3.9 eq.), and tetrakis(triphenylphosphine)palladium (0.38 g, 0.33 mmol) were weighed out into a round bottom flask. The mixture was degassed for 30 min. before 50 ml of freshly distilled THF and 2 mL of degassed saturated aqueous sodium carbonate were added in. The resulted mixture was heated at 50° C. overnight. After cooling to room temperature, the solution was concentrated under vacuum. Column purification (gradient from 5:1 hexanes/EtOAc, to 4:1 hexanes/EtOAc) yielded 0.40 g 3-furanylphenylacetic acid methyl ester.

(c) 3-(2-furanyl)phenylacetic Acid.

To a solution of the methyl 3-(2-furanyl)phenylacetate from step (b) in 5 ml of methanol was added 10 ml of 1N NaOH aqueous solution, the resulting solution was stirred overnight before diluting with 40 of ml 1N NaOH aqueous solution and washing with 2×30 ml CH$_2$Cl$_2$. The aqueous solution was then acidified with 2N HCl, and extracted with 3×30 ml of CH$_2$Cl$_2$. The organic extracts were combined and were dried with MgSO$_4$, filtered, and evaporated to give 0.32 g of the product as a golden-colored solid.

EXAMPLE 89

General Preparation of Aryl- and Heteroaryl-Acetic Acids

To a microwave reaction vial was added 30 mg of palladium(II) acetate (0.13 mmol, 13 mol %), 73 mg (0.18 mmol, 18%) of (2-dicyclohexanylphosphino)-2'-(N,N-dimethyl)biphenyl, and the vial was degassed under nitrogen for 15 min. before adding 2 ml of degassed dry toluene. The resulting solution was stirred for 10 min. before adding 1.5 ml of a 1 N solution of potassium tert-butoxide in THF and di-$^t$butyl malonate (3 mmol, 3 eq.) under nitrogen. The resulting mixture was stirred for 10 min. before the aryl bromide or heteroaryl bromide(1 mmol) was added in. The mixture was heated in a microwave reactor at 180° C. for 3 min. repeatedly until no starting material remained by thin-layer chromatographic analysis (5:1 toluene/acetone). Then methanol was added to the mixture before it was concentrated under vacuum. The mixture was then partially redissolved into CH$_2$Cl$_2$, and filtered. The filtrate was concentrated, and purified by silica gel column (from 15:1 hexanes/acetone to 5:1 hexanes/acetone) to yield around 200 mg of a yellow solid. To the solid in 10 ml of toluene was added 1 ml of trifluoroacetic acid, and the resulting solution was heated at 100° C. for 3 h. The solvent was evaporated under vacuum to yield around 80 mg of final product.

Compounds prepared according to this general procedure include:

(a) 3-quinolylacetic acid, using 3-bromoquinoline; and
(b) 2-([1,2,4]-triazol-1-yl)pyrid-5-yl-acetic acid, using 2-([1,2,4]-tetrazol-1-yl)-5-bromo-pyridine.

EXAMPLE 90

Preparation of 4-(3-pyridyl)imidazol-1-ylacetic Acid

To a solution of 55 mg of 4-(3-pyridyl)imidazole (0.38 mmol, 1.0 eq.) in 2 ml of dry of dimethylformamide was added 15.5 mg of NaH (60%) (0.38 mmol, 1.0 eq.), and the mixture was stirred vigorously for 10 min. before dropwise addition of 0.05 ml of tert-butyl bromoacetate (0.34 mmol, 0.9 eq.). The resulting solution was heated at 70° C. for 30 min before it was diluted with 20 ml of water, and extracted with 3×30 ml of ethyl acetate. The organic extracts were combined and washed sequentially with water, and brine. The organic phase was dried with $MgSO_4$, filtered, and evaporated to give 60 mg of a slight yellow solid.

To a solution of above solid in 5 ml of $CH_2Cl_2$ was added 5 ml of trifluoroacetic acid, and the resulting solution was stirred at room temperature for 3 h. The solvent was then evaporated under vacuum to give 35 mg of final product.

EXAMPLE 91

11-amino-11-deoxy-3-descladinosyloxy-2-fluoro-3-oxo-15-(3-(2-furyl)phenylacetamido)-erythromycin A 11,12-cyclic carbamate

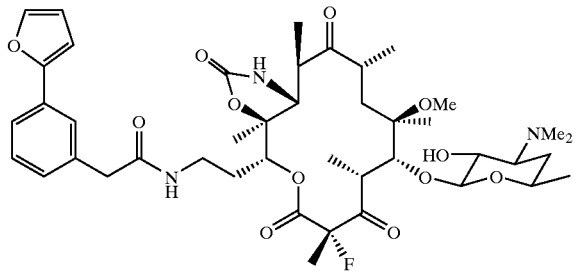

To a solution of 11-amino-11-deoxy-3-descladinosyloxy-3-oxo-15-(3-(2-furyl)phenylacetamido)-erythromycin A 11,12-cyclic carbamate in freshly distilled tetrahydrofuran (0.2 mmol/ml) was added 3.5 eq. of $^tBuOK$ (1N solution in THF) dropwise at −78° C. under $N_2$. The temperature of the resulting solution was allowed to slowly rise to −40° C. to −20° C., and the solution was stirred at this temperature for 10 min before a THF solution of N-fluorobenzenesulfonimide (0.6 mmol/ml) was added dropwise. The temperature of the resulting solution was then allowed to rise to 0° C. to −10° C., and the mixture was stirred at this temperature for 4 h before it was diluted with 100 ml of ethyl acetate and 30 ml of sat. aq. $NaHCO_3$. The organic layer was separated, washed sequentially with water and brine, then dried with $MgSO_4$, filtered, and concentrated under vacuum. The crude product was purified by silica gel chromatography (2:1 hexanes/acetone+1% $Et_3N$).

Subsequently debenzoylation by heating in methanol at 50° C. and column purification provided final product.

EXAMPLE 92

Microbiological Activity

Minimum inhibitory concentrations ("MICs") were determined by the NCCLS broth microdilution procedure for susceptibility testing for bacteria that grow aerobically (National Committee for Clinical Laboratory Standards, 1997. Methods for dilution antimicrobial susceptibility tests for bacteria that grow aerobically, $4^{th}$ ed. Approved standard. NCCLS Document M7-A4. National Committee for Clinical Laboratory Standards, Villanova, Pa.). Stock solutions were prepared on the day of the test and appropriate aliquots were added to cation adjusted Mueller-Hinton broth (CAMBB) or Haemophilus test media. Two-fold serial dilutions were prepared and added to wells in microtiter plates. Final test concentrations ranged from 16 to 0.015 ug/ml. Broth cultures of bacteria inoculated from growth on overnight plates for all test bacteria except Streptococcus pneumoniae and Haemophilus influenzae were incubated at 35° C. and then adjusted to the Kirby Bauer standard and diluted in CAMHB to achieve a final inoculum concentration of approximately $5×10^5$ CFU/ml. Inocula for S. pneumoniae and H. influenzae were prepared by directly suspending colonies from an overnight plate, adjusting the turbidity and diluting as above. S. pneumoniae media was supplemented with 2.5% lysed horse blood. All plates were incubated in ambient air at 35° C. for 20–24 h for S. pneumoniae and Haemophilus influenzae and 16–20 h for all other bacteria. The MIC endpoints were determined by reading the lowest concentration of test compound that completely inhibited the growth of the test bacteria. Results for compounds described in the above Examples are listed in Table 1.

TABLE 1

| Example | S. aureus OC4172 | S. pneumo OC9132 | S. pneumo OC4438 | S. pneumo ATCC6301 | H. influenzae ATCC49766 |
| --- | --- | --- | --- | --- | --- |
| Erythromycin A | 0.5 | 0.06 | 8 | 0.06 | 2 |
| 7 | 8 | 2 | >16 | nd | >16 |
| 8 | 16 | 1 | >16 | nd | >16 |
| 9 | 4 | 0.25 | >16 | nd | >16 |
| 10 | 1 | 0.25 | >16 | nd | 8 |
| 11 | 2 | nd | 16 | 0.25 | 8 |
| 13 | 4 | nd | 8 | 0.5 | >16 |
| 14 | 8 | nd | 8 | 0.25 | >16 |
| 15 | 1 | nd | 8 | 0.12 | 4 |
| 17 | 1 | nd | 4 | 0.06 | 2 |
| 18 | 0.5 | nd | 4 | 0.06 | 2 |
| 19 | 1 | nd | 4 | 0.12 | 2 |
| 20 | 4 | 0.5 | 16 | nd | 8 |
| 21 | 1 | nd | 16 | 0.12 | 4 |
| 23 | 8 | 1 | >16 | nd | >16 |
| 25 | 8 | 2 | >16 | nd | >16 |
| 26 | 16 | 2 | >16 | nd | >16 |
| 27 | 16 | 2 | >16 | nd | >16 |
| 29 | 8 | nd | >16 | 1 | >16 |
| 30 | 1 | 0.06 | 8 | nd | 4 |
| 84 | 0.06 | 0.25 | 0.25 | 0.015 | 0.5 |
| 85 | 1 | 0.25 | 4 | 0.25 | 8 |
| 86 | 0.5 | 0.25 | 2 | 0.06 | 2 |
| 87 | 8 | 1 | 8 | 1 | >16 | nd = not determined

The invention having now been described by way of written description, those of skill in the art will recognize that the invention can be practiced in a variety of embodiments, and that the foregoing description and examples, while describing the best mode contemplated by the inventors, is for purposes of illustration and not imitation of the following claims. All references cited herein, including patents, patent applications, PCT publications, papers, text books, and the like, and the references cited therein, to the extent that they are not already, are hereby incorporated herein by reference in their entirety.

What is claimed is:

1. A compound or pharmaceutically acceptable salt thereof having the formula

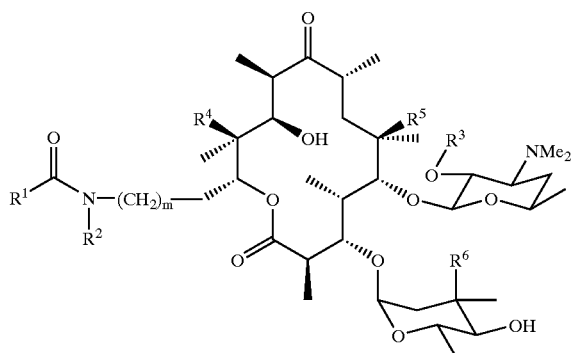

wherein
- $R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl;
- $R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;
- $R^3$ is H, $C_1$–$C_4$ alkanoyl, or benzoyl;
- $R^4$ is H or OH;
- $R^5$ is H, OH, $C_1$–$C_4$ alkoxy, $C_2$–$C_4$ alkenyloxy, or $C_2$–$C_4$ alkynyloxy;
- $R^6$ is OH or OMe; and m=0–2.

2. A compound of claim 1 wherein $R^2$ is H and m is 0.
3. A compound of claim 1 wherein $R^2$ is H and m is 1.
4. A compound of claim 1 wherein $R^2$ is H and m is 2.
5. A compound of claim 1 wherein $R^1$ a group having the formula

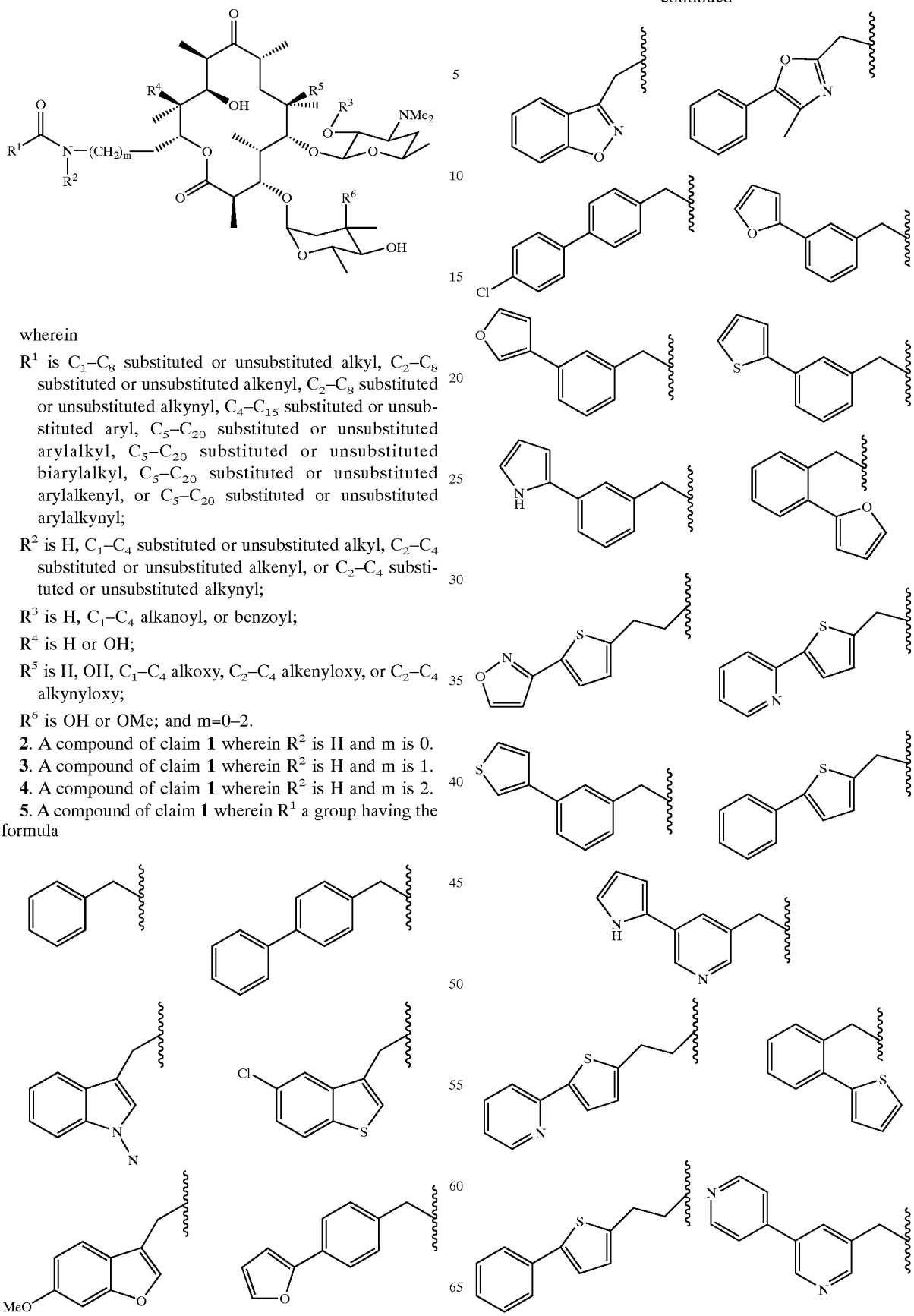

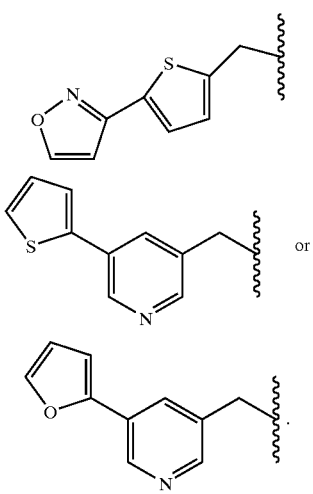
6. A compound of claim 1 having the formula
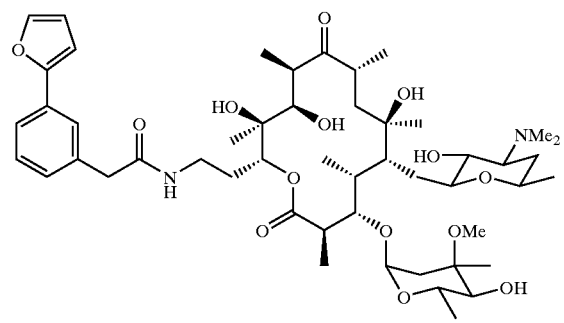
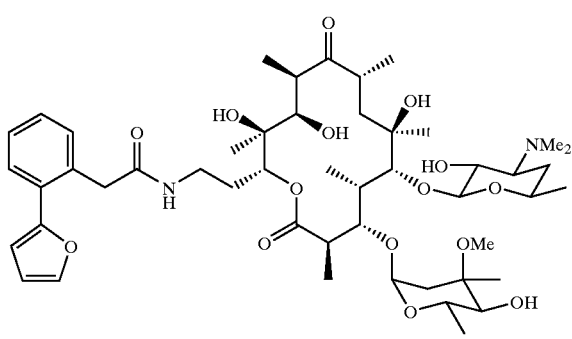
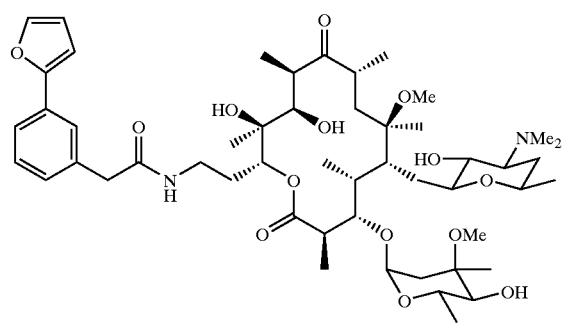
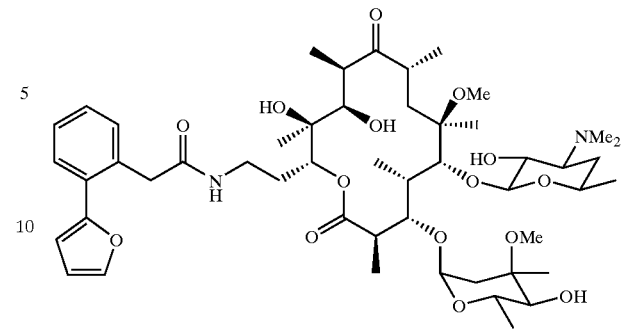
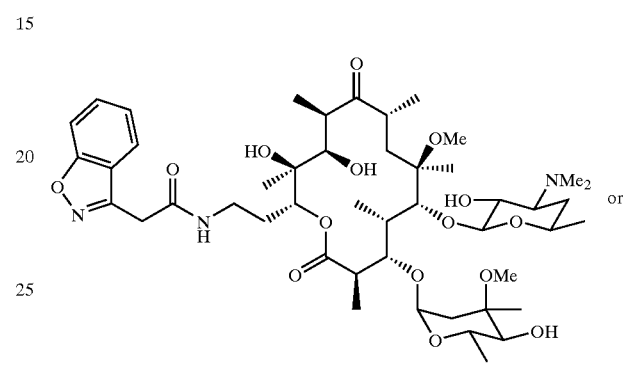
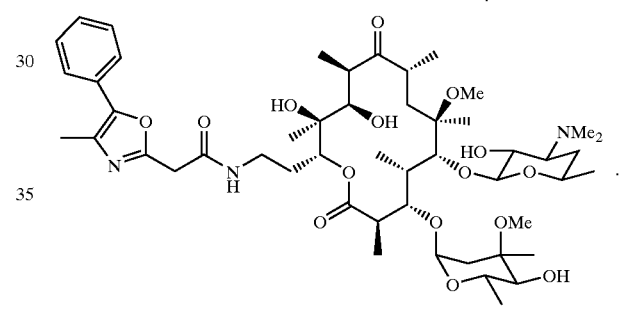
7. A compound or pharmaceutically acceptable salt thereof having the formula
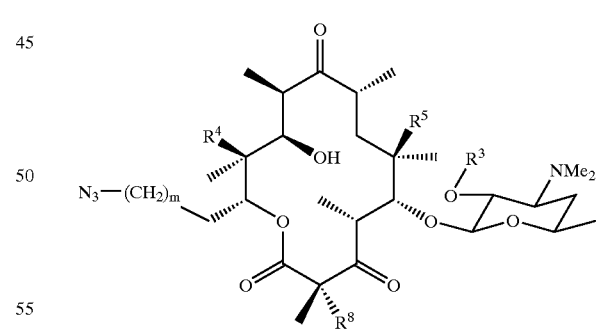
wherein
$R^3$ is H, $C_1$–$C_4$ alkanoyl, or benzoyl;
$R^4$ is H or OH;
$R^5$ is H, $C_1$–$C_4$ alkoxy, $C_2$–$C_4$ alkenyloxy, or $C_2$–$C_4$ alkynyloxy;
$R^8$ is H or F; and
m=0–2.

8. A compound of claim 7 wherein m=0.
9. A compound of claim 7 wherein m=1.
10. A compound of claim 7 wherein m=2.
11. A compound of claim 7 having the formula

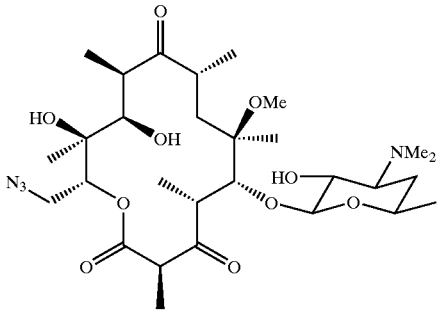

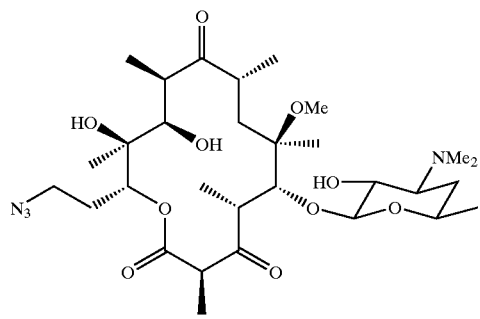

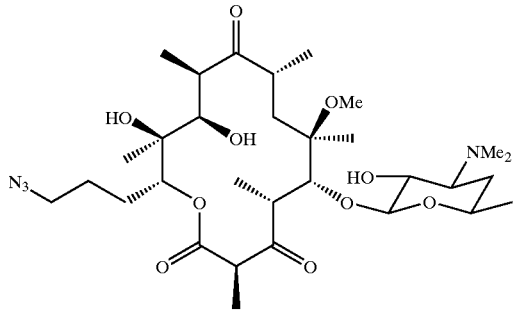

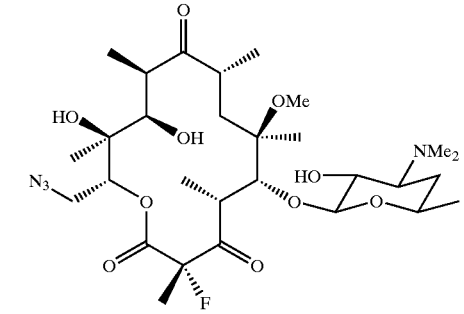

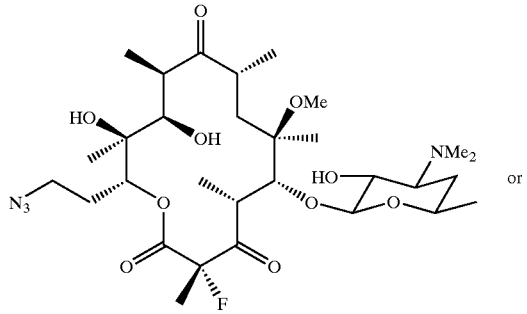 or

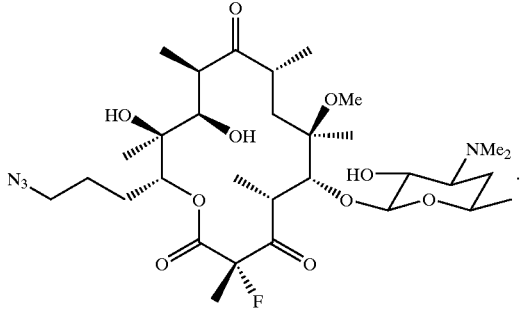

12. A compound or pharmaceutically acceptable salt thereof having the formula

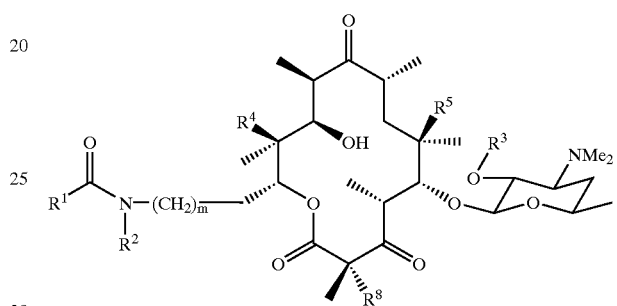

wherein $R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{18}$ substituted or Unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl;

$R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;

$R^3$ is H, $C_1$–$C_4$ alkanoyl, or benzoyl;

$R^4$ is H or OH;

$R^5$ is H, $C_1$–$C_4$ alkoxy, $C_2$–$C_4$ alkenyloxy, or $C_2$–$C_4$ alkynyloxy;

$R^8$ is H or F; and m=0–2.

13. A compound of claim 12 wherein m=0.
14. A compound of claim 12 wherein m=1.
15. A compound of claim 12 wherein m=2.
16. A compound of claim 12 wherein $R^1$ is $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; and $R^2$ is H.

17. A compound of claim 12 wherein R1 is a group of the formula

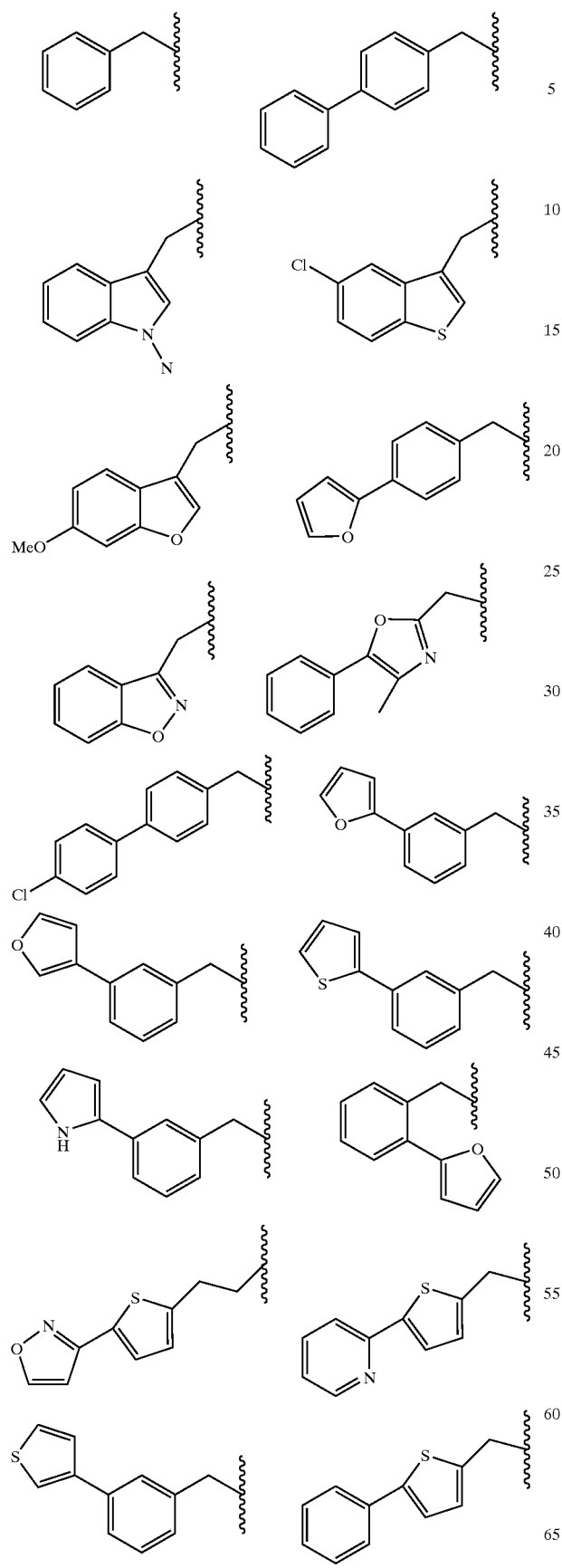

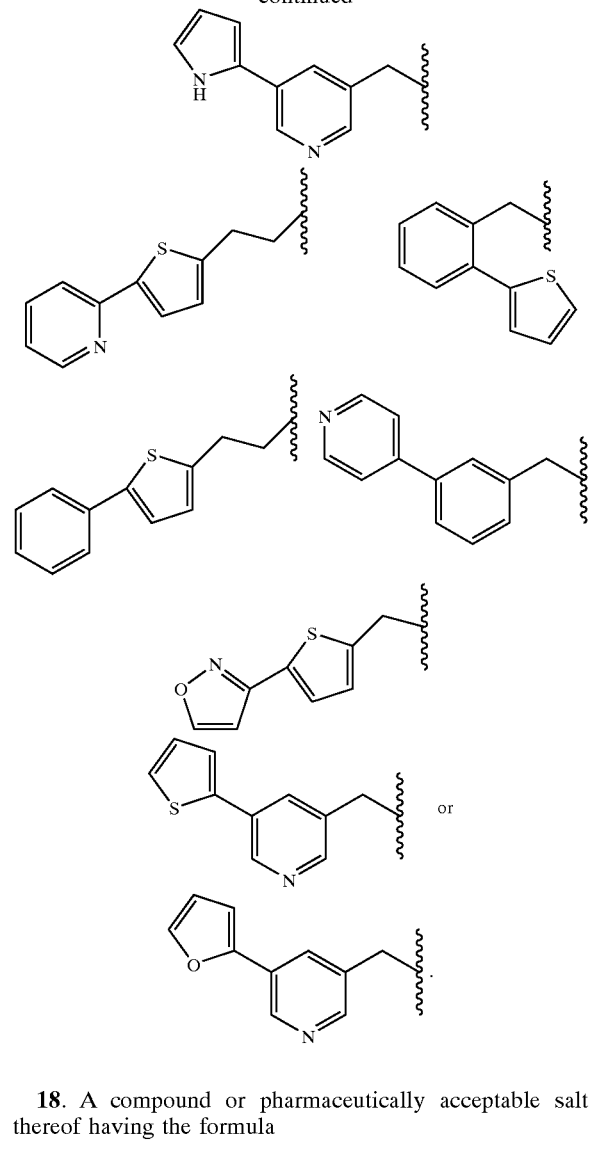

18. A compound or pharmaceutically acceptable salt thereof having the formula

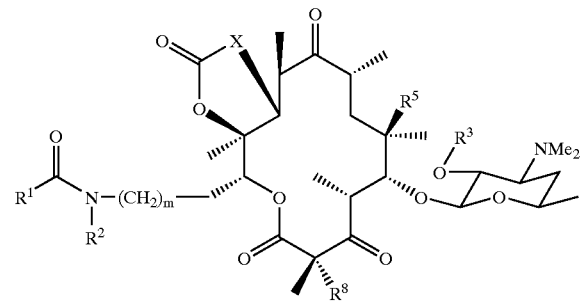

wherein $R^1$ is $C_1$–$C_8$ substituted or unsubstituted alkyl, $C_2$–$C_8$ substituted or unsubstituted alkenyl, $C_2$–$C_8$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$, substituted or unsubstituted arylalkynyl;

$R^2$ is H, $C_1$–$C_4$ substituted or unsubstituted alkyl, $C_2$–$C_4$ substituted or unsubstituted alkenyl, or $C_2$–$C_4$ substituted or unsubstituted alkynyl;

$R^3$ is H, $C_1$–$C_4$ alkanoyl, or benzoyl;

$R^5$ is H, $C_1$–$C_4$ alkoxy, $C_2$–$C_4$ alkenyloxy, or $C_2$–$C_4$ alkynyloxy;

$R^8$ is H or F;

X is O or $NR^7$, wherein $R^7$ is H, $C_1$–$C_4$ alkyl, or $C_6$–$C_{20}$ arylalkyl; and m=0–2.

19. A compound of claim 18 wherein $R^2$ is H.

20. A compound of claim 18 wherein $R^1$ is $C_6$–$C_{20}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; and $R^2$ is H.

21. A compound of claim 18 wherein $R^1$ is $C_5$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkynyl; $R^2$ is H; and X is NH.

22. A compound of claim 18 wherein $R^1$ is a group of the formula

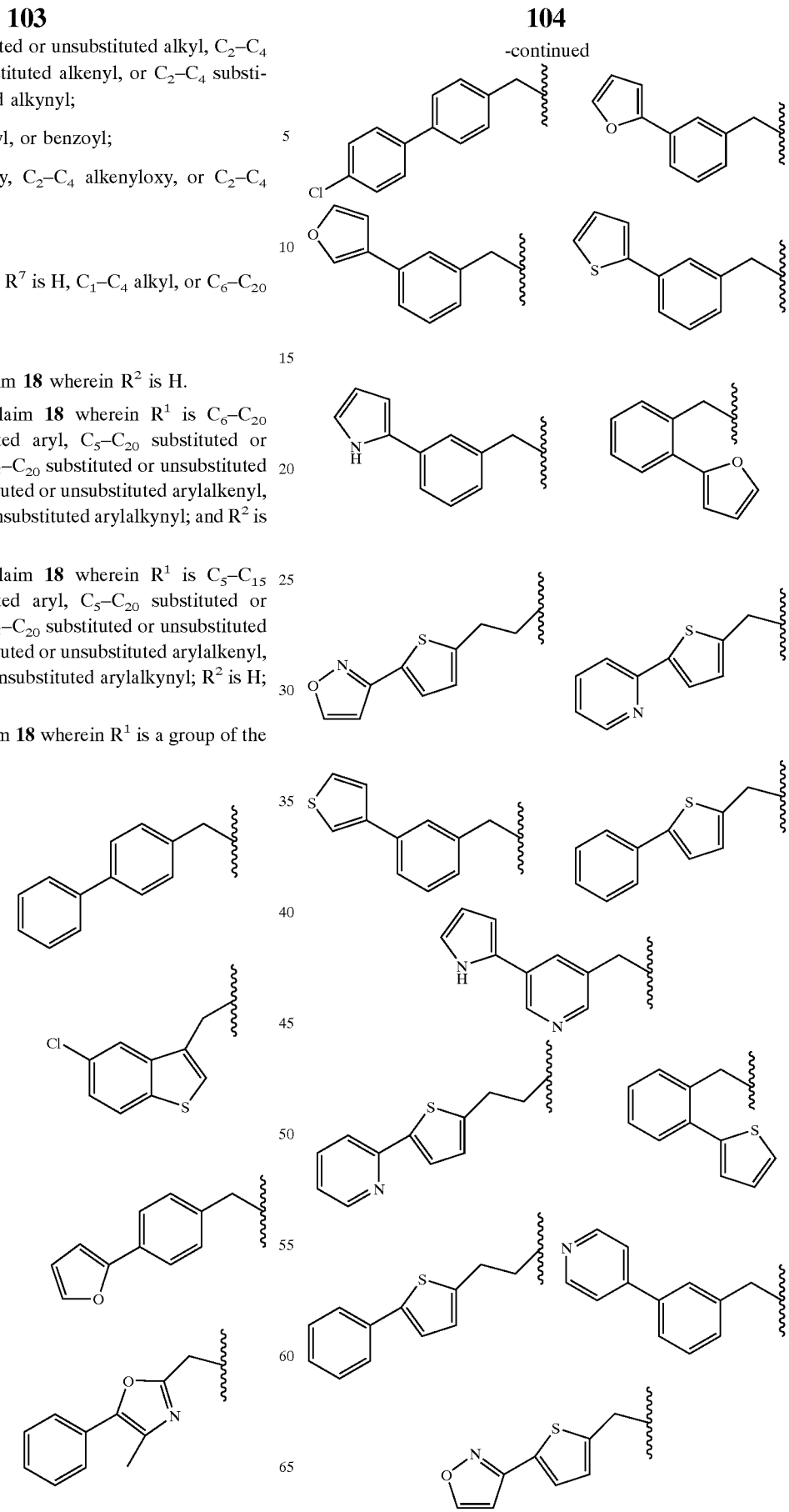

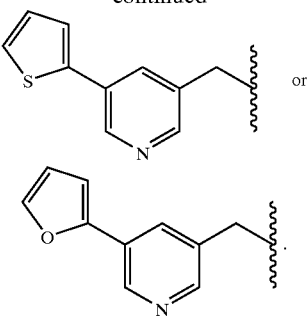

23. A compound of claim 18 having the formula

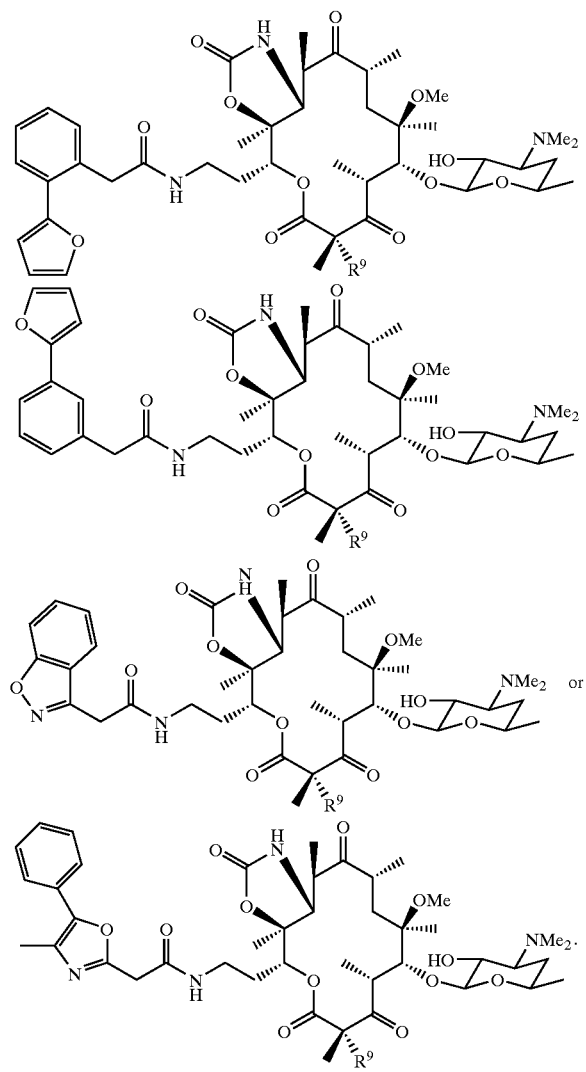

wherein $R^9$ is H or F.

24. A compound or pharmaceutically acceptable salt thereof having the formula:

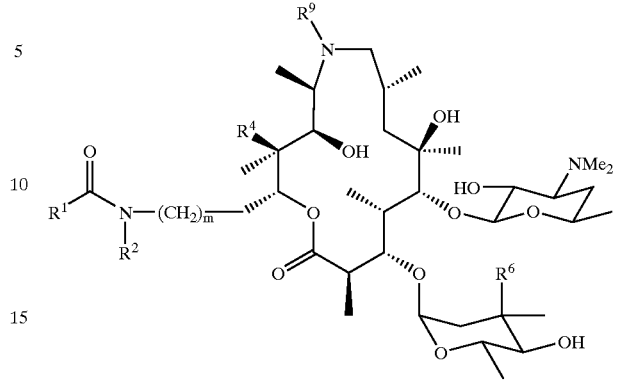

wherein $R^1$ is $C_1$–$C_8$ substituted or unsubstituted alkyl, $C_2$–$C_8$ substituted or unsubstituted alkenyl, $C_2$–$C_6$ substituted or unsubstituted alkynyl, $C_4$–$C_{15}$ substituted or unsubstituted aryl, $C_5$–$C_{20}$ substituted or unsubstituted arylalkyl, $C_5$–$C_{20}$ substituted or unsubstituted biarylalkyl, $C_5$–$C_{20}$ substituted or unsubstituted arylalkenyl, or $C_5$–$C_{20}$ substituted or unsubstituted arylalkenyl;

$R^2$ is H, $C_1$–$C_4$ substituted or unsubstituted alkyl, $C_4$–$C_4$ substituted or unsubstituted alkenyl, or $C_4$–$C_4$ substituted or unsubstituted alkynyl;

$R^4$ is H or OH;

$R^6$ is OH or OMe;

$R^9$ is H or $C_1$–$C_4$ alkyl; and m=0–2.

25. A pharmaceutical formulation, comprising the compound of any one of claims 1, 7, 12, 18, or 24 and a pharmaceutically acceptable carrier.

26. A method of treating a bacterial infection, comprising:
administering the compound of any one of claims 1, 7, 12, 18, or 24 to a patient having the bacterial infection.

27. The method of claim 26, wherein the bacterial infection results from bacteria selected from the group consisting of Gram positive bacteria, Gram negative bacteria and anaerobic bacteria.

28. The method of claim 27, wherein the bacteria are selected from the group consisting of *Staphylococcus aureus, Streptococcus epidermidis, Streptococcus pneumoniae, Streptococcus pyogenes*, enterococci, *Moraxella catarrhalis*, and *Haemophilus influenzae*.

29. The method of claim 26, wherein the bacterial infection is selected from the group consisting of community-acquired pneumonia, acute exacerbated chronic bronchitis, acute sinusitis, tonsillitis, pharyngitis, upper respiratory tract infection, lower respiratory tract infection, skin infection, soft tissue infection, meningitis, hospital-acquired infection, bone infection, and joint infection.

* * * * *

UNITED STATES PATENT AND TRADEMARK OFFICE
CERTIFICATE OF CORRECTION

PATENT NO. : 6,939,861 B2  Page 1 of 4
APPLICATION NO. : 10/347512
DATED : September 6, 2005
INVENTOR(S) : Gary Ashley et al.

It is certified that error appears in the above-identified patent and that said Letters Patent is hereby corrected as shown below:

Col. 10, line 55: Replace " 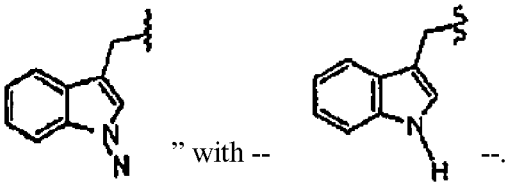 " with -- --.

Col. 30, line 24: Replace "formula (II)" with --formula (III)--.

Col. 33, line 41: Delete the phrase "a amine" and replace it with --amine--.

Col. 39, line 43: Replace " 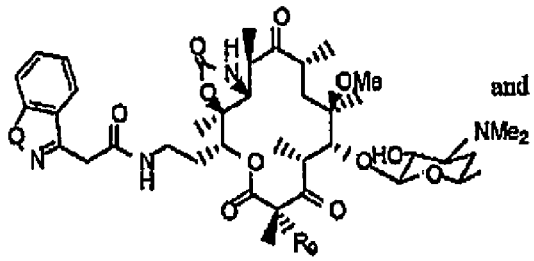 " with

-- 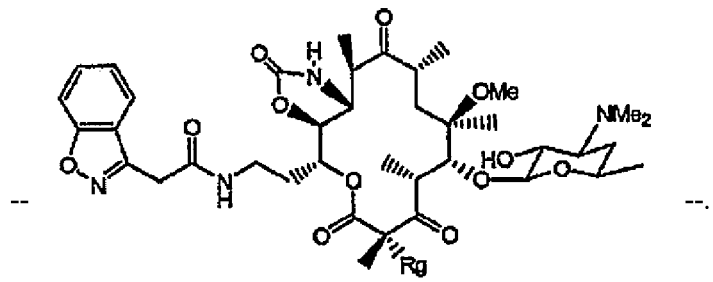 --.

UNITED STATES PATENT AND TRADEMARK OFFICE
CERTIFICATE OF CORRECTION

PATENT NO. : 6,939,861 B2
APPLICATION NO. : 10/347512
DATED : September 6, 2005
INVENTOR(S) : Gary Ashley et al.

It is certified that error appears in the above-identified patent and that said Letters Patent is hereby corrected as shown below:

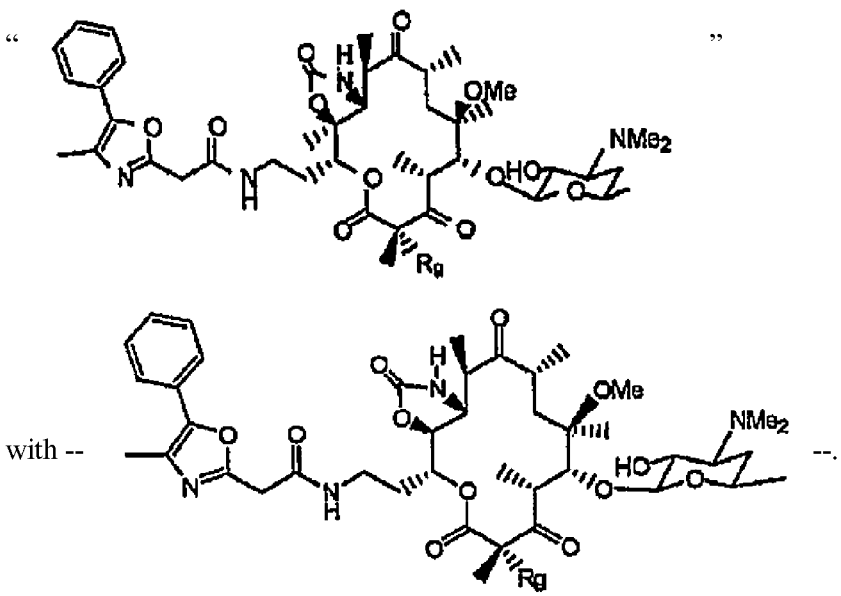

Col. 39, line 57: Replace " " with -- --.

Col. 49, line 21: Replace "resin20" with --resin/20--.

Col. 51, line 25: Replace "δ221.9" with --δ 221.9--.

Col. 57, line 40: Replace "15-(2-(2-furyl)phenylacetamido)erythromycin A" with --15-((1,2-benzisoxazol-3-yl)acetamido)erythromycin A--.

Col. 73, line 44: Replace "2′,4″bis-O-(trimethylsilyl)-6-O-azidoerythromycin A" with --2′,4″bis-O-(trimethylsilyl)-6-O-methyl-15-azidoerythromycin A--.

Col. 85, line 25: Replace "14-(azidomethyl)-6-deoxyerythronolide B" with --15-(azidomethyl)-6-deoxyerythronolide B--.

Col. 88, line 63: Replace "$_{13}$C" with --$^{13}$C--.

UNITED STATES PATENT AND TRADEMARK OFFICE
CERTIFICATE OF CORRECTION

PATENT NO. : 6,939,861 B2
APPLICATION NO. : 10/347512
DATED : September 6, 2005
INVENTOR(S) : Gary Ashley et al.

It is certified that error appears in the above-identified patent and that said Letters Patent is hereby corrected as shown below:

Col. 89, line 41: Replace "$N_3$" with --$NH_3$--.

Col. 95, line 41: Replace "$R^1$ a group having" with --$R^1$ is a group having--.

Col. 95, line 57: Replace " 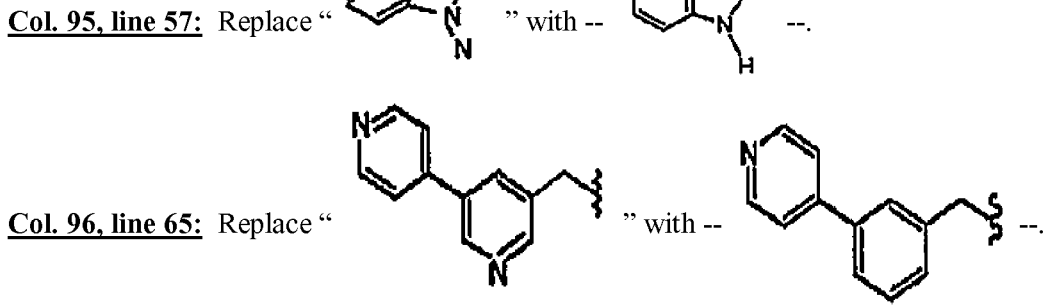 " with -- --.

Col. 96, line 65: Replace " 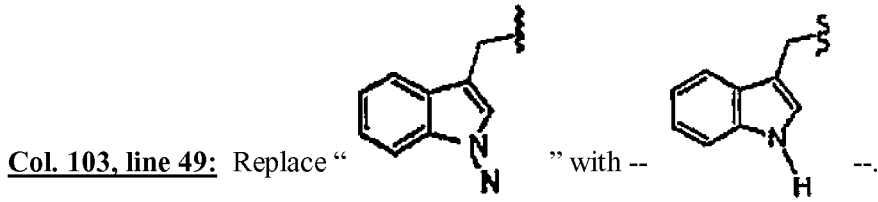 " with -- --.

Col. 103, line 18: Replace "$C_6$-$C_{20}$" with --$C_6$-$C_{15}$--.

Col. 103, line 25: Replace "$C_5$-$C_{15}$" with --$C_6$-$C_{15}$--.

Col. 103, line 49: Replace " " with -- --.

Col. 106, line 23: Replace "$C_2$-$C_6$" with --$C_2$-$C_8$--.

Col. 106, line 29: Replace "arylalkenyl;" with --arylalkynyl;--.

Col. 106, line 30: Replace "$C_4$-$C_4$" with --$C_2$-$C_4$--.

UNITED STATES PATENT AND TRADEMARK OFFICE
CERTIFICATE OF CORRECTION

| | |
|---|---|
| PATENT NO. | : 6,939,861 B2 |
| APPLICATION NO. | : 10/347512 |
| DATED | : September 6, 2005 |
| INVENTOR(S) | : Gary Ashley et al. |

It is certified that error appears in the above-identified patent and that said Letters Patent is hereby corrected as shown below:

Col. 106, line 31: Replace "$C_4$-$C_4$" with --$C_2$-$C_4$--.

Col. 106, line 51: Replace "*Morexella*" with --*Moraxella*--.

Signed and Sealed this

Ninth Day of January, 2007

JON W. DUDAS
*Director of the United States Patent and Trademark Office*